United States Patent
Nakamura et al.

(10) Patent No.: US 12,169,543 B2
(45) Date of Patent: *Dec. 17, 2024

(54) SYSTEM FOR FACE AUTHENTICATION AND METHOD FOR FACE AUTHENTICATION

(71) Applicant: PANASONIC INTELLECTUAL PROPERTY MANAGEMENT CO., LTD., Osaka (JP)

(72) Inventors: Kentarou Nakamura, Fukuoka (JP); Masashi Ozono, Kanagawa (JP); Takao Shime, Kanagawa (JP)

(73) Assignee: PANASONIC INTELLECTUAL PROPERTY MANAGEMENT CO., LTD., Osaka (JP)

(*) Notice: Subject to any disclaimer, the term of this patent is extended or adjusted under 35 U.S.C. 154(b) by 0 days.

This patent is subject to a terminal disclaimer.

(21) Appl. No.: 18/109,362

(22) Filed: Feb. 14, 2023

(65) Prior Publication Data

US 2023/0195875 A1 Jun. 22, 2023

Related U.S. Application Data

(63) Continuation of application No. 17/424,987, filed as application No. PCT/JP2019/042002 on Oct. 25, 2019.

(30) Foreign Application Priority Data

Feb. 1, 2019 (JP) .................................. 2019-017271

(51) Int. Cl.
G06F 21/00 (2013.01)
G06F 21/32 (2013.01)

(52) U.S. Cl.
CPC .................................. *G06F 21/32* (2013.01)

(58) Field of Classification Search
CPC .......... G06F 21/32; A61B 5/1171; G06T 7/00
See application file for complete search history.

(56) References Cited

U.S. PATENT DOCUMENTS 8,281,376 B2 10/2012 Kamakura
10,671,713 B2 * 6/2020 Zhang .................. G06V 10/806
(Continued)

FOREIGN PATENT DOCUMENTS

CN 102693415 9/2012
JP 2009-003805 1/2009
(Continued)

OTHER PUBLICATIONS

Office Action from U.S. Patent and Trademark Office (USPTO) in U.S. Appl. No. 17/424,987, dated Sep. 18, 2023.
(Continued)

*Primary Examiner* — Michael M Lee
(74) *Attorney, Agent, or Firm* — Greenblum & Bernstein, P.L.C.

(57) ABSTRACT

Provided is a system for face authentication which can operate separately for individual providers of face authentication service in a stable and efficient manner. The system includes: face authentication machines; an administrator terminal; a face management server for storing image data of registered users; and face matching servers, each configured to generate face feature amount data of a person to be verified from image data acquired from the camera of a face authentication machine and perform a matching operation by comparing the face feature amount data of the person with that of registered users. Prior to face authentication, data of associations between face authentication machines and face matching servers entered by an administrator is transmitted from the administrator terminal to the face management server.

4 Claims, 60 Drawing Sheets

(56) References Cited

U.S. PATENT DOCUMENTS

| | | | |
|---|---|---|---|
| 2003/0208555 | A1 | 11/2003 | Hong et al. |
| 2004/0010724 | A1 | 1/2004 | Brown et al. |
| 2009/0094254 | A1 | 4/2009 | Akita et al. |
| 2010/0058449 | A1* | 3/2010 | Kamakura .......... H04L 67/1008 726/6 |
| 2012/0130708 | A1 | 5/2012 | Furuya |
| 2013/0047229 | A1 | 2/2013 | Hoefel et al. |
| 2013/0117833 | A1 | 5/2013 | Ochi |
| 2013/0136320 | A1 | 5/2013 | Nishiguchi et al. |
| 2014/0133713 | A1* | 5/2014 | Kim ..................... G06V 40/172 382/118 |
| 2014/0165187 | A1 | 6/2014 | Daesung et al. |
| 2014/0230046 | A1 | 8/2014 | Dewan et al. |
| 2014/0241593 | A1* | 8/2014 | Koseki ................. G06V 40/16 382/118 |
| 2014/0294254 | A1* | 10/2014 | Kim ..................... G06V 40/165 382/118 |
| 2015/0169946 | A1 | 6/2015 | Needleman |
| 2016/0092724 | A1 | 3/2016 | Jeong |
| 2018/0373924 | A1 | 12/2018 | Yoo et al. |
| 2019/0057249 | A1 | 2/2019 | Hayase et al. |
| 2023/0195867 | A1 | 6/2023 | Nakamura et al. |

FOREIGN PATENT DOCUMENTS

| | | | |
|---|---|---|---|
| JP | 2010-061261 | 3/2010 | |
| JP | 5353147 | 11/2013 | |
| JP | 2017-068404 | 4/2017 | |
| JP | 2017-156777 | 9/2017 | |
| JP | 2018-169872 | 11/2018 | |
| WO | WO-2018180588 A1 * | 10/2018 | ............ G06F 16/00 |

OTHER PUBLICATIONS

International Search Report (ISR) from International Searching Authority (Japan Patent Office) in International Pat. Appl. No. PCT/JP2019/042002, dated Jan. 28, 2020, along with an English language translation.
Office Action from U.S. Patent and Trademark Office (USPTO) in U.S. Appl. No. 18/109,312, dated Nov. 2, 2023.
Office Action from U.S. Patent and Trademark Office (USPTO) in U.S. Appl. No. 18/109,048, dated Nov. 13, 2023.
Office Action from U.S. Patent and Trademark Office (USPTO) in U.S. Appl. No. 18/109,314, dated Nov. 14, 2023.
Office Action from U.S. Patent and Trademark Office (USPTO) in U.S. Appl. No. 18/108,721, dated Sep. 21, 2023.
Office Action from U.S. Patent and Trademark Office (USPTO) in U.S. Appl. No. 18/108,745, dated Oct. 4, 2023.
Office Action from U.S. Patent and Trademark Office (USPTO) in U.S. Appl. No. 18/109,001, dated Oct. 10, 2023.
Office Action from U.S. Patent and Trademark Office (USPTO) in U.S. Appl. No. 18/109,014, dated Oct. 26, 2023.
Office Action from U.S. Patent and Trademark Office (USPTO) in U.S. Appl. No. 18/108,721, dated Mar. 5, 2024.
Office Action from U.S. Patent and Trademark Office (USPTO) in U.S. Appl. No. 18/109,356, dated Dec. 7, 2023.
Office Action from U.S. Patent and Trademark Office (USPTO) in U.S. Appl. No. 18/109,366, dated Dec. 7, 2023.

* cited by examiner

Fig.14 log-in user ID password log-in

Fig.16

| | matching group | description | |
|---|---|---|---|
| ✓ | 1 | Tokyo | ▲ |
| ☐ | 2 | Yokohama | |
| ☐ | 3 | Fukuoka | |
| ✓ | 4 | Hokkaido | |
| ☐ | 5 | Okinawa | ▼ | matching group (deletion)

107 (checkboxes)

108 delete

Fig.23

| | face auth machine ID | match group | description |
|---|---|---|---|
| ✓ | V0000001 | 1 | Tokyo |
| ☐ | V0000001 | 2 | Yokohama |
| ☐ | V0000002 | 1 | Tokyo |
| ✓ | V0000002 | 3 | Fukuoka |
| ☐ | V0000003 | 1 | Tokyo | face auth machines (deletion)

face auth machine ID  —  ▼  — 117

116 prev   5  6  7  8  9  10  11  12  13  14   next delete — 118

Fig.30

| | face match server ID | match group | description |
|---|---|---|---|
| ✓ | V0000001 | 1 | Tokyo |
| ☐ | V0000001 | 2 | Yokohama |
| ☐ | V0000002 | 1 | Tokyo |
| ✓ | V0000002 | 3 | Fukuoka |
| ☐ | V0000003 | 1 | Tokyo | face matching servers (deletion)

face match server ID  — ▼  — 127

126 prev  5  6  7  8  9  10  11  12  13  14  next delete — 128

Fig.36

| user list | | | | | | |
|---|---|---|---|---|---|---|
| user code | last name | first name | match grp | · · · · · | select | |
| 1234567 | ○○ | ○○ | Tokyo, Yokohama | · · · · · | ✓ | |
| 1234568 | ○○ | ○○ | Fukuoka | · · · · · | ☐ | |

147 (label pointing to table)

prev     1 2 3     next execute — 148

Fig.56

| | authentication logs | | | | |
|---|---|---|---|---|---|
| 151 | face auth machine ID | x1234567 | | user ID | 00001 |
| | # of results | 100 | | | |
| | match date/time | 20180401 | ~ | 20180430 | |
| | match result | failure ▼ | | | search — 153 |

| | match date/time | match result | face image |
|---|---|---|---|
| 152 | yyyymmdd HHMMSS | failure | 👤 |
| | yyyymmdd HHMMSS | success | 👤 👤 |
| | yyyymmdd HHMMSS | failure | 👤 | prev  5  6  7  8  9  10  11  12  13  14  next   save — 154

SYSTEM FOR FACE AUTHENTICATION AND METHOD FOR FACE AUTHENTICATION

CROSS REFERENCE TO RELATED APPLICATIONS

This is a continuation of U.S. patent application Ser. No. 17/424,987, filed Jul. 22, 2021, which is a National Stage Entry of International Patent Application No. PCT/JP2019/042002, filed Oct. 25, 2019, which claims priority to Japanese Patent Application No. 2019-017271, filed Feb. 1, 2019. The entire disclosure of each of the above-identified documents, including the specification, drawings, and claims, is incorporated herein by reference in its entirety.

TECHNICAL FIELD

The present invention relates to a system for face authentication and a method for face authentication used for performing a face authentication process based on image data of a person to be verified.

BACKGROUND ART

Known face authentication technologies include a face authentication system which includes a first device including at least an extractor for extracting a registrant's face feature amount, a storage for storing registrants' feature amount data, and a matcher for performing a face feature amount matching operation; and a second device including a storage for storing face image data of registrants, the second device being provided at a location with a higher-security level than where the first device is provided, wherein, when face image data of registrants is necessary, the first device creates a data communication channel between the first and second devices, acquires registrants' face image data from the second device through the data communication channel, and uses the acquired data only on a memory region for data processing without storing it in any non-volatile storage, whereby, even when the first device of the face authentication system is stolen or attacked, the face image data of registrants can remain under protection as safely as possible (Patent Document 1).

PRIOR ART DOCUMENT(S)

Patent Document(s)

Patent Document 1: JP5353147B

SUMMARY OF THE INVENTION

Task to be Accomplished by the Invention

The above-described prior art document only teaches configurations in which a face authentication machine(s) is provided in physical space, and includes an image pickup device and a storage for storing face feature amount data of all the registrants, and performs a face matching operation, while face image data of the registrants is managed in cyber space (e.g., in an image server). Thus, the above-described prior art document fails to teach or suggest any configuration in which an authentication server is used; that is, both face feature amount data and face image data are stored in a cloud server or any other server, thereby enabling a face authentication system to operate separately for individual providers of face authentication service in a stable and efficient manner.

The present invention was made in view of such a problem of the prior art, and has a primary object to provide a system for face authentication and a method for face authentication used by the system, which enable the system to operate separately for individual providers of face authentication service in a stable and efficient manner.

Means to Accomplish the Task

An aspect of the present invention provides a system for face authentication used for performing a face authentication process based on image data of a person to be verified, comprising: a plurality of face authentication machines; a server device connected to the plurality of face authentication machines via a network; and a terminal device connected to the server device via the network, wherein each face authentication machine comprises a camera for shooting the person to be verified, wherein the server device comprises: a face image manager for storing and accumulating face image data of pre-registered users; and a plurality of face image matchers, each face image matcher being configured to generate face feature amount data of the person to be verified from image data shot by the camera of a face authentication machine, and perform a matching operation between the face feature amount data of the person to be verified and face feature amount data of the pre-registered users generated from the face image data thereof, wherein, in response to an administrator's entry operation on the terminal device, the server device is configured to acquire association information on associations between the plurality of face authentication machines and the plurality of face image matchers, and wherein each face authentication machine is configured to identify at least one face image matcher to which the face authentication machine is to make a request for performing the matching operation based on the association information acquired from the server device, and then make the request for performing the matching operation to the identified face image matchers.

Another aspect of the present invention provides a method for face authentication used for performing a face authentication process based on image data of a person to be verified, wherein the method is performed by a system for face authentication which comprises a plurality of face authentication machines; a server device connected to the plurality of face authentication machines via a network, the server device comprising a face image manager and a plurality of face image matchers; and a terminal device connected to the server device via the network, the method comprising: upon registration of users, the face image manager storing and accumulating face image data of the users; and performing the face authentication process, the performing comprising: a face authentication machine shooting the person to be verified by its camera to generate image data of the person to be verified; and then the plurality of face image matchers generating face feature amount data of the person to be verified from image data shot by the camera, and performing a matching operation between the face feature amount data of the person to be verified and face feature amount data of the registered users generated from the face image data thereof, wherein, prior to performing the face authentication process, in response to an administrator's entry operation on the terminal device, the terminal device transmits association information on associations between the plurality of face authentication machines and the plurality of face image matchers to the server device.

Effect of the Invention

According to the present invention, for each face authentication machine, a corresponding face image matcher(s) in a server device performs a matching operation (an operation for face data comparison for matching), which generally incurs high computational load on a processing device. This configuration reduces the computational load on a face authentication machine and eliminates the need for face authentication machines to store data requiring privacy protection, thereby enabling a system for face authentication to operate separately for individual providers of face authentication service in a stable and sufficient manner.

BRIEF DESCRIPTION OF THE DRAWINGS

FIG. 14 is an explanatory diagram showing a login screen displayed on an administrator terminal 2;

FIG. 16 is an explanatory diagram showing a screen displayed on the administrator terminal 2 when data of a matching group is to be deleted;

FIG. 23 is an explanatory diagram showing a screen displayed on the administrator terminal 2 when associations between face authentication machines 1 and matching groups are to be deleted;

FIG. 30 is an explanatory diagram showing a screen displayed on the administrator terminal 2 when associations between face matching servers 6 and matching groups are to be deleted;

FIG. 36 is an explanatory diagram showing a screen displayed on the administrator terminal 2 when data of a user is to be registered, viewed, updated, and deleted;

FIG. 56 is an explanatory diagram showing an authentication log view screen displayed on an administrator terminal 2;

DESCRIPTION OF THE PREFERRED EMBODIMENT(S)

Figure 1:
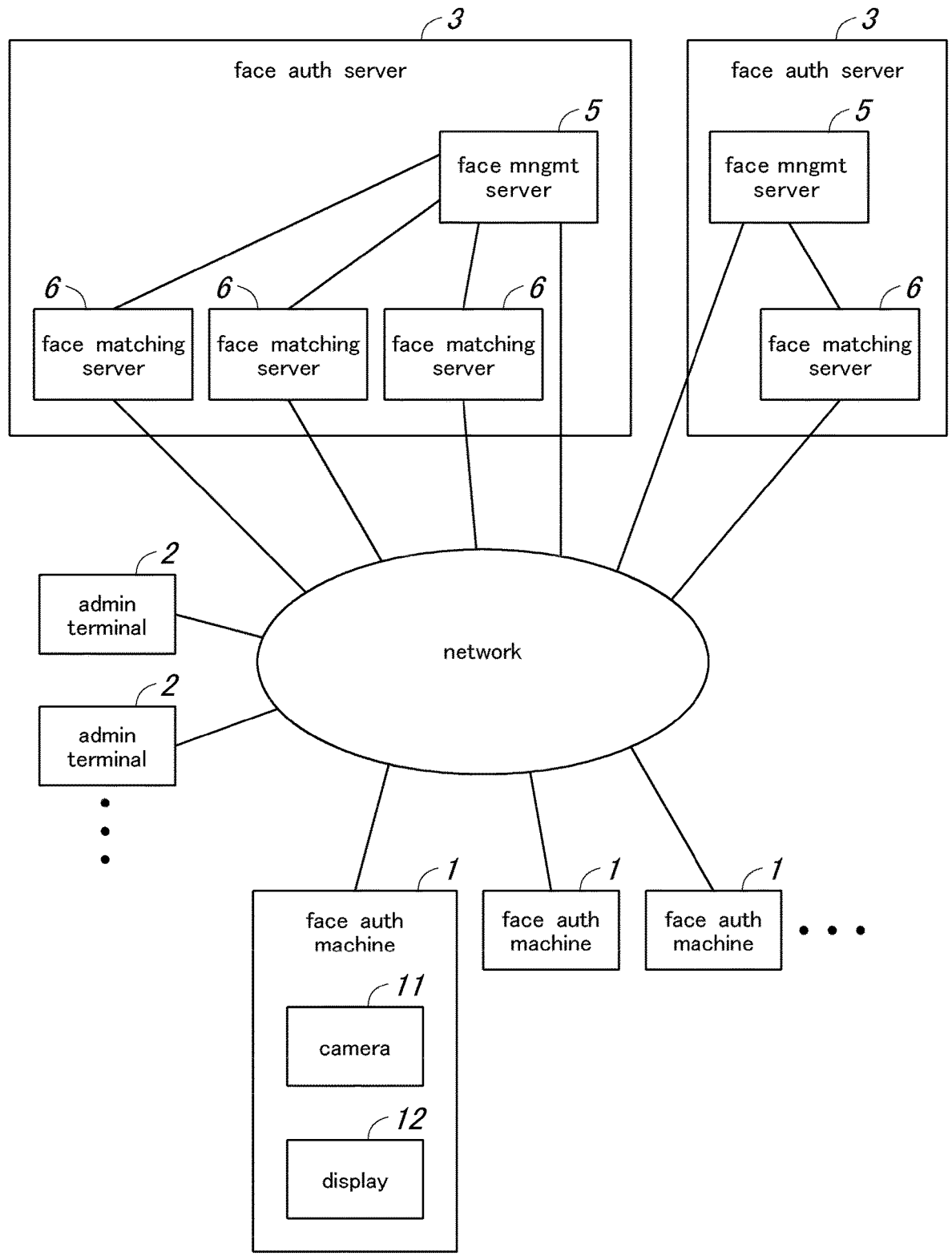
FIG. 1 is a diagram showing a general configuration of a face authentication system according to an embodiment of the present invention.

A first aspect of the present invention made to achieve the above-described object is a system for face authentication used for performing a face authentication process based on image data of a person to be verified, comprising: a plurality of face authentication machines; a server device connected to the plurality of face authentication machines via a network; and a terminal device connected to the server device via the network, wherein each face authentication machine comprises a camera for shooting the person to be verified, wherein the server device comprises: a face image manager for storing and accumulating face image data of pre-registered users; and a plurality of face image matchers, each face image matcher being configured to generate face feature amount data of the person to be verified from image data shot by the camera of a face authentication machine, and perform a matching operation between the face feature amount data of the person to be verified and face feature amount data of the pre-registered users generated from the face image data thereof, wherein, in response to an administrator's entry operation on the terminal device, the server device is configured to acquire association information on associations between the plurality of face authentication machines and the plurality of face image matchers, and wherein each face authentication machine is configured to identify at least one face image matcher to which the face authentication machine is to make a request for performing the matching operation based on the association information acquired from the server device, and then make the request for performing the matching operation to the identified face image matchers.

In this configuration, for each face authentication machine, a corresponding face image matcher(s) in a server device performs a matching operation (an operation for face data comparison for matching), which generally incurs high computational load on a processing device. This configuration reduces the computational load on a face authentication machine and eliminates the need for face authentication machines to store data requiring privacy protection, thereby enabling a system for face authentication to operate separately for individual providers of face authentication service in a stable and sufficient manner.

A second aspect of the present invention is the system of the first aspect, wherein each server device is provided for a corresponding provider of face authentication service.

This configuration enables two or more providers of face authentication service to utilize the face authentication system.

A third aspect of the present invention is the system of the first aspect, wherein the server device is configured to provide a network address of a face image matcher to the face authentication machines as the association information.

This configuration enables a face authentication machine to identify a face image matcher(s) to which the face authentication machine is to make a request for face matching, and request the identified face image matcher(s) to perform a matching operation.

A fourth aspect of the present invention is a method for face authentication used for performing a face authentication process based on image data of a person to be verified, wherein the method is performed by a system for face authentication which comprises a plurality of face authentication machines; a server device connected to the plurality of face authentication machines via a network, the server device comprising a face image manager and a plurality of face image matchers; and a terminal device connected to the server device via the network, the method comprising: upon registration of users, the face image manager storing and accumulating face image data of the users; and performing the face authentication process, the performing comprising: a face authentication machine shooting the person to be verified by its camera to generate image data of the person to be verified; and then the plurality of face image matchers generating face feature amount data of the person to be verified from image data shot by the camera, and performing a matching operation between the face feature amount data of the person to be verified and face feature amount data of the registered users generated from the face image data thereof, wherein, prior to performing the face authentication process, in response to an administrator's entry operation on the terminal device, the terminal device transmits association information on associations between the plurality of face authentication machines and the plurality of face image matchers to the server device.

This method enables the face authentication system to operate separately for individual providers of face authentication service in a stable and sufficient manner, in the same manner as the first aspect.

Embodiments of the present invention will be described below with reference to the drawings.

FIG. 1 is a diagram showing a general configuration of a face authentication system according to an embodiment of the present invention.

This face authentication system includes face authentication machines 1, administrator terminals 2 (terminal devices, face authentication administrator devices), and face authentication servers 3 (cloud servers). A face authentication server 3 includes a face management server 5 (face image manager) and one or more face matching servers 6 (face image matchers).

The face authentication machines 1, the administrator terminals 2, the face management servers 5, and the face matching servers 6 are connected to each other via a network such as the Internet. A face authentication system is built for each provider of face authentication service (business operator). A plurality of face authentication machines 1 are installed at respective places where face authentication is required, such as the entrance/exit of a building or the entrance/exit of a room. A required number of face matching servers 6 are provided according to the number of face authentication machines 1 and other factors.

A face authentication machine 1 includes a camera 11 for acquiring a shot image of a user. A face authentication machine 1 also includes a display 12 for displaying a face authentication result acquired from the face matching server 6 to notify the user of the face authentication result.

An administrator terminal 2 is operated by an administrator, is comprised primarily of a personal computer, in which a management application is installed for managing the operations of face authentication machines 1, face management servers 5, and face matching servers 6. The management application allows an administrator to perform various management tasks. The management application is implemented as a Web application.

The face management server 5 provides unified management of user data. Specifically, the face management server 5 accumulates and manages user data such as first names, last names and face images of registered users.

When a face authentication process is performed, the face matching server 6 acquires face image data of a person to be verified from a face authentication machine(s) 1, generates face feature amount data of the person to be verified, and performs a face matching operation by comparing the face feature amount data of the person to be verified with face feature amount data of registrants (registered users) in the face matching server 6 for matching to determine whether or not the person to be verified is a registrant.

Furthermore, upon user registration prior to a face authentication process, the face matching server 6 acquires face image data of a user form an administrator terminal 2, generates face feature amount data from the acquired face image data and stores it in the face matching server 6. In other embodiments, the face matching server 6 may acquire a shot image(s) of a user from an administrator terminal 2 and then generate face image data of the user from the shot image(s).

Although, in the present embodiment, the face management server 5 (face image manager) and the face matching servers 6 (face image matchers) are provided in physically separated information processing devices, respectively, these servers 5 and 6 may be provided within a single information processing device.

Although, in the present embodiment, an administrator terminal 2 and a face management server 5 are separately provided, an administrator terminal 2 and a face management server 5 can be configured by a single information processing device. For example, a face management server 5 can be configured to also serve as an administrator terminal 2 by installing an administrator terminal application on the face management server 5.

Although, in the present embodiment, a face matching server performs a face feature amount matching operation as a face matching operation, the face matching operation is not limited to operation for face feature amount matching, and may adopt any other matching operation such as a matching operation using machine learning technology. Furthermore, the present embodiment can be applied to any other biometric authentication other than face authentication.

Figure 2:
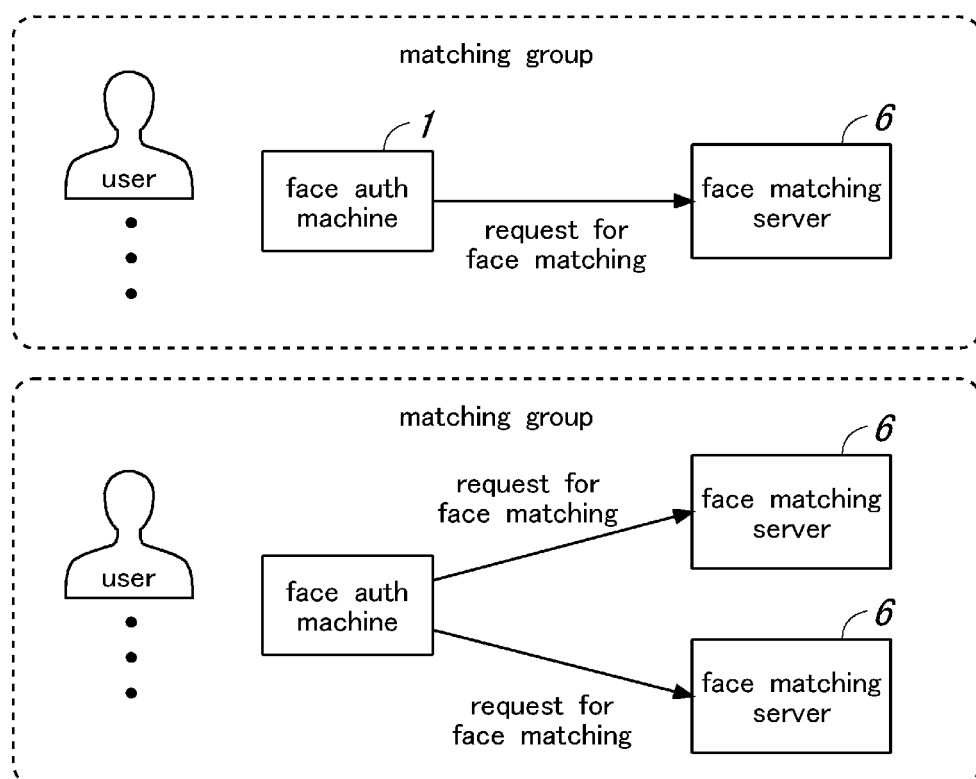
FIG. 2 is an explanatory diagram showing an outline of a concept of a matching group.

Next, matching groups will be described. FIG. 2 is an explanatory diagram showing an outline of a concept of a matching group.

In the present embodiment, matching groups are assigned to respective user groups formed by grouping users based on the locations of face authentication machines 1 at which the users are authenticated. Also, matching groups are assigned to respective groups of face authentication machines 1 formed by grouping authentication machines 1 based on the locations of the face authentication machines 1 in the same manner as the user groups. Furthermore, matching groups are assigned to corresponding face matching servers 6; that is, matching groups are assigned to groups of face matching servers 6, to which face authentication machines 1 make inquiries (requests) for face authentication, formed by grouping the face matching servers 6 in the same manner as the groups of face authentication machines 1.

For example, when a face authentication machine 1 is installed at the entrance of a multi-tenant building in which a plurality of companies are located as tenants, the face authentication machine 1 is used to authenticate users who belong to the companies in the building. However, user data of the users who belong to different organizations cannot be managed in a single database. In such cases, different matching groups are formed for respective companies, and user data records of the matching groups are separately stored so that the face authentication machine 1 can make an inquiry for face authentication to a face matching server(s) 6 of each matching group formed for a corresponding tenant company.

Users of each matching group can be authenticated only by a corresponding face authentication machine 1. Thus, even when a user is a registered user, the user cannot be authenticated by a face authentication machine 1 which does not belong to the matching group of the user (e.g., a face authentication machine 1 located at a building the user is not permitted to enter). For example, when a user working at a business office goes to a different business office, the user cannot be authenticated by a face authentication machine 1 located at the different business office.

Figure 3A:
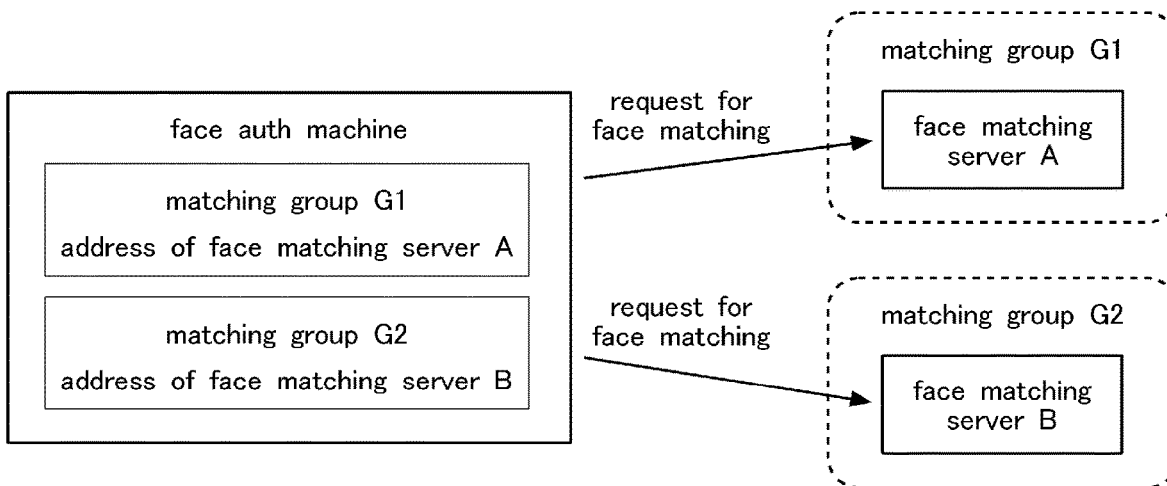
FIGS. 3A-C are explanatory diagrams showing outlines of face matching inquiry operations performed by a face authentication machine 1.
Figure 3B:
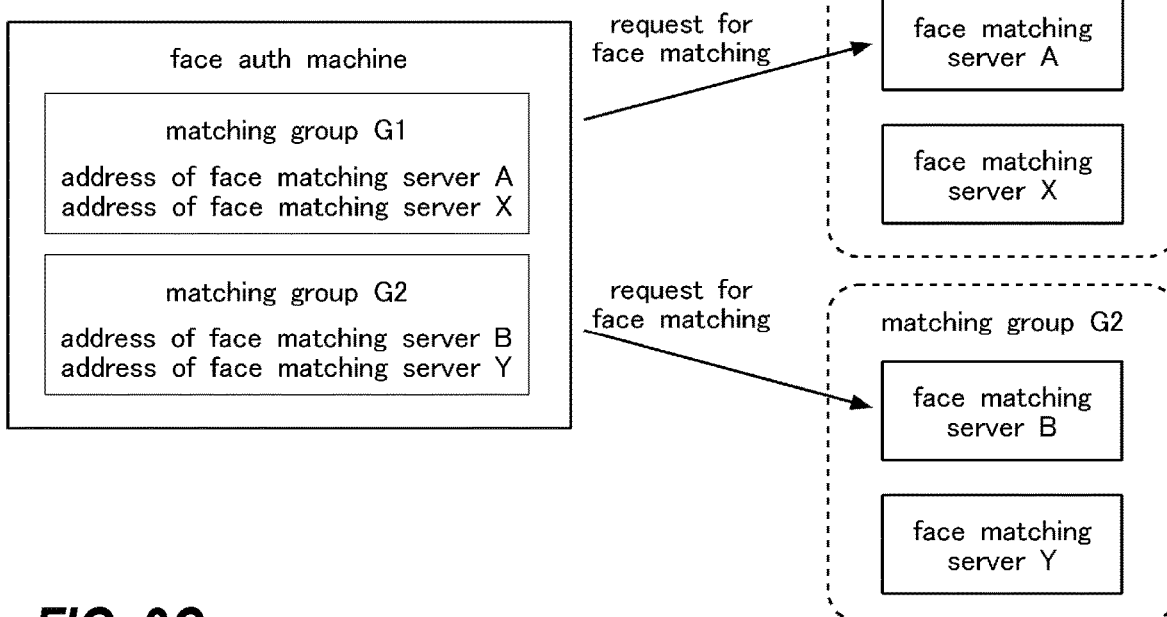
Figure 3C:
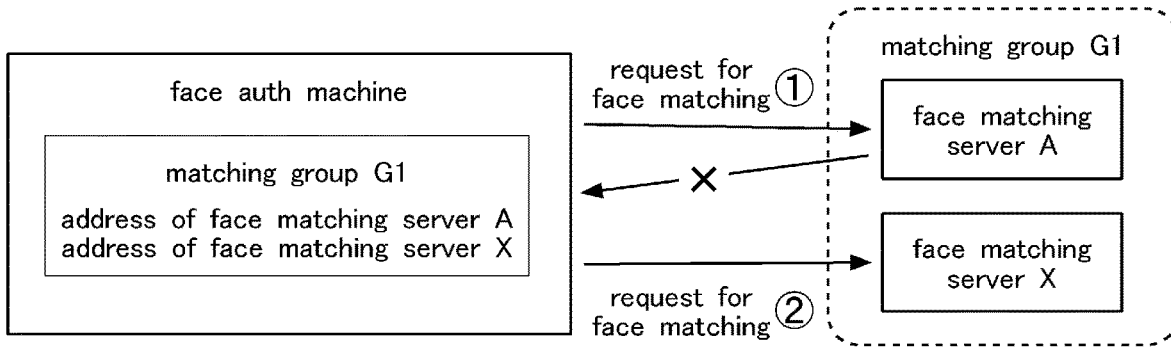

Next, inquiries for face matching will be described. FIGS. 3A-C are explanatory diagrams showing outlines of face matching inquiry operations performed by a face authentication machine 1.

A face authentication machine 1 makes an inquiry for face matching to a face matching server(s) 6 which belongs to the same matching group as the face authentication machine; that is, the face authentication machine 1 transmits a request for face matching to the face matching server 6 which can be an inquiry target (request target). A face authentication machine 1 stores the network addresses (IP addresses) of face matching servers 6 as part of matching group information, and thus can make an inquiry for face matching to its corresponding face matching server(s) 6 by using the network address.

There are three types of inquiries for face matching; a simultaneous inquiry process as shown in FIG. 3A, a random inquiry process as shown in FIG. 3B, and a sequential inquiry process (destination-switching inquiry process) as shown in FIG. 3C.

In the case of the simultaneous inquiry process as shown in FIG. 3A, a face authentication machine 1 simultaneously makes inquiries to face matching servers 6 for different matching groups. For example, when a face authentication machine 1 is located at an entrance of a multi-tenant building and users who belong to different matching groups are to be verified, the face authentication machine 1 simultaneously transmits face matching requests to different face matching servers 6 for the respective matching groups.

In some embodiments, face feature amount data of users of one common matching group may be divided into multiple data pieces to be separately stored in different face matching servers 6, thereby reducing the computational load on each face matching server 6. In this case, a face authentication machine 1 simultaneously makes inquiries to the different face matching servers 6 which belong to the same matching group as the face authentication machine 1, but store different data pieces.

In the case of the random inquiry process as shown in FIG. 3B, a face authentication machine 1 randomly selects one target face matching server 6 among multiple face matching servers 6 of the same matching group as the face authentication machine 1. The respective face matching servers 6 store the same registration data. In other words, all the face matching servers 6 can perform face matching operations on the same user and store the same user's face feature amount data. In this type of inquiry process, since inquiries made by one face authentication machine are distributed to multiple face authentication servers 6, the computational load on each face matching server 6 is reduced; that is, computational load distribution can be achieved.

In the case of the sequential inquiry process as shown in FIG. 3C, a face authentication machine 1 sequentially selects target face matching servers 6 one by one from multiple face matching servers 6 of the same matching group as the face authentication machine 1. Specifically, the face authentication machine 1 assigns an order (priority) to multiple face matching servers 6 and selects face matching servers one by one in this order. In this process, upon receiving no response to an inquiry from a face matching server 6 with a certain priority, the face authentication machine 1 switches the inquiry destination to the face matching server 6 with the next priority, and transmits a request for face matching to that face matching server 6. This configuration can add redundancy (backup capabilities) to the system.

Figure 4A:
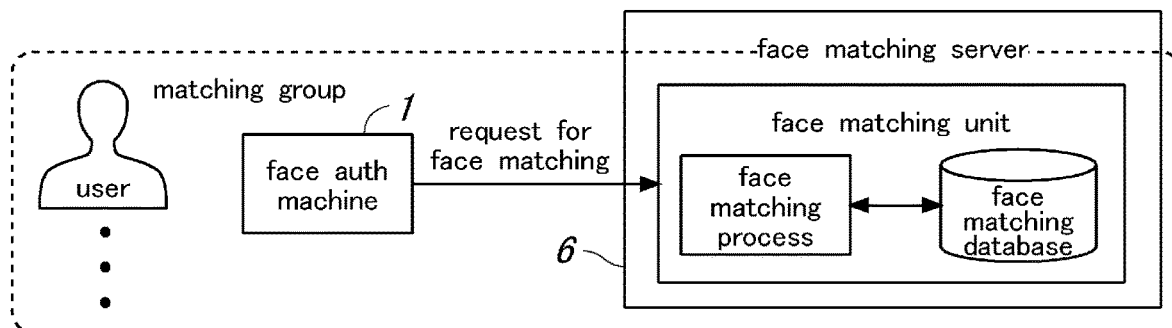
FIGS. 4A-C are explanatory diagrams showing outlines of concepts of a face matching unit.
Figure 4B:
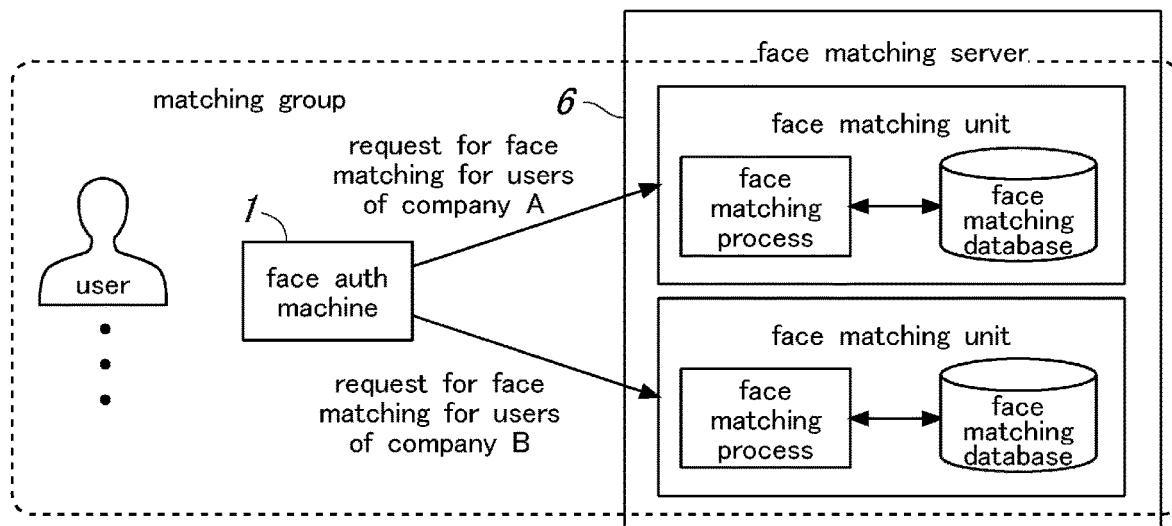
Figure 4C:
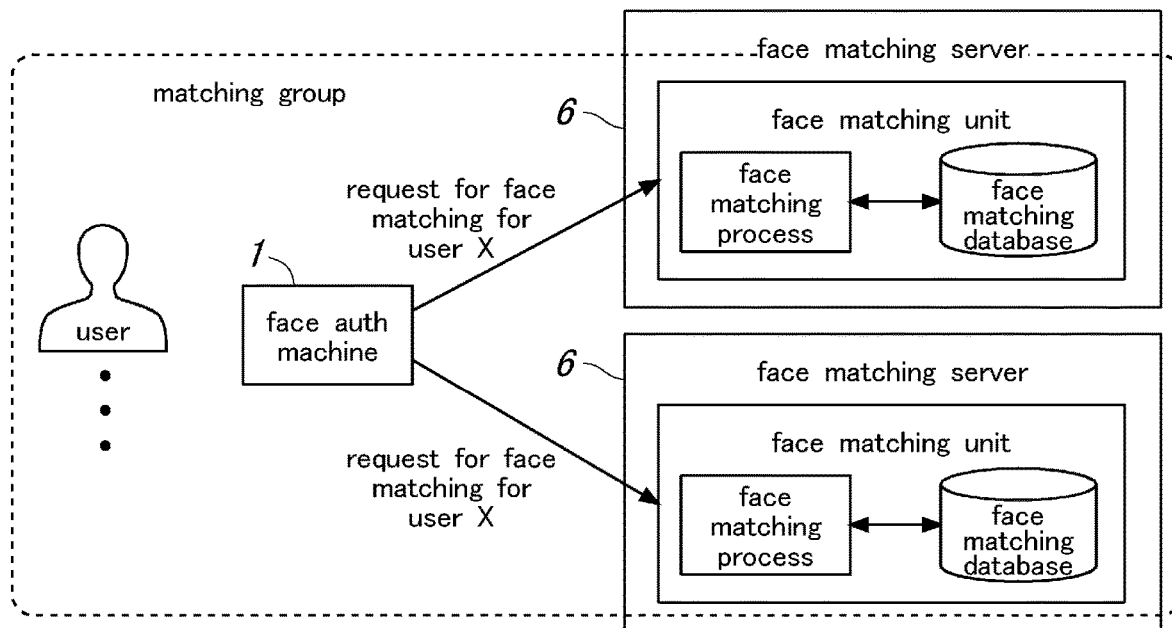

Next, a face matching unit will be described. FIGS. 4A-C are explanatory diagrams showing outlines of concepts of a face matching unit.

A plurality of face matching units may be provided in a face matching server 6 for performing operations for face matching. A face matching unit contains a face matching process which executes a face matching program and a face matching database which stores data of registered users (face feature amount data) to be compared with user data to be verified in operations for face matching.

Each face mitching unit is provided for a corresponding matching group and configured to perform a face matching operation in response to a request for face matching. Thus, one face matching server 6 can be used for a plurality of matching groups.

As described above, a face authentication machine 1 stores the network address (IP address) of a face matching server(s) 6 as part of matching group information, and thus can make an inquiry for face matching to a corresponding face matching server(s) 6 by using the network address. In the present embodiment, a face authentication machine 1 further stares the network address (IP address) of a face matching unit, and thus can make an inquiry for face matching to a corresponding face matching unit by using the network address.

Since a face matching database is provided for each matching group, face feature amount data of users can be stored separately for different matching groups. The face matching process executes a face matching operation in which stored face feature amount data for a matching group is compared with face feature amount data generated from face image data acquired from the face authentication machine 1 of the same matching group.

There are various types of correspondence between a face authentication machine 1 and one or more face matching units.

In the example shown in FIG. 4A, a face matching server 6 contains one face matching unit for the matching group of a face authentication machine 1, and thus the face authentication machine 1 has a one-to-one correspondence with the face matching server 6.

In the example shown in FIG. 4B, a face authentication machine 1 has a one-to-one correspondence with a face matching server 6, but the face matching server 6 contains two face matching units for the matching group of the face authentication machine 1. In this case, when the face authentication machine 1 is installed at the entrance of a multi-tenant building, data of users of different organizations (for example, users A and users B) can be managed separately in different matching databases.

In the example shown in FIG. 4C, a face authentication machine 1 has a one-to-two correspondence with face matching servers 6, and thus the face authentication machine 1 makes inquiries for face matching (requests for face matching for a user X) to the two face matching servers 6. In this case, since different face matching servers 6 each contain the same face matching unit; that is, multiple face matching units perform face matching operations with the use of face feature amount data of the same user, the system can achieve the distribution of computational load on multiple face matching servers 6 and provide a fail-safe against server failure.

Figure 5:
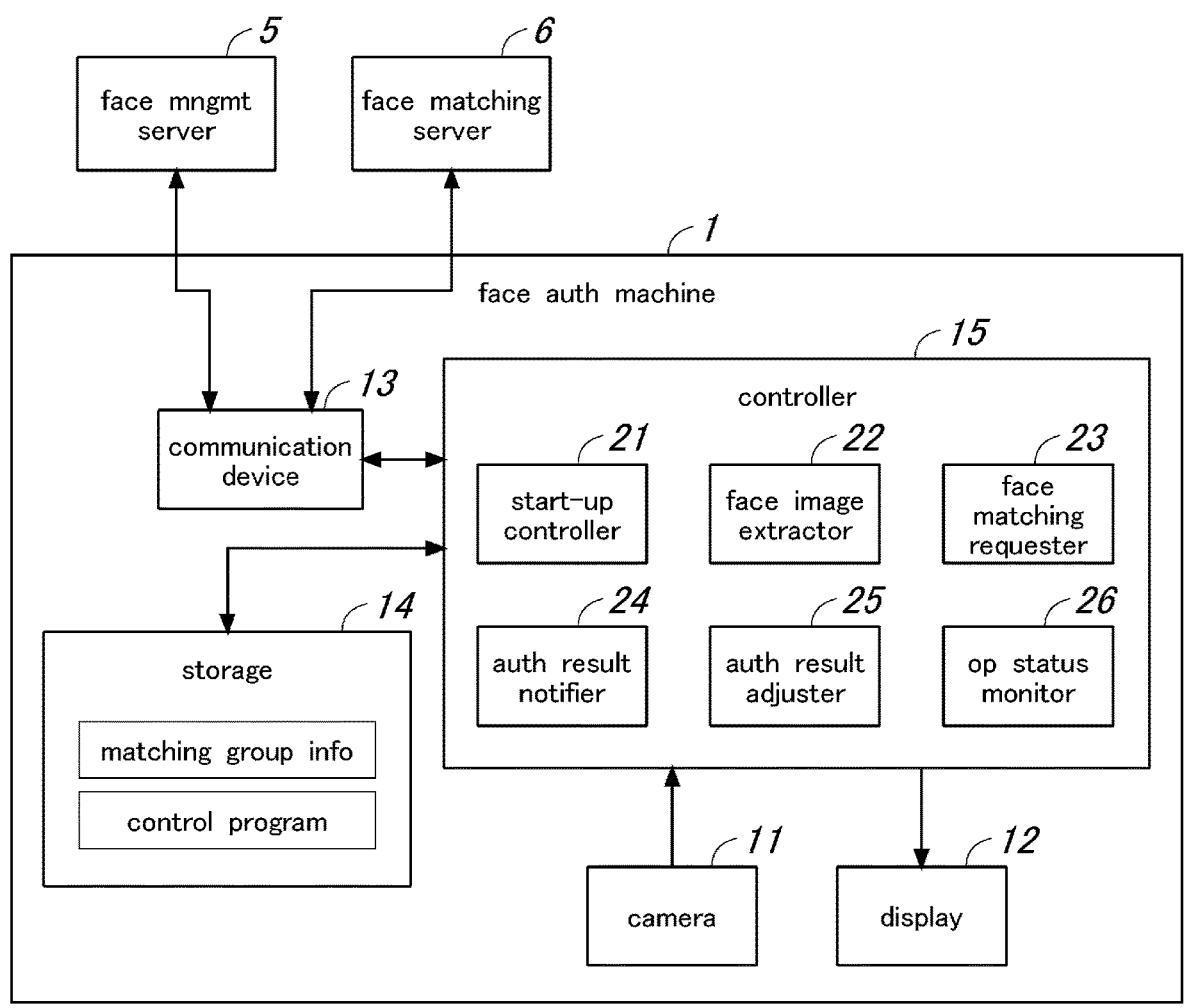
FIG. 5 is a block diagram showing a schematic configuration of a face authentication machine 1.

Next, a schematic configuration of a face authentication machine 1 will be described. FIG. 5 is a block diagram showing a schematic configuration of a face authentication machine 1.

A face authentication machine 1 includes a camera 11 (image pickup device), a display 12 (output device), a communication device 13, a storage 14, and a controller 15.

The camera 11 constantly shoots a predetermined shooting area so that, when a person enters the shooting area, the person is shot; that is, the camera can acquire an image of a person to be verified. In some cases, a motion sensor (not shown) may be provided to detect a person who comes close and activate the camera, thereby saving electrical power.

The display 12 displays a face authentication result so that a person to be verified can confirm the face authentication result. In some cases, a speaker may be used as an additional output device to output a face authentication result for a person to be verified, notifying the person of the face authentication result by voice or sound.

The communication device 13 (face image transmitter, authentication result receiver) communicates with a face matching server(s) 6 via the network. In the present embodiment, the communication device 13 transmits face image data to a face matching server 6. The communication device 13 also receives the user's authentication result from a face matching server 6. Moreover, the communication device 13 communicates with a face management server 5 via the network. In the present embodiment, the communication device 13 receives matching group information or other information from a face management server 5.

The storage 14 stores matching group information, control programs to be executed by a processor, which implements the controller 15, and other information.

The controller 15 includes a start-up controller 21, a face image extractor 22, a face matching requester 23, an authentication result notifier 24, an authentication result adjuster 25, and an operation status monitor 26. The controller 15 is configured by the processor, and each functional unit of the controller 15 is implemented by the processor executing a program stored in the storage 14.

When the face authentication machine 1 starts up, the start-up controller 21 acquires matching group information from a face management server 5 and stores the acquired information in the storage 14. The way the face authentication machine acquires matching group information is not limited to this method. For example, when matching group information is updated, a face management server 5 may deliver the matching group information to the target face authentication machine 1.

The face image extractor 22 acquires a captured image (shot image) of a person to be verified from the camera 11 (camera image capture); detects a face of the person from the shot image (face detection); determines whether or not the detected face size is appropriate (face size check); and cuts out a face region from the shot image (face cut-out) to thereby acquire the face image data of the person to be verified. The face image data may be in the form of the image data of a face region only, or in the form of a combination of data of the shot image and data of the position of a face region in the shot image (face frame data).

The face matching requester 23 transmits a request for face matching to a face matching server 6 of the same matching group as the face authentication machine.

The authentication result notifier 24 displays a face authentication result acquired from a face matching server 6 on the display 12 to notify the user of the face authentication result.

Figure 57:
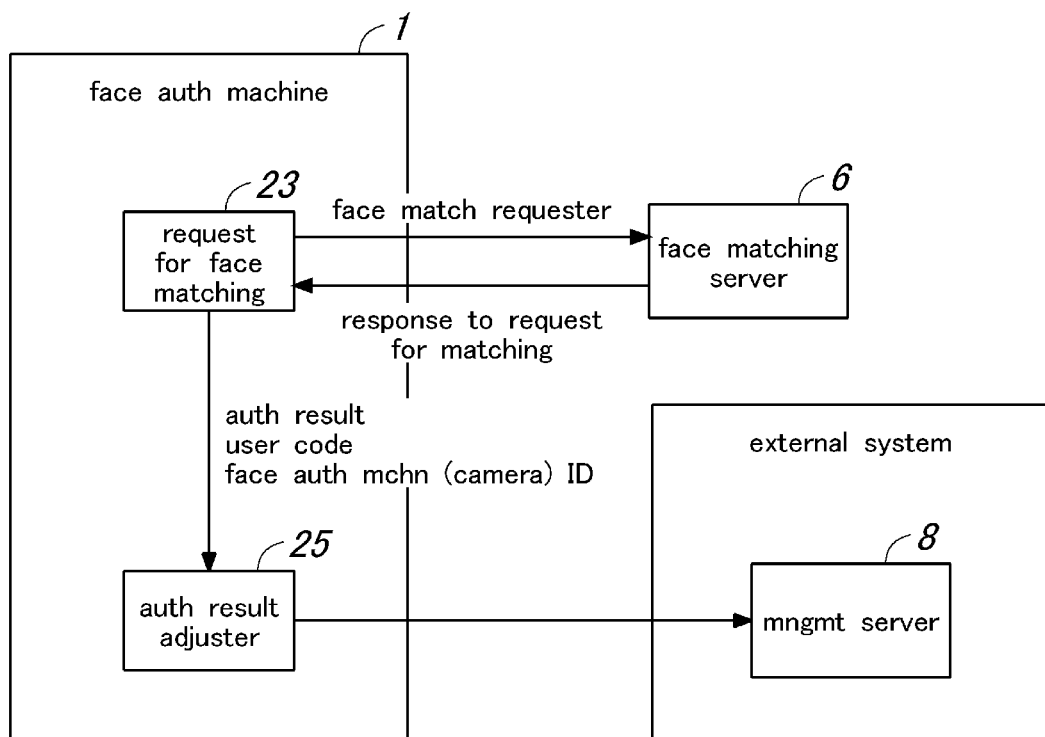
FIG. 57 is an explanatory diagram showing an outline of dynamic data linking from a face authentication machine to external applications.

The authentication result adjuster 25 performs control to share a face matching result of a user acquired from a face matching server 6 with a management server 8 (external device) of an external system shown in FIG. 57, which will be described later. The authentication result adjuster 25 is implemented by a connection application, and configured to notify the management server 8 of face matching results of users.

The operation status monitor 26 monitors the operation status of the face authentication machine 1 and notifies a face management server 5 of the operation status.

Figure 6:
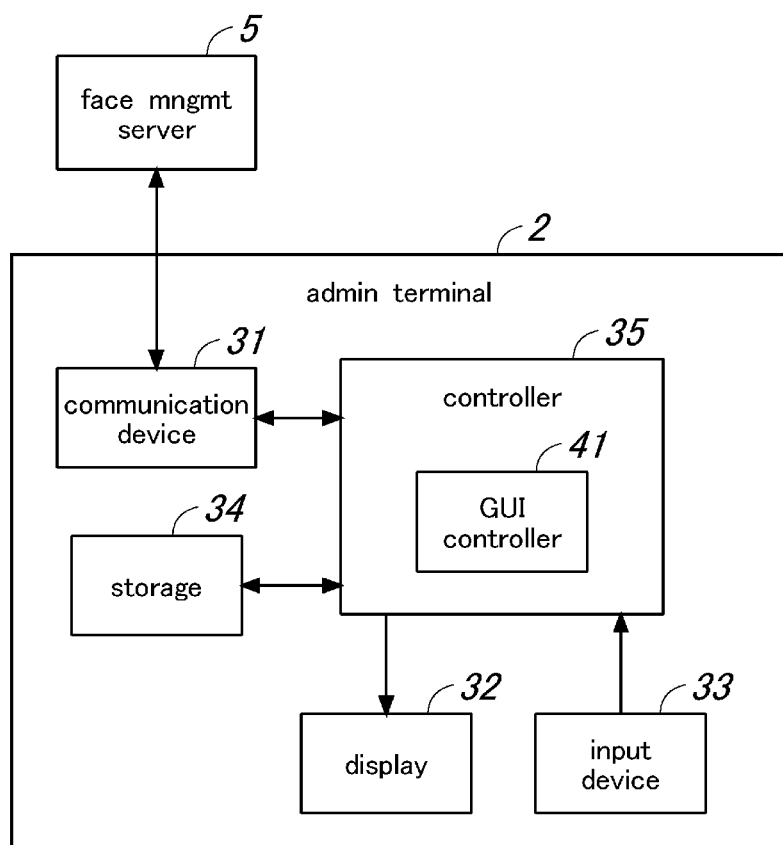
FIG. 6 is a block diagram showing a schematic configuration of an administrator terminal 2.

Next, an administrator terminal 2 will be described. FIG. 6 is a block diagram showing a schematic configuration of an administrator terminal 2.

The administrator terminal 2 includes a communication device 31, a display 32 (display device), an input device 33 (operation interface), a storage 34, and a controller 35.

The communication device 31 communicates with a face management server(s) 5 via the network. In the present embodiment, the communication device 31 receives screen information and other information from a face management server 5, and, in response, transmits information on an administrator's operation on the screen or other information to the face management server 5.

The display 32 displays various types of screens. The input device 33 may be a mouse, a keyboard, or other types of interface, and is used to operate the screen on the display 32.

The storage 34 stores programs (such as administrator terminal's application) to be executed by a processor, which implements the controller 35, or other information.

The controller 35 includes a GUI controller 41. The controller 35 is configured by the processor, and each part of the controller 35 is implemented by the processor executing a program (of the administrator terminal's application) stored in the storage 34.

The GUI controller 41 performs control to display various operation screens delivered from a face management server 5 on the display 32. In response to an input operation performed by an administrator using the input device 33, the GUI controller 41 acquires information entered by the administrator and controls screen display. In the present embodiment, the GUI controller 41 controls screen display and data entry related to log-in, i.e., a log-in screen and data entry therein. In addition, the GUI controller 41 controls screen display and data entry related to user management, i.e., screens for registration (individual registration, collective registration), view, update, and deletion of user data, and data entry therein. Furthermore, the GUI controller 41 controls screen display and data entry related to matching group management, i.e., screens for registration (individual registration, collective registration), view, update, and deletion of data of matching groups and data entry therein. In addition, the GUI controller 41 controls screen display and data entry related to face authentication machine management, i.e., screens for registration, view, update, and deletion of data of associations (hereinafter also simply referred to as "associations") between authentication machines and matching groups. The GUI controller 41 also controls screen display and data entry related to a view screen for viewing authentication logs.

Figure 7:
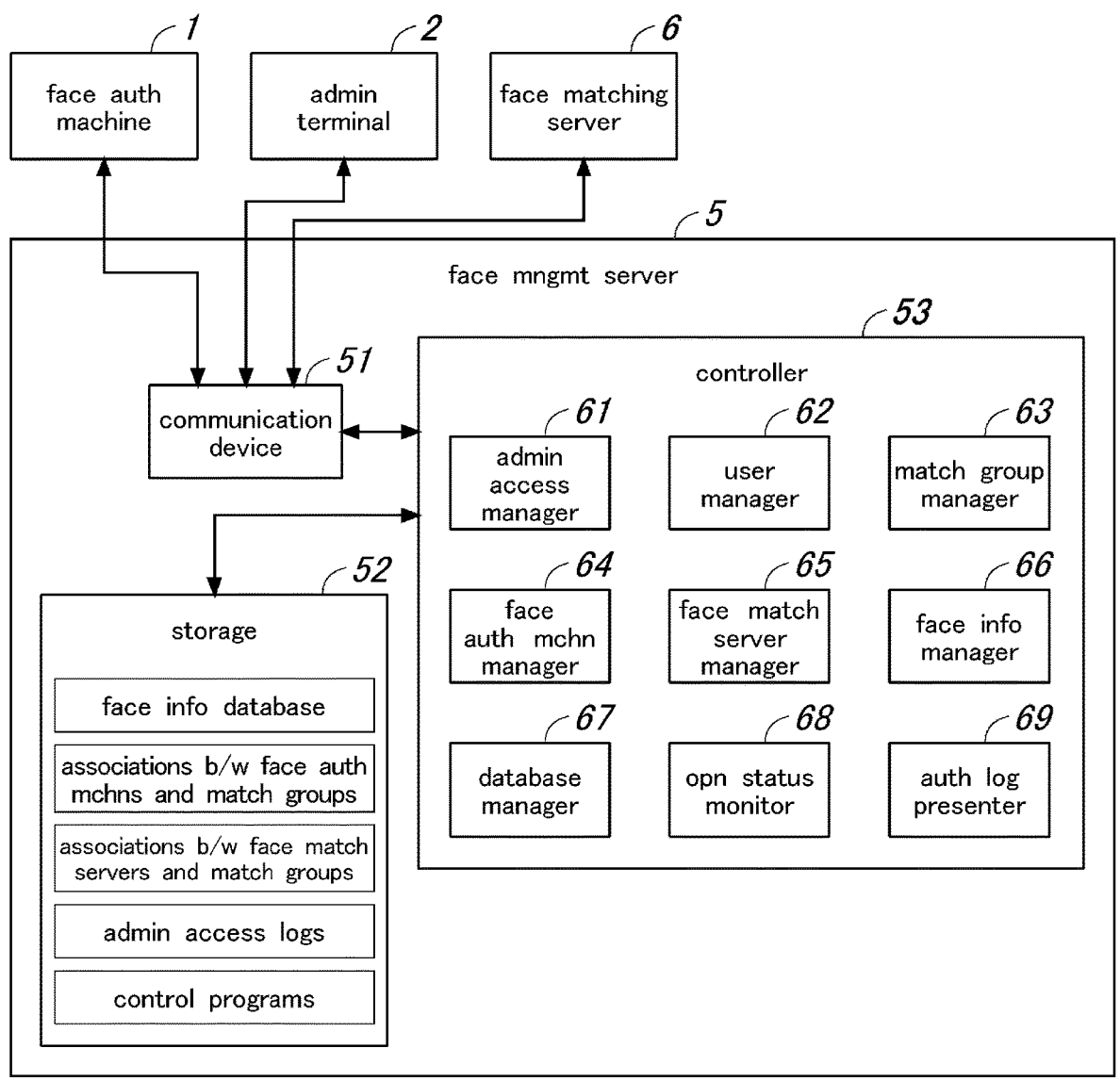
FIG. 7 is a block diagram showing a schematic configuration of a face management server 5.

Next, a schematic configuration of a face management server 5 will be described. FIG. 7 is a block diagram showing a schematic configuration of a face management server 5.

The face management server 5 includes a communication device 51, a storage 52, and a controller 53.

The communication device 51 communicates with an administrator terminal(s) 2 via the network. The communication device 51 communicates with a face authentication machine(s) 1 via the network. The communication device 51 communicates with a face matching server(s) 6.

The storage 52 stores a face information database, a database of associations between face authentication machines 1 and matching groups, a database of associations between face matching servers 6 and matching groups, administrator access logs, control programs executed by a processor that implements the controller 53, and other information.

The face information database contains user data of registered users such as first name, last name, face image, matching group of each user. Users' face images may be stored in an encrypted state for privacy protection.

The controller 53 includes an administrator access manager 61, a user manager 62, a matching group manager 63, a face authentication machine manager 64, a face matching server manager 65, a face information manager 66, a database manager 67, an operation status monitor 68, and an authentication log presenter 69. The controller 53 is configured by the processor, and each unit of the controller 53 is implemented by the processor executing a program stored in the storage 52. Each unit of the controller 53 is configured as a Web API (Web Application Programming Interface).

The administrator access manager 61 permits or denies the access (login) of an administrator who accesses the face management server from the administrator terminal 2 according to the permission group of the administrator.

In addition, the administrator access manager 61 is configured to manage accesses to the face management server from administrator terminals 2, and when an administrator operates the administrator terminal 2 to access the face management server, the administrator access manager 61 stores information about the access in the storage 52 as an administrator access log (history information). Moreover, in response to a request for viewing from an administrator terminal 2, the administrator access manager 61 presents the administrator access log to the administrator terminal 2.

The user manager 62 manages data of users and performs necessary operations regarding user data in response to a request from an administrator terminal 2. In the present embodiment, when an administrator terminal 2 makes a request for registration, view, update, or deletion of user data, the user manager 62 performs necessary operations in response to the request.

The matching group manager 63 manages information about matching groups, and performs necessary operations regarding matching groups in response to a request from an administrator terminal 2. In the present embodiment, when an administrator terminal 2 makes a request for registration, view, update, or deletion of data regarding a matching group, the matching group manager 63 performs necessary operations in response to the request. Furthermore, the matching group manager 63 generates matching group information for each face authentication machine 1 (i.e., information required for the face authentication machine 1 to transmit a request for face matching to a face matching server 6 of the same matching group), and provides the matching group information to the face authentication machine 1.

The face authentication machine manager 64 manages information about face authentication machines 1 and performs necessary operations related to face authentication machines 1 in response to a request from an administrator terminal 2. In the present embodiment, when an administrator terminal 2 makes a request for registration, view, update, or deletion of data regarding associations between face authentication machines 1 and matching groups, the face authentication machine manager 64 performs necessary operations in response to the request.

The face matching server manager 65 manages information about face matching servers 6, and performs necessary operations related to face matching servers 6 in response to a request from an administrator terminal 2. In the present embodiment, when an administrator terminal 2 makes a request for registration, view, update, or deletion of data regarding associations between face matching servers 6 and matching groups, the face matching server manager 65 performs necessary operations in response to the request.

The face information manager 66 manages users' face information stored in the face management server and a face matching server(s) 6, respectively. In the present embodiment, the face information manager 66 synchronizes face information in these servers such that users' face information stored in the face management server (such as each user's first name, last name, and face image) and that stored in a face matching server(s) 6 (each user's face feature amount data) are consistent with each other. Furthermore, the face information manager 66 makes copies of face information (users' face feature amount data) from one storage to another.

The database manager 67 manages databases in the face management server 5, and backs up and restores the databases.

The operation status monitor 68 monitors the operation status of the face management server 5, and also receives notifications of the operation statuses from face authentication machines 1 and face matching servers 6. Moreover, in response to an administrator's operation on the administrator terminal 2, the operation status monitor 68 displays the operation statuses of a face authentication machine(s) 1, the face management server (face management server 5), and a face matching server(s) 6 on the screen of the administrator terminal 2.

The authentication log presenter 69 acquires an authentication log from a face matching server 6 in response to a request for viewing from an administrator terminal 2, and presents the authentication log to the administrator terminal 2.

Figure 8:
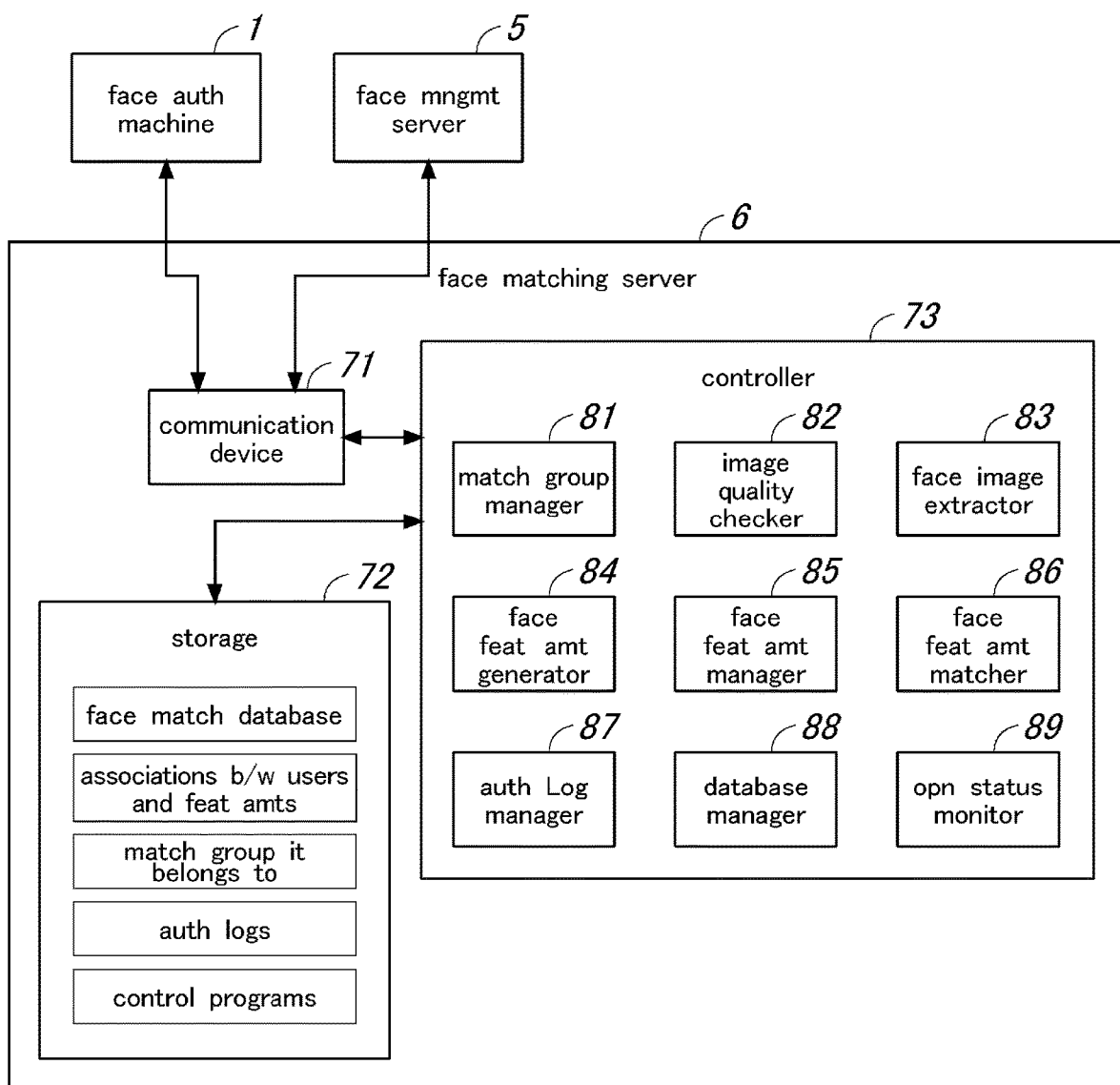
FIG. 8 is a block diagram showing a schematic configuration of a face matching server 6.

Next, a schematic configuration of a face matching server 6 will be described. FIG. 8 is a block diagram showing a schematic configuration of a face matching server 6.

The face matching server 6 includes a communication device 71, a storage 72, and a controller 73.

The communication device 71 (face image receiver, authentication result transmitter) communicates with a face authentication machine(s) 1 via a network. In the present embodiment, the communication device 71 receives face image data and other information from a face authentication machine(s) 1. The communication device 71 transmits a user's authentication result and other information to a face authentication machine(s) 1. In addition, the communication device 71 communicates with a face management server(s) 5 via the network. In the present embodiment, the communication device 71 receives requests for various processing operations from a face management server 5 and transmits a response to each request to the face management server 5.

The storage 72 stores a face matching database, information about an association between each user and a corresponding feature amount, information about a matching group of each face matching server, authentication logs, control programs executed by a processor which implements the controller 73, and other information.

A face matching database contains user face feature amount data and other data as data of registered users. Face matching databases are separately provided for different matching groups, and thus users' face feature amount data is stored for each matching group. In case of unexpected loss of data from a face matching database, the face feature amount data of registered users may be backed up and saved in a non-volatile memory such as an HDD or SSD mounted in the face matching server 6.

The controller 73 includes a matching group manager 81, an image quality checker 82, a face image extractor 83, a face feature amount generator 84, a face feature amount manager 85, a face feature amount matcher 86, an authentication Log manager 87, a database manager 88, and an operation status monitor 89. The controller 73 is configured by the processor, and each unit of the controller 73 is implemented by the processor executing a program stored in the storage 72. Each unit of the controller 73 is configured as a Web API (Web Application Programming Interface).

The matching group manager 81 manages the matching group to which the face matching server 6 belongs, and performs operations for the registration or deletion of data regarding matching groups in response to a request from a face management server 5.

The image quality checker 82 determines whether or not the image of a face region in the shot image satisfies a predetermined quality level. Specifically, the image quality checker 82 detects whether or not a person to be verified in the image wears a mask, and whether or not the person wears sunglasses, and calculates the degree of face authentication suitability (an evaluation value based on face orientation and facial expression).

Upon user registration, the face image extractor 83 extracts a face image from a shot image of a user acquired from an administrator terminal 2. Specifically, the face image extractor 83 detects a person's face from the shot image (face detection); determines whether or not the detected face size is appropriate (face size check); and cuts out a face region from the shot image (face cut-out) to thereby acquire the face image data of the person. In other embodiments, the face image extractor 83 may extract a face image from a shot image of a person to be verified acquired from a face authentication machine 1 when a face authentication process is performed.

The face feature amount generator 84 detects face feature points from face image data and generates face feature amount data at times of user registration and a face authentication process Upon user registration, the face feature amount manager 85 registers face feature amount data of a user generated by the face feature amount generator 84 in the face matching database of the matching group of the user. The face feature amount manager 85 deletes face feature amount data registered in a face matching database in response to a request from the face management server 5 when the data is updated or deleted. Furthermore, when the version of a program related to face feature amount generation or face matching algorithm is upgraded, in response to a request from a face management server 5, the face feature amount manager 85 updates face feature amount data registered in a face matching database such that the face feature amount data can be used in the new program.

During a face authentication process, the face feature amount matcher 86 determines whether or not a person to be verified is a registrant by comparing the face feature amount data of the person generated from face image data acquired from the face authentication machine 1, with the face feature amount data of registrants (registered users) stored in the face matching server 6. A face feature amount matchers 86 is provided for a matching group associated with the face matching server 6. When a plurality of matching groups are associated with the face matching server 6, individual face feature amount matchers 86 are provided for different matching groups. Each face feature amount matcher 86 (face matching process) in combination with a corresponding face matching database forms a face matching unit.

Moreover, a face feature amount matcher 86 calculates the degree of similarity (matching score) between a person to be verified and registrant data. The face feature amount matcher 86 can compare the calculated similarity with a predetermined threshold value to determine whether or not the person to be verified can be authenticated; that is, whether a face authentication result for the person is a success or a failure. The face feature amount matcher 86 notifies the face authentication machine 1 of the face authentication result as a matching result. A face feature amount matcher 86 may notify a face authentication machine of, in addition to a face authentication result, a list of registrants having high degrees of similarity with a person to be verified along with the registrants' personal IDs and degrees of similarity.

When a face authentication machine 1 makes a request for face authentication to the face matching server 6, the authentication log manager 87 stores and accumulates information about the request (i.e., the device ID of the face authentication machine 1 making the request, a face matching result, and other information) in the storage 72 as an authentication log. In addition, the authentication log manager 87 provides authentication logs to a face management server 5 in response to a request from the face management server 5.

The database manager 88 manages databases in the face matching server 6, and backs up and restores the databases.

The operation status monitor 89 monitors the operation status of the face matching server 6 and notifies a face management server 5 of the operation status of the face matching server 6.

In the present embodiment, the primary functions of a face matching server 6 include face image extraction, face feature amount generation, and face feature amount matching, and the respective functions may be implemented by different information processing devices operating independently from one another. For example, the face image extraction function may be implemented by a separate information processing device operating independently from the other device(s) which implements the functions of face feature amount generation and face feature amount matching.

Figure 9:
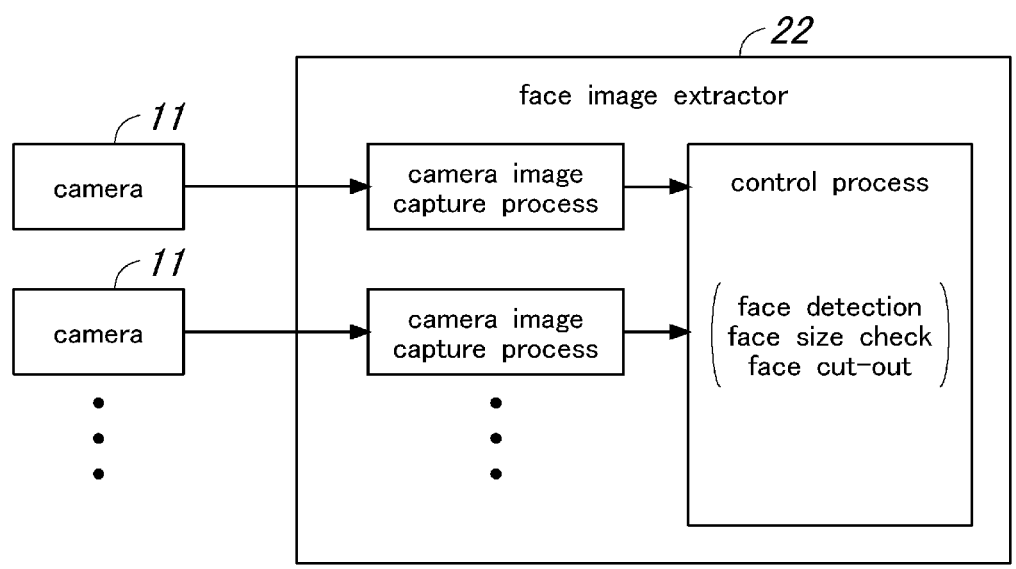
FIG. 9 is an explanatory diagram showing an outline of operations for face image extraction performed by a face authentication machine 1.

Next, operations performed by the face image extractor 22 of a face authentication machine 1 during a face authentication process will be described. FIG. 9 is an explanatory diagram showing an outline of operations performed by the face image extractor 22 of a face authentication machine 1.

The face authentication machine 1 may be provided with a plurality of cameras 11. In this case, a camera image capture process (functional unit) is provided for each camera 11 to acquire shot images from the camera. When starting up, the face authentication machine 1 activates each camera image capture process, which transfer shot images acquired from the camera 11 to a control process (functional unit). The control process performs the operations of face detection, face size check, and face cut-out on the captured images from the respective cameras 11.

In a face authentication machine 1, the control process reads a setting file including information on the settings of the respective cameras, and causes the camera image capture processes to operate based on the information of the settings. In operation, each camera image capture process receives parameters from the control process, the parameters including camera type, camera connection information, image acquisition rate, and acquired image size.

In the face detection operation, the control process detects a face region included in a captured image from a camera 11.

The control process determines a face frame (a rectangular frame surrounding the face region) based on the detection result.

An image shot by a camera 11 may include a plurality of face regions. In this case, the control process selects one face region to be verified from the detected face regions (face region selection operation). Although, in the present embodiment, the control process selects only one face region to be verified, the control process may select two or more face regions to be verified. In the latter case, an administrator may designate the number of face regions to be selected.

In the face region selection operation, the control process may select the face region to be verified based on the size (area) of a face frame. Specifically, the control process may calculate the area of each face frame from the width and height thereof, compare the areas between different face frames, and select a predetermined number of face regions in descending order of area. When selecting only one face region, the control process may select the face region having the largest area. When two or more face frames have the same area, the control process may select the face region(s) in the order of detection.

The control process may select the face region to be verified based on the width of a face frame. Specifically, the control process may compare the widths between different face frames, and select a predetermined number of face regions in descending order of width. When selecting only one face region, the control process may select the face region having the largest width. When two or more face frames have the same width, the control process may select the face region(s) in the order of detection.

Prior to face detection, the face authentication machine 1 can perform a preliminary operation such as grayscale conversion.

In the face size check operation, the control process determines whether or not the size of a face region (face frame) detected from a captured image falls within a predetermined range (appropriate range). When the width and height of a face frame acquired by face detection are within predetermined ranges, respectively, the control process determines that the size of the face region is suitable. More specifically, respective thresholds (minimum and maximum values) are preset for the width and height, and the control process compares the width and height of a face frame with the respective minimum and maximum values. The control process determines that the size of a face region is suitable when the width is greater than or equal to its minimum value and less than or equal to its maximum value, and the height is greater than or equal to its minimum value and less than or equal to its maximum value.

FIGS. 10 and 11 are explanatory diagrams showing an outline of a face cut-out operation performed by a face authentication machine 1.

In the face cut-out operation, the control process determines the cut-out region for an image captured by a camera based on the face region (face frame) acquired by face detection operation. The control process cuts out an image of the cut-out region (face cut-out frame) as a face image. The control process determines a cut-out region around a face region as a region extending beyond the face region in the vertical and horizontal directions.

Figure 10A:
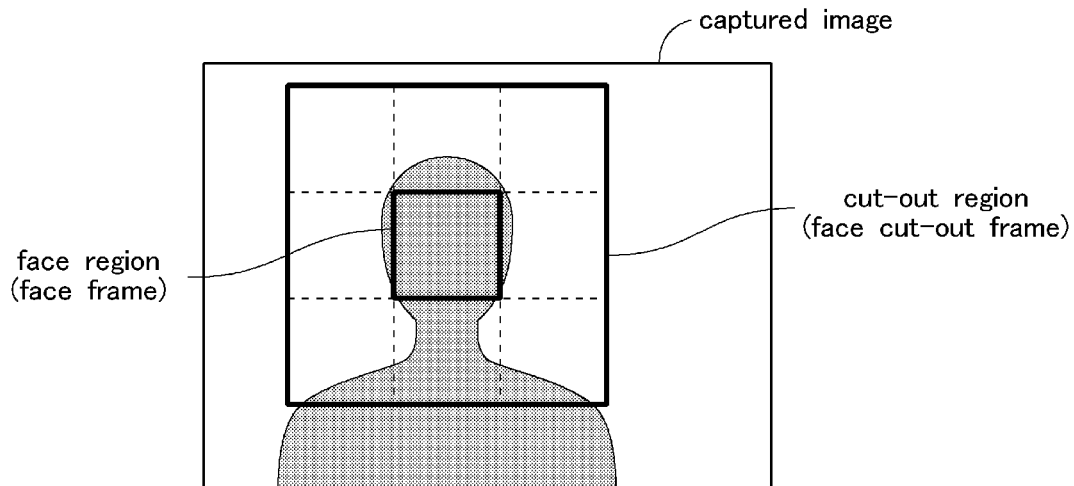
FIGS. 10A-B are explanatory diagrams showing outlines of a face cut-out operation performed by a face authentication machine 1.

In the example shown in FIG. 10A, the extension coefficient k is 3, and the cut-out region is determined as a region three times as large as the face region detected by the face detection operation. In the example shown in FIG. 10B, the extension coefficient k is 4, and the cut-out region is determined as a region four times as large as the face region.

Figure 10B:
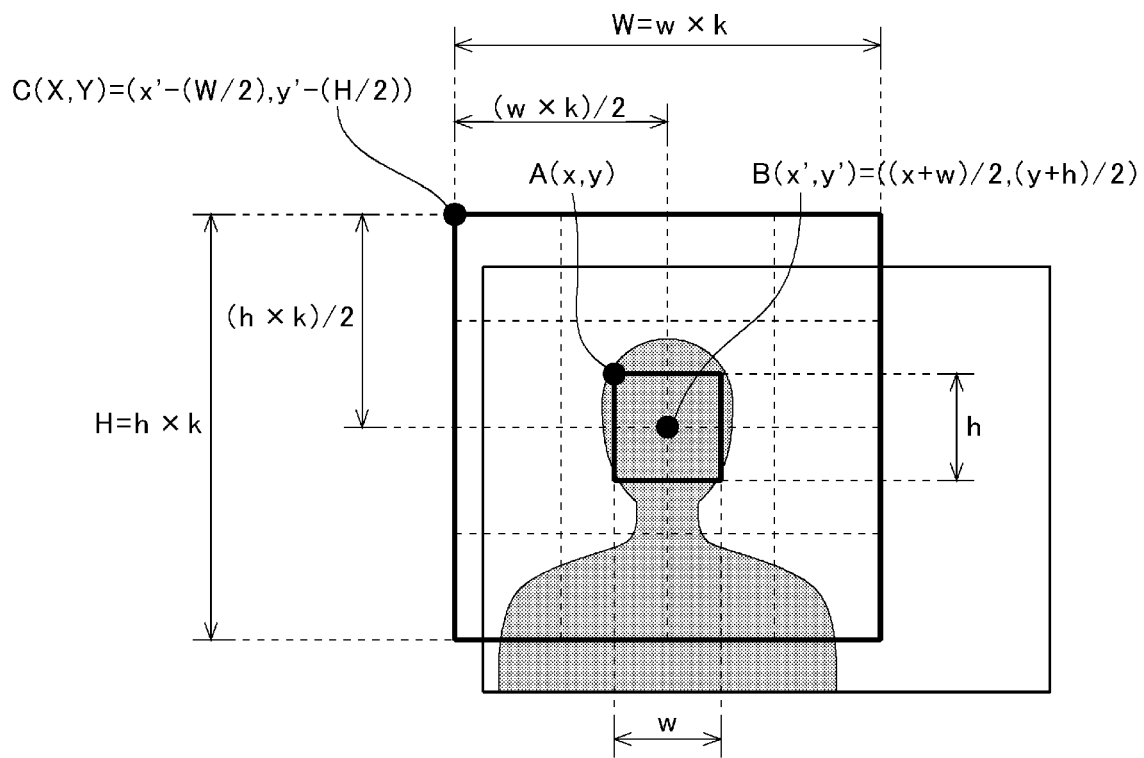

As shown in FIG. 10B, the coordinates (x', y') of the center point B of the face frame are calculated as the following equation.

$$(x',y')=((x+w)/2,(y+h)/2)$$

where (x, y) are the coordinates of the upper left vertex A of the face frame, and w and h are the width and height of the face frame.

The width W and height H of the cut-out region are calculated by the following equations.

$$W=w\times k$$

$$H=h\times k$$

where w and h are the width and height of the face frame and k is the extension coefficient. The coordinates (X, Y) of the upper left vertex C of the cut-out region are given by the following equation.

$$(X,Y)=(x'-(W/2),y'-(H/2))$$

where (x', y') are the coordinates of the center point B of the face frame, and W and H are the width and the height of the cut-out region.

The cut-out region is defined by the coordinates (X, Y) of the upper left vertex C, the width W and the height H thereof.

Figure 11A:
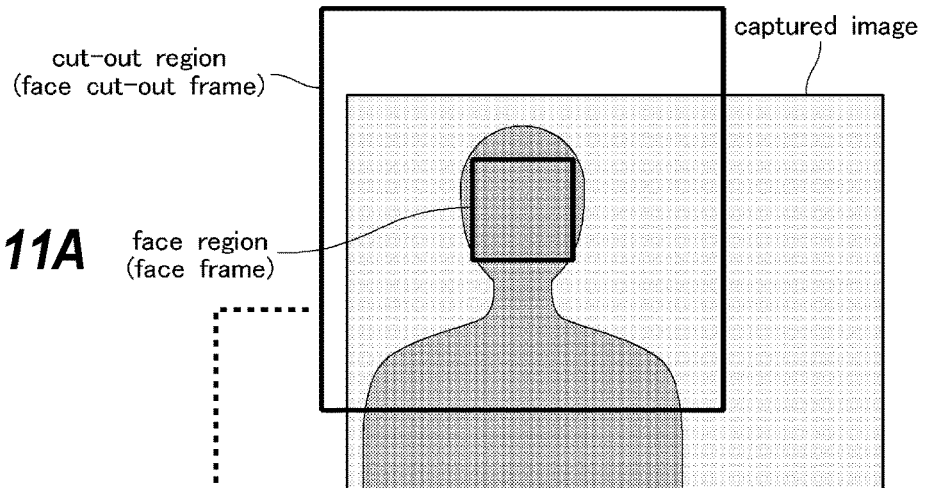
FIGS. 11A-D are explanatory diagrams showing outlines of the face cut-out operation performed by a face authentication machine 1.

The cut-out region can be determined without any further process when a captured image contains the entire cut-out region. However, as shown in FIG. 11A, a captured image does not always include the entire cut-out region (i.e., part of the cut-out region extends beyond a captured image).

Figure 11B:
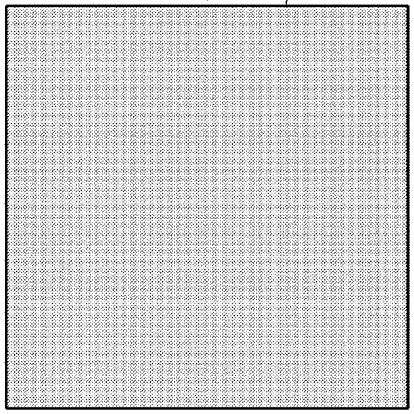
Figure 11C:
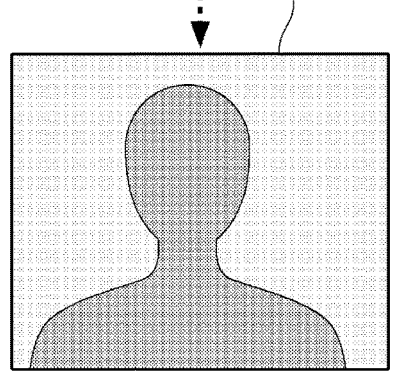
Figure 11D:
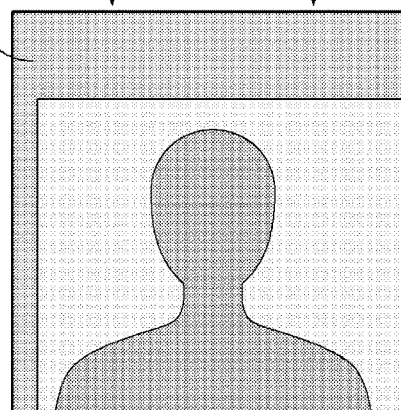

In this case, as shown in FIG. 11B, the control process produces a background image of the same size as the cut-out region. The background image fills the margins or regions extending beyond the captured image, and is filled with a predetermined color (e.g., black). Moreover, as shown in FIG. 11C, the control process acquires a cut-out image by cutting out an image of part of the cut-out region in the shot image. Then, as shown in FIG. 11D, the control process superimposes the cut-out image on the background image to generate a face image.

Figure 12:
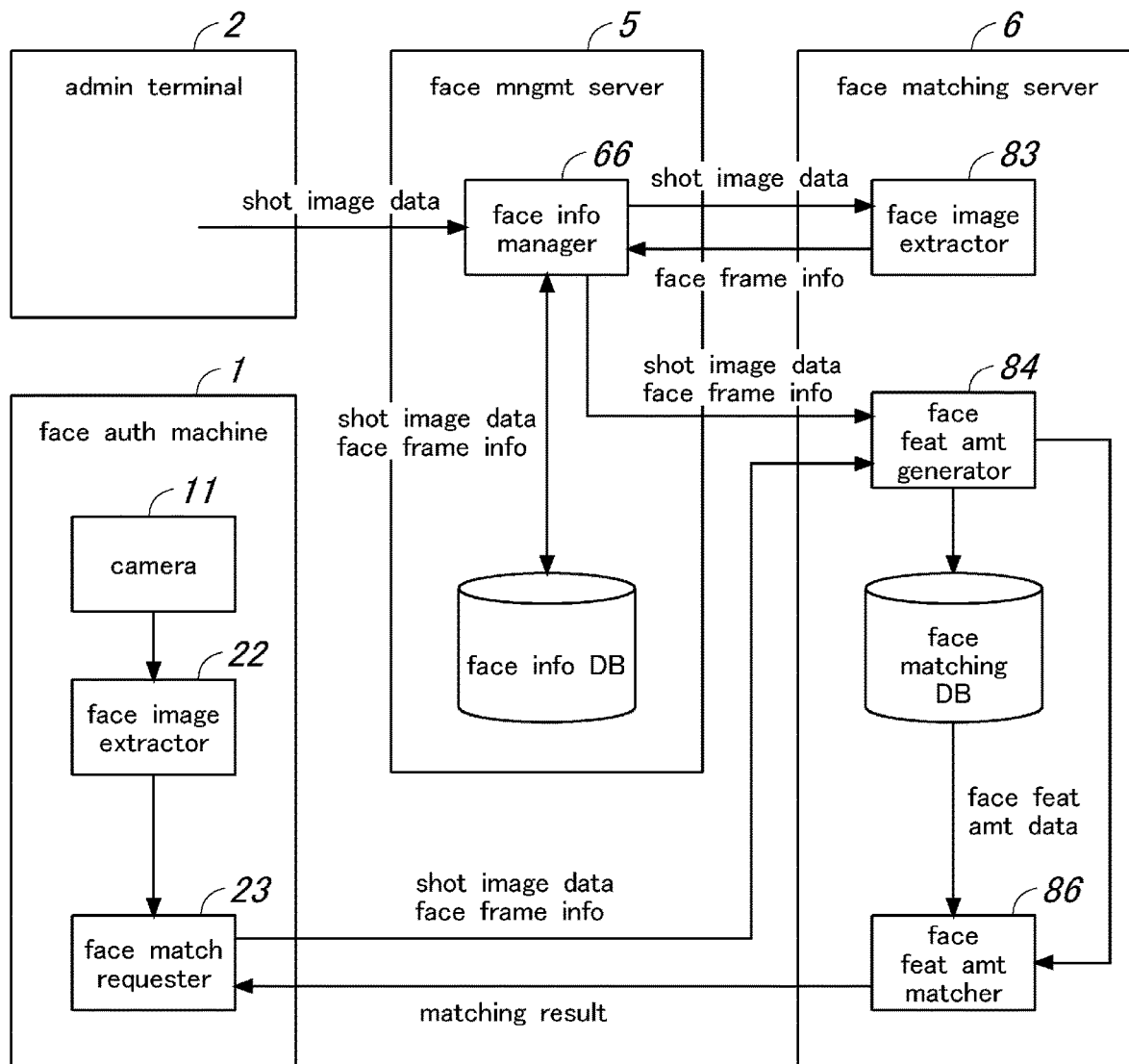
FIG. 12 is an explanatory diagram showing an outline of operations for face image extraction.

Next, operations for face image extraction will be described. FIG. 12 is an explanatory diagram showing an outline of operations for face image extraction.

As described above, the face image extractor 22 of a face authentication machine 1 performs operations for face image extraction; that is, the operations of face detection, face size check, and face cut-out to thereby generate face image data from a user's shot image. The face image extractor 83 of a face matching server 6 also performs the same operations for face image extraction in a similar manner.

Upon user registration, an administrator terminal 2 transmits data of a shot image of a user to a face matching server 6 via a face management server 5, and then the face image extractor 83 of the face matching server 6 performs operations for face image extraction.

At the time of face authentication, only a face authentication machine 1 performs operations for face image extraction, and a face matching server 6 does not perform the operations for face image extraction. As such, a face authentication machine 1 is configured to have a highly accurate face detection capability. In a face authentication machine 1, each camera 11 constantly shoots images of a corresponding shooting area, and upon detecting a face, the face authentication machine 1 transmits face image information (captured image data and face frame information) to a face matching server 6. As a result, the computational load of the operations for face image extraction is distributed to a plurality of face authentication machines 1, thereby reducing the load on a face matching server(s) 6. Moreover, this configuration can reduce the amount of communications, thereby decreasing the load on the network. Furthermore, since this configuration allows for quick face authentication responses, even when persons to be verified appear in succession, the system can efficiently perform face authentication processes for the persons.

In this way, the face authentication system is configured to share the operational load of a face authentication process between a face authentication machine 1 and a face matching server 6, thereby eliminating the need of providing a number of expensive face authentication machines capable of performing all the operations for face authentication, as in the prior art. In addition, even when the update of face feature amount data occurs, there is no need for a large-scale maintenance work on face authentication machines, and the adaptation of a face matching server 6 is sufficient to make the new data usable. Therefore, according to the present embodiment, a face authentication system can be implemented at a lower cost and configured to require less maintenance work.

In some cases, an administrator terminal 2 may be configured without a function of face image extraction: that is, an administrator terminal 2 may be configured without a face image extractor 22.

Figure 13:
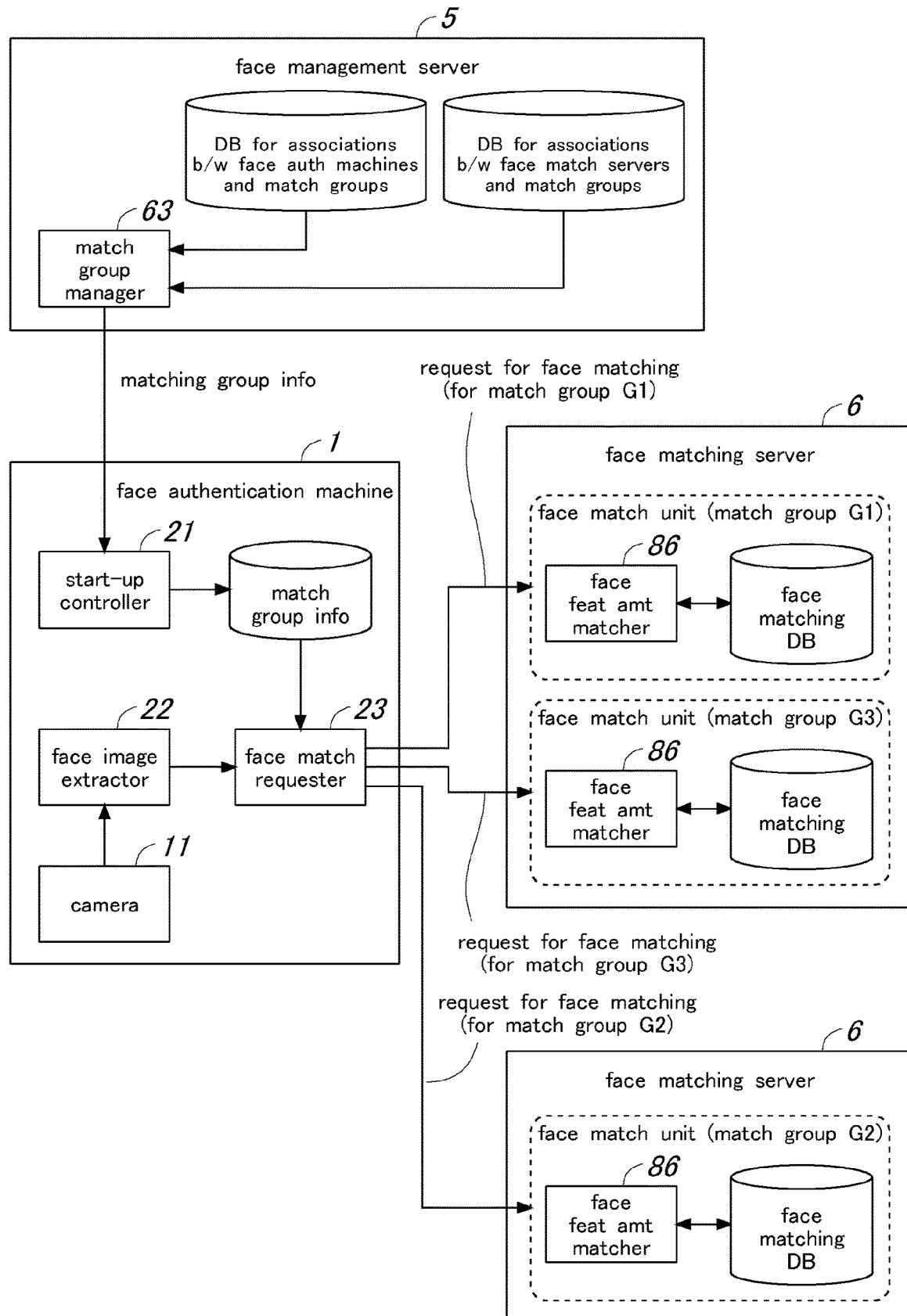
FIG. 13 is an explanatory diagram showing an outline of face matching inquiry operations using matching group information.

FIG. 13 is an explanatory diagram showing an outline of face matching inquiry operations using matching group information.

A face management server 5 stores matching group information about matching groups of users, data of associations between face authentication machines 1 and matching groups, and data of associations between face matching servers 6 and matching groups. The matching group manager 63 of a face management server 5 generates matching group information for each face authentication machine 1 based on the data of associations between face authentication machines 1 and matching groups and the data of associations between face matching servers 6 and matching groups.

The matching group information is required for a face authentication machine 1 to transmit a request for face matching to the face matching server(s) 6 of the same matching group as the face authentication machine 1. The matching group information includes ID information (group number) of the matching groups of the face authentication machine 1, and destination data of the face matching server 6 to which the face authentication machine 1 makes a request (i.e., the face matching server 6 of the same matching group as the face authentication machine 1). Specifically, the destination data is the network address (e.g. IP address) of the face matching server 6. The destination data is used to identify the face matching server 6 to which a face authentication machine transmits a request for face matching, and to associate the face authentication machine 1 with the face matching server(s) 6 to which the face authentication machine 1 can make a request. When a face authentication machine 1 belongs to a plurality of matching groups, the addresses (IP addresses) of the respective face matching servers 6 of the matching groups are included in the matching group information.

In a face authentication machine 1, at the time of starting up or other timing, the start-up controller 21 acquires matching group information from a face management server 5 as operation setting information and stores the information in the face authentication machine 1. When detecting the face of a person, the face authentication machine 1 transmits a request for face matching to the face matching server 6 of the same matching group as the face authentication machine. The request for face matching includes information on the matching group of the face authentication machine and other information.

A face authentication machine 1 may acquire setting information about matching groups from a face management server 5 at the time of starting up, at a predetermined time, or an regular intervals. In other embodiments, the face management server 5 may deliver matching group information to a face authentication machine(s) 1.

A face matching server 6 stores data of associations between face matching processes of the face matching server 6 and matching groups. Upon receiving a request for face matching from a face authentication machine 1, the face matching server 6 identifies the face matching process corresponding to the face authentication machine 1 based on the data of association between the matching group and the face authentication process and the matching group information acquired from the face authentication machine 1, thereby causing the identified face matching process to execute a face matching operation. In this way, the face matching process for the matching group of a face authentication machine performs a face matching operation.

In the present embodiment, a face matching server 6 includes individual face matching databases for different face matching groups, and stores face feature amount data of each matching group in a corresponding matching database. Thus, upon receiving a request for face matching, the face matching server 6 performs a face matching operation on the face feature amount data registered in the database of the matching group of the face authentication machine 1. In other embodiments, a face matching server 6 may first perform a face matching operation on face feature amount data regardless of the matching group of a face authentication machine 1, and then perform a filtering operation on the face matching result. In other words, the face matching server 6 may first perform a face matching operation on the stored face feature amount data of the all users, and then extract face matching results regarding the users who belongs to the same matching group as the face authentication machine 1. In this case, face matching databases may not be provided separately for different matching group.

Next, administrator access management will be described.

The system of the present embodiment manages access from an administrator terminal 2 to a face management server(s) 5 and a face matching server(s) 6. A face management server 5 includes the administrator access manager 61. The administrator access manager 61 monitors the status of access (login) from an administrator terminal 2 to the face management server 5 and the face matching server 6. When detecting an access from an administrator terminal 2, the administrator access manager 61 records information about the access (such as accessing administrator, accession date and time) as an administrator access log (history information). Furthermore, the face management server 5 provides the administrator access logs to the administrator terminal 2 in response to a request for viewing administrator access logs from the administrator terminal 2, thereby enabling an administrator to view the administrator access logs.

In the system of the present embodiment, access rights to user information are set and granted to some administrators to restrict access to user information (for registering, viewing, updating and deleting user data). Administrators are grouped into multiple administrator groups based on the types of access rights granted to them. For example, administrators are grouped into the groups of system operation administrators, service operation administrators, and general administrators.

In the present embodiment, users are grouped into a plurality of permission groups according to the administrator group with access to user information. Each permission group of users corresponds to an administrator group with access to data of the users. In the present embodiment, users are grouped into the groups of system operation users, service operation users, and general users.

When detecting a login from an administrator, the face management server 5 acquires the administrator group (administrator type) of the logged-in administrator, and determines whether or not to allow the administrator to access data of a user (for viewing, updating, and deleting the data) based on its administrator group and the permission group to which the user belongs, and permits the administrator to the user data based on the determination result. In other words, the face management server 5 allows the logged-in administrator to view, update, and delete only user data to which the administrator group of the administrator is permitted to access.

A system operation administrator is a person who manages the operation of the system (such as maintenance), and is permitted to access the data of all users; that is, users who belong to permission groups of system users, administration users, or general users. A service operation administrator is a person who manages operations related to face authentication services (such as user registration/deletion) provided by the system, and is permitted to access the data of users who belong to permission groups of administration users or general users. A general administrator is a person authorized by a service operation administrator, and is permitted to access only the data of users who belong to a permission group of general users.

Figure 14:
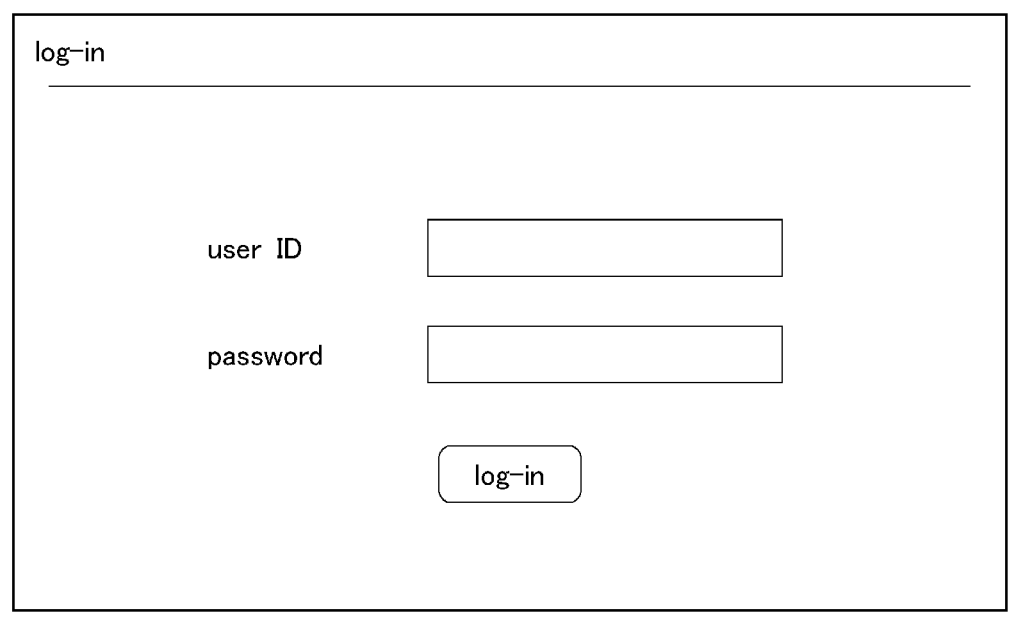

FIG. 14 is an explanatory diagram showing a login screen displayed on an administrator terminal 2.

Upon the activation of the administrator application, an administrator terminal 2 accesses a face management server 5, and displays a login screen. An administrator can operate the login screen to enter the administrator's user ID and password. When the administrator enters the user ID and password on this login screen and operates the login button, the face management server 5 performs operations for user authentication. When the administrator successfully logs in, the administrator terminal 2 displays the top screen. When the administrator fails to log in, the administrator terminal 2 displays an error screen.

Next, operations for registering, viewing, updating and deleting data of matching groups will be described. FIGS. 15A-C and 16 are explanatory diagrams showing screens displayed on the administrator terminal 2 when data of matching groups is to be registered, viewed, updated, and deleted.

Figure 15A:
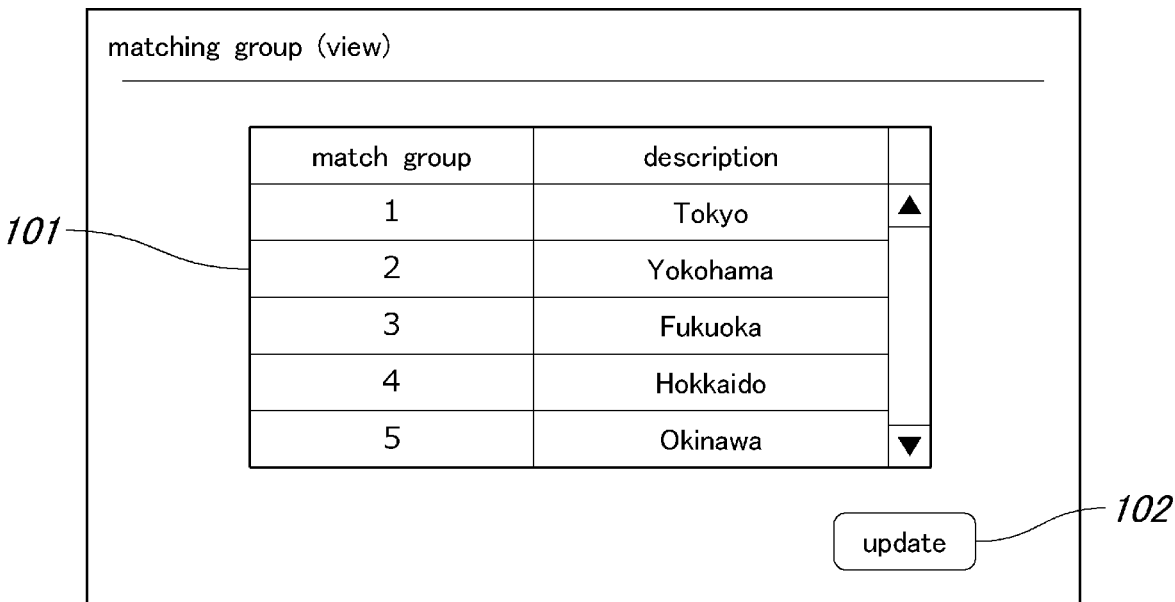
FIGS. 15A-C are explanatory diagrams showing screens displayed on the administrator terminal 2 when data of a matching group is to be registered, viewed, and updated.
Figure 15B:
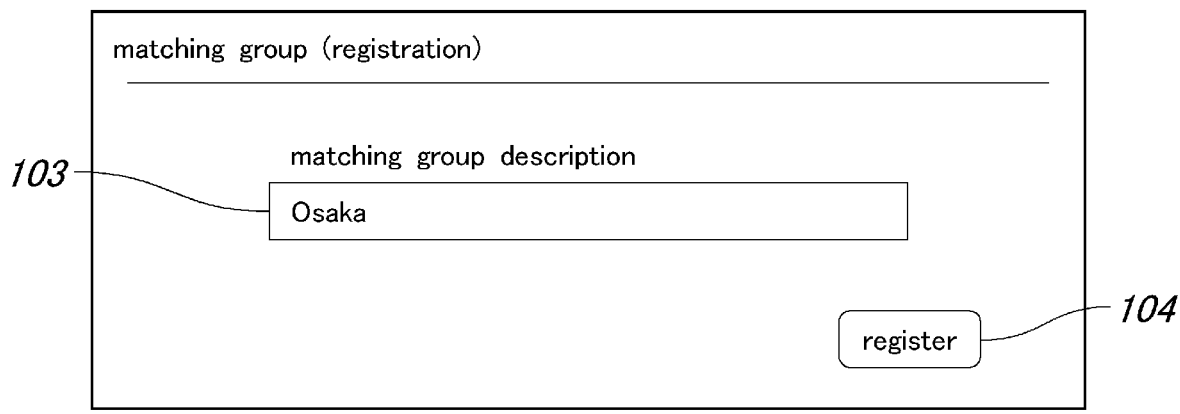
Figure 15C:
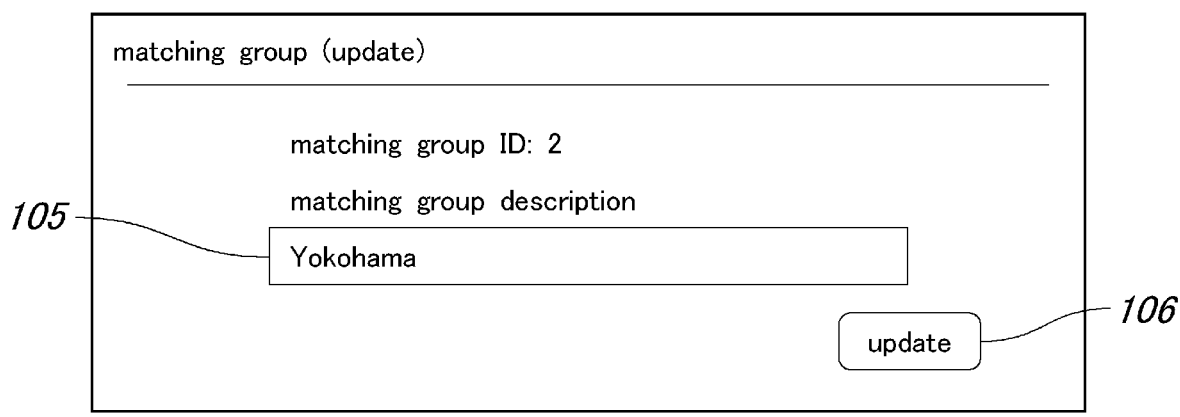

For the operations for registering, viewing, updating and deleting data of matching groups, an administrator terminal 2 displays a view screen shown in FIG. 15A, a registration screen shown in FIG. 15B, an update screen shown in FIG. 15C, and a deletion screen shown in FIG. 16.

The view screen shown in FIG. 15A displays a list of registered matching groups. An administrator can check the registered data of matching groups displayed on the view screen.

The view screen includes a list display section 101 and an update button 102. The list display section 101 displays matching group IDs (numbers) and corresponding descriptions (installation locations) about the matching groups for registered matching groups. This allows an administrator to check the registered matching groups. When an administrator operates the update button 102 on the view screen, the list display section 101 is updated to indicate the latest registered data. Furthermore, when the administrator selects a matching group by operating its matching group ID, the screen transitions to the update screen (see FIG. 15C).

An administrator can designate an item (matching group, description) on the view screen to thereby perform a sort operation. In some cases, an administrator can designate the number of items displayed in the list display section 101 (the number of face matching servers 6), the ranges of face matching servers 6 and matching groups to be indicated on the view screen. Furthermore, the system may be configured to allow an administrator to designate search conditions for respective items (apparatus ID, face matching server 6, description) on the view screen to thereby perform a search operation.

The registration screen (first screen) shown in FIG. 15B allows an administrator to register a matching group.

The registration screen includes a description input section 103 and a registration button 104. An administrator can enter a description about a matching group in the description input section 103. When an administrator operates the registration button 104 after entering description, the face management server 5 performs an operation for registering matching group information including the entered description in the databases.

The update screen shown in FIG. 15C allows an administrator to update data of a matching group.

The update screen includes a description input section 105 and an update button 106. An administrator can enter a description about a matching group in the description input section 105. When an administrator operates the update button 106 after entering description, the face management server 5 performs an operation for updating matching group information in the databases with the entered description.

The deletion screen shown in FIG. 16 allows an administrator to delete data of a matching group.

The deletion screen includes a list display section 107 and a deletion button 108. The list display section 107 displays matching group IDs (numbers) and the corresponding descriptions (installation locations) for the registered matching groups. The list display section 107 includes a check box for each matching group. This allows an administrator to select one or more registered matching groups. When an administrator marks one or more checkboxes to select matching groups to be deleted and operates the deletion button 108, the face management server 5 performs a deletion operation to delete data of the selected matching groups.

Then, when the administrator selects "view" in the menu screen (not shown), the screen transitions to the view screen shown in FIG. 15A. When the administrator selects "registration" in the menu screen, the screen transitions to the registration screen shown in FIG. 15B. When the administrator selects "update" in the menu screen, the screen transitions to the update screen shown in FIG. 15C. When the administrator selects "deletion" in the menu screen, the screen transitions to the deletion screen shown in FIG. 16.

Figure 17A:
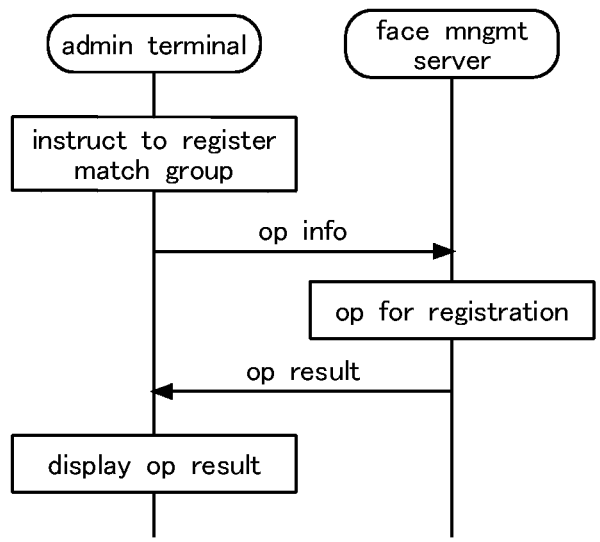
FIGS. 17A-C are sequence diagrams showing operation procedures of operations for registering, viewing, and updating data of a matching group.
Figure 17B:
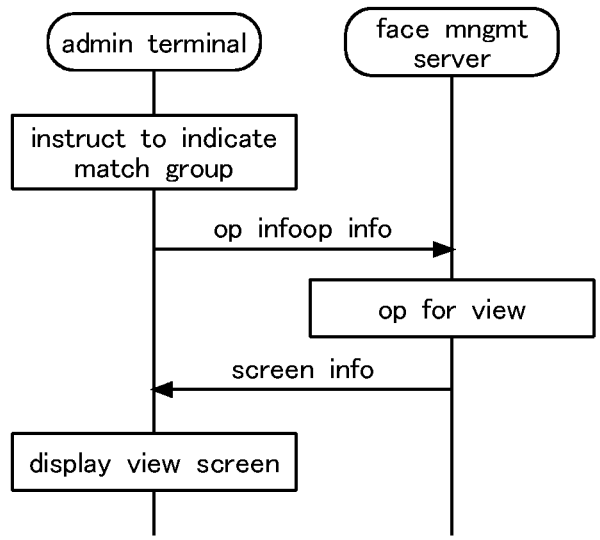
Figure 17C:
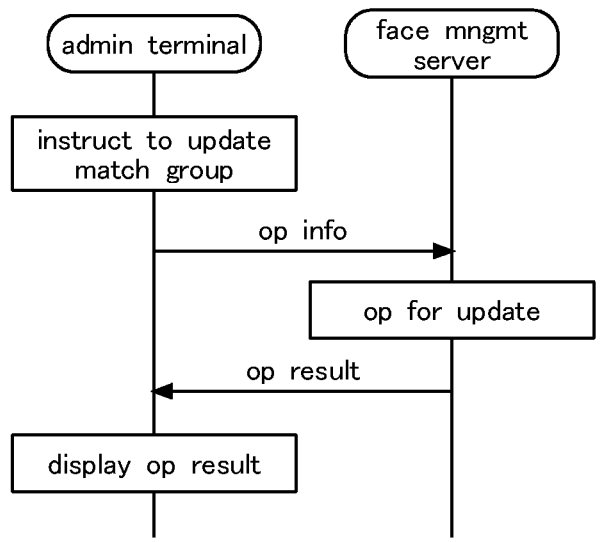
Figure 18:
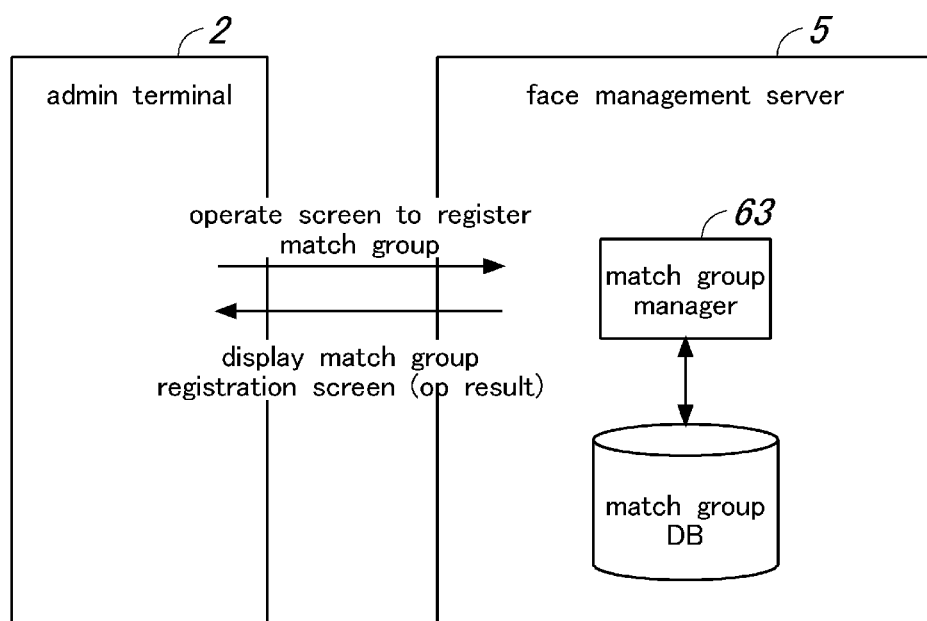
FIG. 18 is an explanatory diagram showing an outline of operations for registering, viewing, and updating data of a matching group.

Next, operations for registering, viewing, updating and deleting data of matching groups will be described. FIGS. 17A-C are sequence diagrams showing operation procedures of operations for registering, viewing, and updating data of a matching group. FIG. 18 is an explanatory diagram showing an outline of operations for registering, viewing, and updating data of a matching group.

First, the operations for registering data of a matching group in the system will be described.

As shown in FIG. 17A, an administrator operates an administrator terminal 2, instructing the system to perform the operations for registering data of a matching group. In the present embodiment, an administrator operates on the registration screen (FIG. 15B) to register data of a matching group.

As shown in FIG. 18, when the administrator operates the administrator terminal 2, instructing the system to perform the operations for registering data of a matching group, the matching group manager 63 in a face management server 5 performs a registration operation for registering data of the matching group entered by the administrator in a database of matching groups.

When the registration operation for registering data of the matching group is completed, the face management server 5 causes the administrator terminal 2 to display on the screen an operation result indicating whether or not the registration operation has been normally completed. In addition, the administrator access manager 61 in the face management server 5 records an administrator access log.

Next, the operations for viewing data of matching groups will be described.

As shown in FIG. 17B, an administrator operates an administrator terminal 2, instructing the system to perform the operations for viewing data of matching groups. In the present embodiment, an administrator operates on the menu screen to open the view screen for viewing data of matching groups (FIG. 15A).

When the administrator operates the administrator terminal 2, instructing the system to perform the operations for viewing data of matching groups, a face management server 5 performs a view operation for viewing data of the matching groups, referring to a database containing data of matching groups to thereby create list information including a list of all matching groups, causing the administrator terminal to display the view screen for indicating the list of the matching groups based on the list information. When the administrator operates on the view screen (FIG. 15A) to select an item and instruct the system to perform a sorting operation, the face management server 5 creates sorted list information including a sorted list of matching groups, and causes the administrator terminal to display the view screen for indicating the sorted list of matching groups.

Next, the operations for updating data of a matching group in the system will be described.

As shown in FIG. 17C, an administrator operates an administrator terminal 2, instructing the system to perform the operations for updating data of a matching group. In the present embodiment, an administrator operates on the update screen (FIG. 15C) to enter updated data of a matching group and operates the update button 106.

When the administrator operates the administrator terminal 2, instructing the system to perform the operations for updating data of a matching group, a face management server 5 performs an update operation for updating a database of matching groups with the updated data of the matching group designated by the administrator. Then, when the update operation is completed, the face management server 5 causes the administrator terminal 2 to display on the screen an operation result indicating whether or not the update operation has been normally completed.

Figure 19:
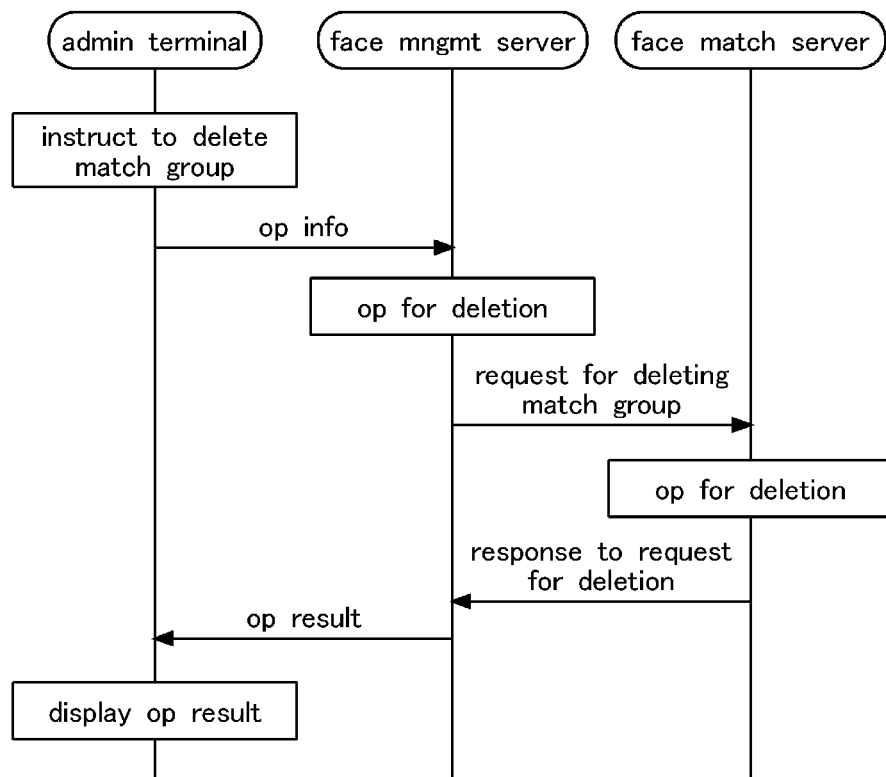
FIG. 19 is a sequence diagram showing an operation procedure of operations for deleting data of a matching group.
Figure 20:
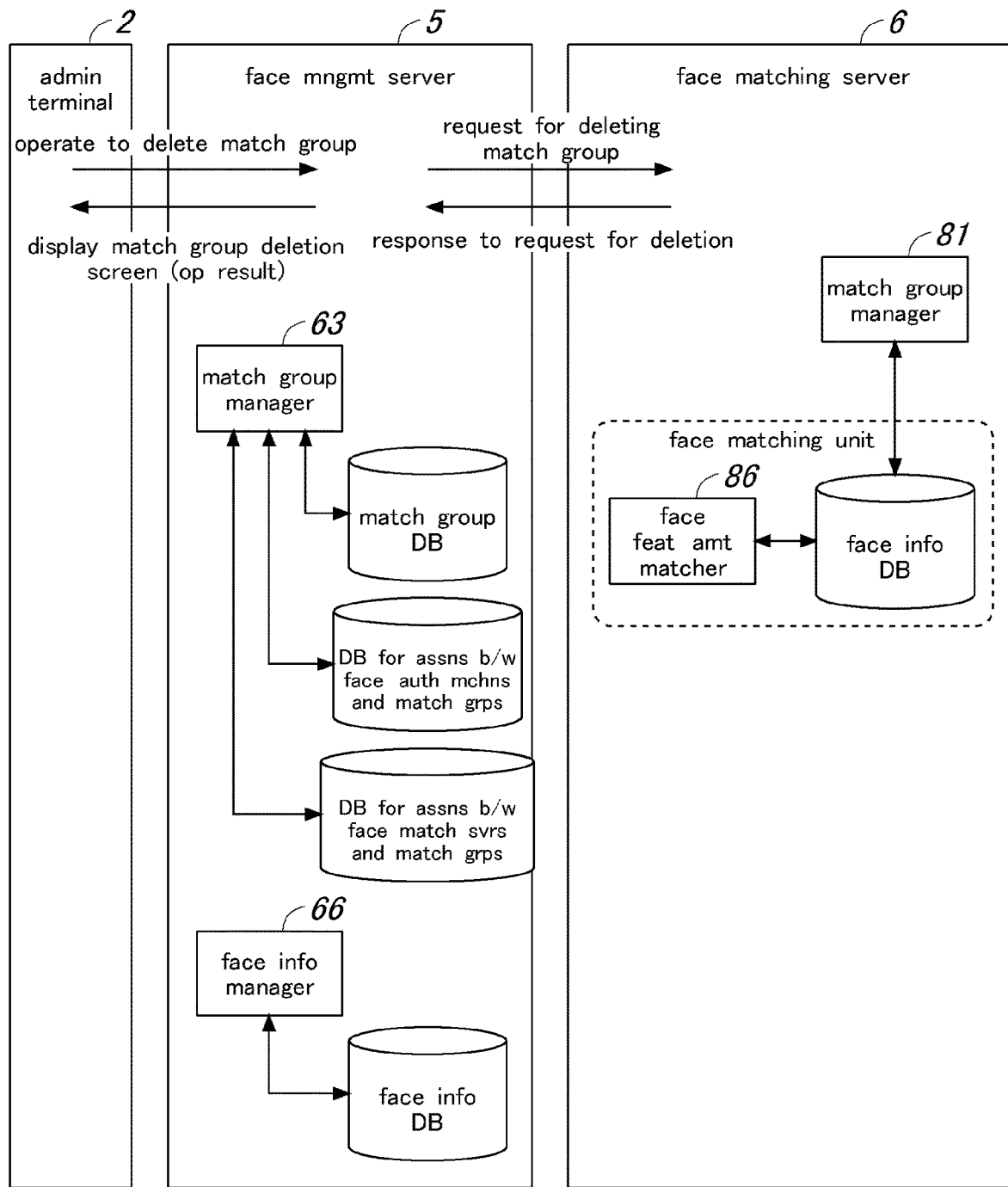
FIG. 20 is an explanatory diagram showing an outline of operations for deleting data of a matching group.

Next, the operations for deleting data of a matching group(s) will be described. FIG. 19 is a sequence diagram showing an operation procedure of the operations for deleting data of a matching group. FIG. 20 is an explanatory diagram showing an outline of the operations for deleting data of a matching group.

As shown in FIG. 19, an administrator operates an administrator terminal 2, instructing the system to perform the operations for deleting data of a matching group. In the present embodiment, an administrator operates on the deletion screen (FIG. 16) to select a matching group to be deleted and then operates the deletion button 108.

As shown in FIG. 20, when the administrator operates the administrator terminal 2, instructing the system to perform the operations for deleting data of a matching group, a face management server 5 performs deletion operations related to the matching group. In the deletion operations, the face management server 5 deletes the registered data related to the matching group designated by the administrator from a database of matching groups. The face management server 5 also deletes data of the association(s) between the designated matching group and a face matching server(s) 6. More specifically, the face management server 5 first deletes data of the association between the designated matching group and the face matching server(s) 6, and then deletes the registered data of the matching group. In addition, the face management server 5 deletes data related to the designated matching group from a database of associations between matching groups and users. Moreover, the face management server 5 deletes the face information (face feature amount data) of users who belongs to the designated matching group from a face information database. The face management server 5 also deletes data of the association(s) between the designated matching group and a face authentication machine(s) 1. The administrator access manager 61 in the face management server 5 records an administrator access log.

Furthermore, the face management server 5 transmits a request for deleting the matching group to the face matching server 6. The request for deleting the matching group includes information on the matching group to be deleted.

Upon receiving the request for deleting the matching group from the face management server 5, the face matching server 6 performs a deletion operation for deleting data of the matching group. The deletion operation involves deleting data of association(s) between the designated matching group and a face matcher(s) (face matching process). More specifically, the deletion operation involves disabling the face matcher for the designated matching group and deleting the face matching database for the designated matching group.

Then, when the deletion operation is completed, the face matching server 6 transmits a response to the request for deleting the matching group to the face management server 5. The response includes an operation result indicating whether or not the deletion operation has been normally completed.

When receiving the response to the request for deletion from the face matching server 6 and finishing all the operations for deletion, the face management server 5 causes the administrator terminal 2 to display on the screen an operation result indicating whether or not the operations for deletion have been normally completed.

With regard to the face authentication machine(s) 1 for the matching group, the data regarding the designated matching group is not deleted so as to reflect the result of the operations for deletion until the face authentication machine 1 is rebooted.

Figure 21:
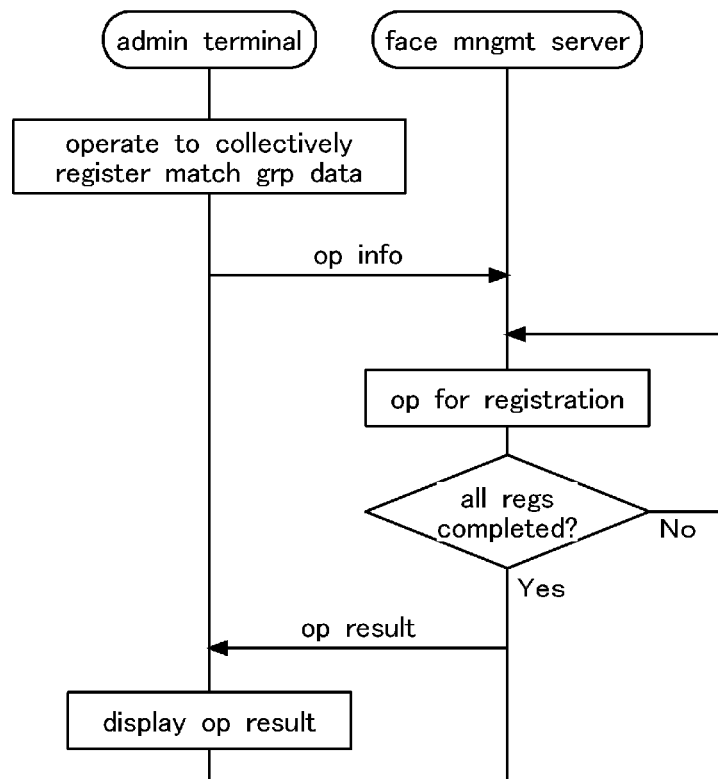
FIG. 21 is a sequence diagram showing an operation procedure of operations for collectively registering data of matching groups.

Next, operations for collectively registering data of matching groups will be described. FIG. 21 is a sequence diagram showing an operation procedure of operations for collectively registering data of matching groups.

The system of the present embodiment can collectively register data of matching groups in a face management server 5 by using a file containing information on a list of matching groups to be registered.

Specifically, an administrator operates an administrator terminal 2, instructing the system to perform the operations for collectively registering data of matching groups. In the present embodiment, an administrator operates on the registration screen (not shown) to select a file containing information on a list of matching groups to be registered, and then operates the registration button.

Then, the administrator terminal 2 reads the selected file of the target matching group list and displays the target matching group list in the confirmation screen on the administrator terminal 2. The administrator checks the registered data shown in the confirmation screen and then operates the screen, instructing the system to collectively register the matching groups in the list. If necessary, the administrator can modify some registered data in the list by operating on the confirmation screen.

When the administrator operates the administrator terminal 2, instructing the system to perform the operations for collectively registering data of matching groups, a face management server 5 performs a collective registration operation for collectively registering the listed matching groups. The collective registration operation involves repeatedly performing a registration operation for registering data of each matching group, based on the target matching group list acquired from the administrator terminal 2.

When the collective registration operation is completed, the face management server 5 causes the administrator terminal 2 to display on the screen an operation result indicating whether or not the collective registration operation has been normally completed. The face management server 5 also reports a matching group(s) which the server has failed to register data therefor, to the administrator and prompts the administrator to re-register the data of the matching group. The face management server 5 outputs the registration result as a log file.

Although the operations for collectively registering data of matching groups have been described, operations for collectively updating and/or deleting data of matching groups can be performed in a similar manner.

Figure 22A:
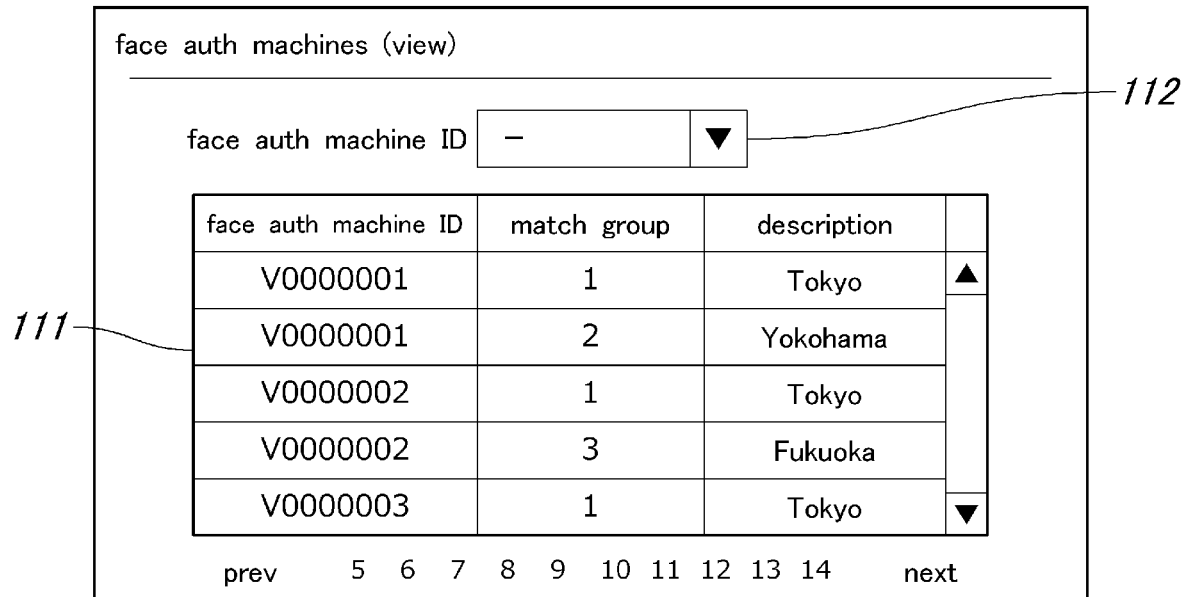
FIGS. 22A-B are explanatory diagrams showing screens displayed on the administrator terminal 2 when associations between face authentication machines 1 and matching groups are to be registered, viewed, and updated.
Figure 22B:
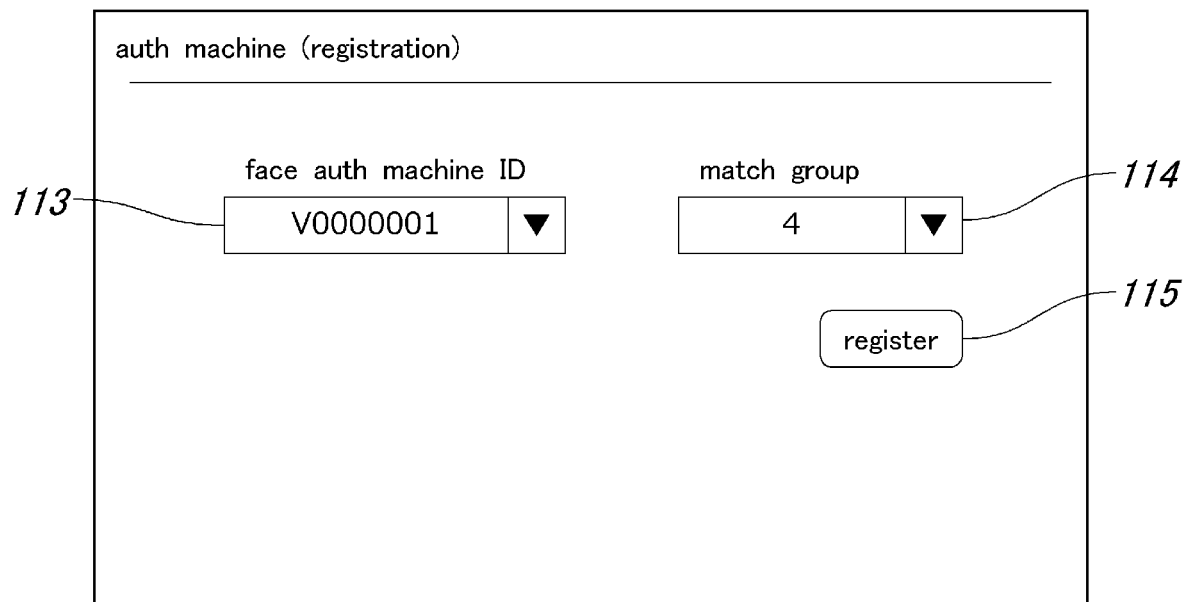

Next, operations for registering, viewing, updating and deleting associations between face authentication machines 1 and matching groups in the present system will be described. FIGS. 22A-B and 23 are explanatory diagrams showing screens displayed on the administrator terminal 2 when associations between face authentication machines 1 and matching groups are to be registered, viewed, updated and deleted.

When associations between face authentication machines 1 and matching groups are to be registered, viewed, updated, and deleted, an administrator terminal 2 displays a view screen shown in FIG. 22A, a registration screen shown in FIG. 22B, and a deletion screen shown in FIG. 23, respectively.

The view screen shown in FIG. 22A displays a list of registered associations between face authentication machines 1 and matching groups. By viewing the view screen, an administrator can check the registered associations between face authentication machines 1 and matching groups.

The view screen includes a list display section 111 and a face authentication machine designation section 112. The list display section 111 displays machine IDs of face authentication machines, matching groups (numbers) associated with the respective face authentication machines, and descriptions (installation location) about the respective registered matching groups. The face authentication machine designation section 112 provides a pulldown menu to allow an administrator to select a target face authentication machine 1 (machine ID). This allows the listed data records in the list display section 111 to be narrowed down to include designated face authentication machines; that is, only the matching groups associated with the designated face authentication machines are indicated in the list display section 111. When an administrator does not select any face authentication machine 1 at the face authentication machine designation section 112, the list display section 111 indicates data records of all the face authentication machines 1.

An administrator can designate an item (machine ID, face authentication machine 1, description) on the view screen to thereby perform a sort operation. In some cases, the view screen may allow an administrator to designate the number of items displayed in the list display section 111 (the number of face authentication machines 1) and the display range of the face authentication machines 1 and matching groups. Furthermore, the view screen may allow an administrator to designate search conditions for respective items (machine ID, face authentication machine 1, description) to thereby perform a search operation.

In the example shown in FIG. 22A, the face authentication machines 1 are grouped based on the places where the face authentication machines 1 are installed (e.g., the locations of business offices).

The registration screen (second screen) shown in FIG. 22B allows an administrator to set an association between a face authentication machine 1 and a matching group. By operating the registration screen, an administrator can register data of an association between a face authentication machine 1 and a matching group.

The registration screen includes a face authentication machine designation section 113, a matching group designation section 114, and a registration button 115. The face authentication machine designation section 113 provides a pulldown menu to allow an administrator to select a target face authentication machine 1 (machine ID). The matching group designation section 114 provides a pulldown menu to allow an administrator to select a matching group of the target face authentication machine 1. The pulldown menu indicates all registered matching groups which have been registered through the matching group registration screen (see FIG. 15B). When an administrator designates a face authentication machine and a matching group(s) to be associated therewith, and then operates the registration button 115, the face management server 5 performs a registration operation for registering the entered data of an association in the database of associations.

When registering an association between one face authentication machine 1 and a plurality of matching groups, an administrator can repeatedly perform a registration operation for associating the one face authentication machine with each matching group by operating the registration screen. In some cases, the registration screen may include a plurality of matching group designation sections 114.

The deletion screen shown in FIG. 23 allows an administrator to delete data of one or more associations between face authentication machines 1 and matching groups.

The deletion screen includes a list display section 116, a face authentication machine designation section 117, and a deletion button 118. The list display section 116 displays machine IDs of face authentication machines, matching group IDs (numbers) associated with the respective face authentication machines, and the corresponding descriptions (installation locations) about matching groups. The list display section 116 includes a check box for each association. This allows an administrator to select one or more associations to be deleted. When an administrator marks one or more checkboxes to select registered associations to be deleted and then operates the deletion button 118, the face management server 5 performs a deletion operation for deleting data of the selected registered associations. The face authentication machine designation section 117 provides a pulldown menu to allow an administrator to select a face authentication machine 1. This allows the listed data records in the list display section 116 to be narrowed down to include a designated face authentication machine.

Then, when the administrator selects "view" in the menu screen (not shown), the screen transitions to the view screen shown in FIG. 22A. When the administrator selects "registration" in the menu screen, the screen transitions to the registration screen shown in FIG. 22B. When the administrator selects "deletion" in the menu screen, the screen transitions to the deletion screen shown in FIG. 23. When the administrator selects "update" in the menu screen, the screen transitions to the update screen (not shown). When an administrator selects an association between a face authentication machine 1 and a matching group on the view screen, the screen transitions to the update screen (not shown).

Although, in the example shown in FIG. 23, the registered associations are displayed in a list on the deletion screen, an individual data edit screen may be formed to allow an administrator to delete an association therein. The update screen (not shown) is the same as the registration screen (FIG. 22B).

Figure 24:
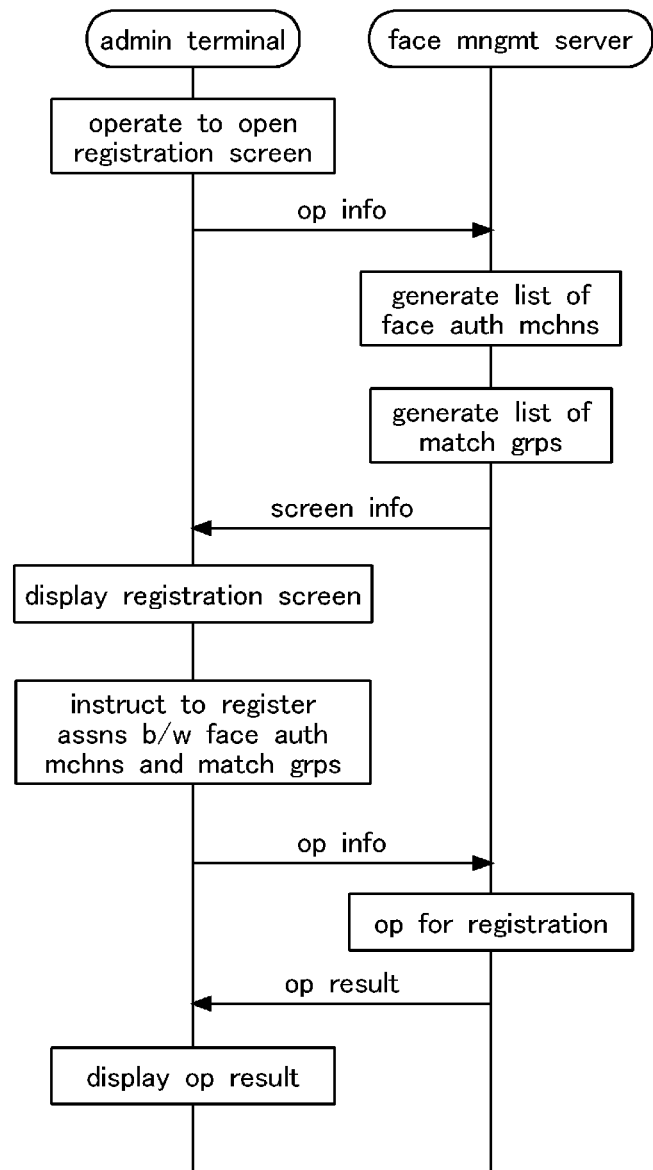
FIG. 24 is a sequence diagram showing an operation procedure of operations for registering an association between a face authentication machine 1 and a matching group.
Figure 25:
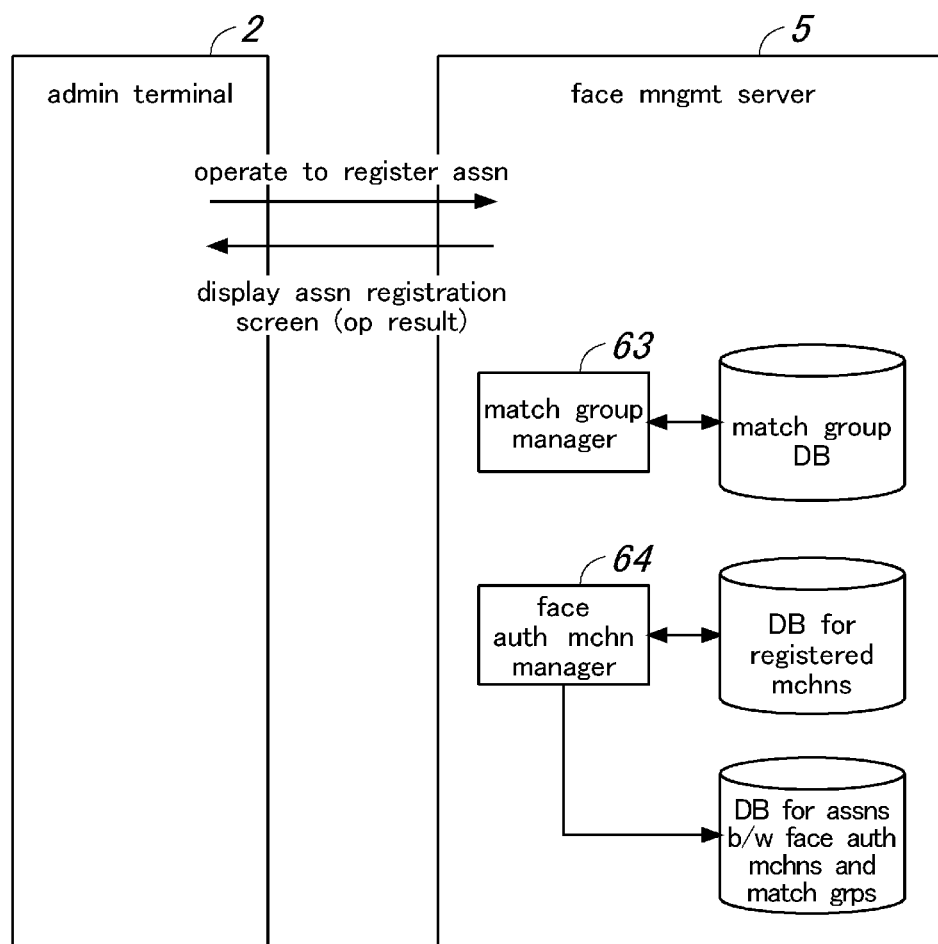
FIG. 25 is an explanatory diagram showing an outline of the operations for registering an association between a face authentication machine 1 and a matching group.

Next, the operations for registering associations between a face authentication machine and a matching group(s). FIG. 24 is a sequence diagram showing an operation procedure of operations for registering an association between a face authentication machine 1 and a matching group. FIG. 25 is an explanatory diagram showing an outline of the operations of registering an association between a face authentication machine 1 and a matching group.

An administrator operates an administrator terminal 2 to open the registration screen (see FIG. 22B). In the present embodiment, an administrator selects "registration" in the menu screen (not shown).

As shown in FIG. 25, when an administrator operates an administrator terminal 2 to open the registration screen, a face management server 5 creates face authentication machine list information including a list of face authentication machines 1, referring to a database containing data of registered machines (face authentication machines 1 and face matching servers 6). The face management server 5 also creates matching group list information including a list of matching groups, referring to a database containing data of matching groups. Then, based on the face authentication machine list information and the matching group list information, the face management server 5 generates screen information for the registration screen and causes the administrator terminal 2 to display the registration screen.

Next, the administrator operates the registration screen displayed on the administrator terminal 2, instructing the system to register data of an association between a face authentication machine and a matching group. In the present embodiment, the administrator enters a combination of a face authentication machine and a matching group on the registration screen (FIG. 22B) and then operates the registration button.

When the administrator operates the administrator terminal 2, instructing the system to register data of an association between the face authentication machine and the matching group, the face management server 5 performs a registration operation for registering the association between the face authentication machine 1 and the matching group. In the registration operation, the face management server 5 registers the association (i.e., the combination of the face authentication machine and the matching group) designated by the administrator in the database. In the face authentication machine 1, associations between face authentication machines 1 and matching groups are not updated to reflect the result of the registration operation when the face authentication machine 1 is rebooted.

Then, when the registration operation is completed, the face management server 5 causes the administrator terminal 2 to display an operation result on the screen indicating whether or not the registration operation has been normally completed.

Figure 26:
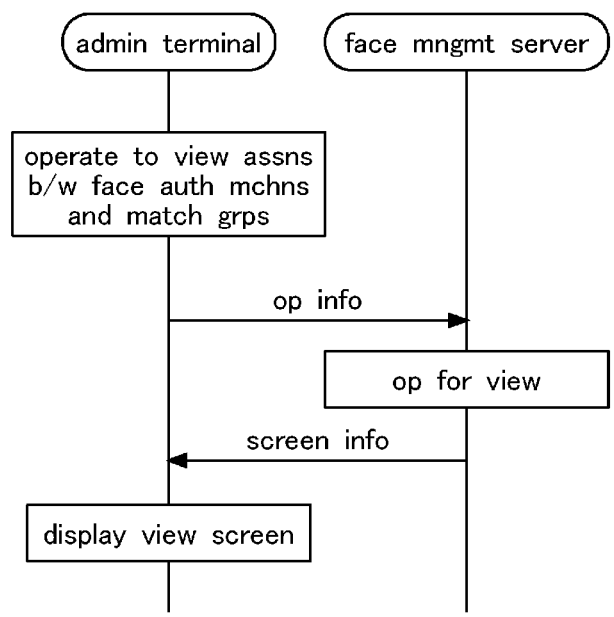
FIG. 26 is a sequence diagram showing an operation procedure of operations for viewing associations between face authentication machines 1 and matching groups.

Next, the operations for viewing data of associations between face authentication machines 1 and matching groups will be described. FIG. 26 is a sequence diagram showing an operation procedure of operations for viewing associations between face authentication machines 1 and matching groups.

An administrator operates an administrator terminal 2, instructing the system to perform the operations for viewing associations between face matching servers 6 and matching groups. In the present embodiment, an administrator operates the menu screen to open the view screen (see FIG. 22A).

When an administrator operates the administrator terminal 2, instructing the system to perform the operations for viewing associations between face authentication machines 1 and matching groups, the face management server 5 performs a view operation for viewing associations between face authentication machines 1 and matching groups. In the view operation, the face management server 5 creates a list of associations for all the face matching servers 6 and causes the administrator terminal 2 to display the view screen. When an administrator operates to narrow down the face authentication machines 1 to be indicated on the view screen, the face management server 5 creates a list of associations for the selected face authentication machines 1, causing the administrator terminal 2 to display the view screen indicating associations that are narrowed down. When an administrator operates on the view screen to select an item and instructs the system to perform a sorting operation, the face management server 5 creates sorted list information including a sorted list of associations, causing the administrator terminal to display the view screen based on the sorted list information.

In addition, the face management server 5 records an administrator access log.

Figure 27:
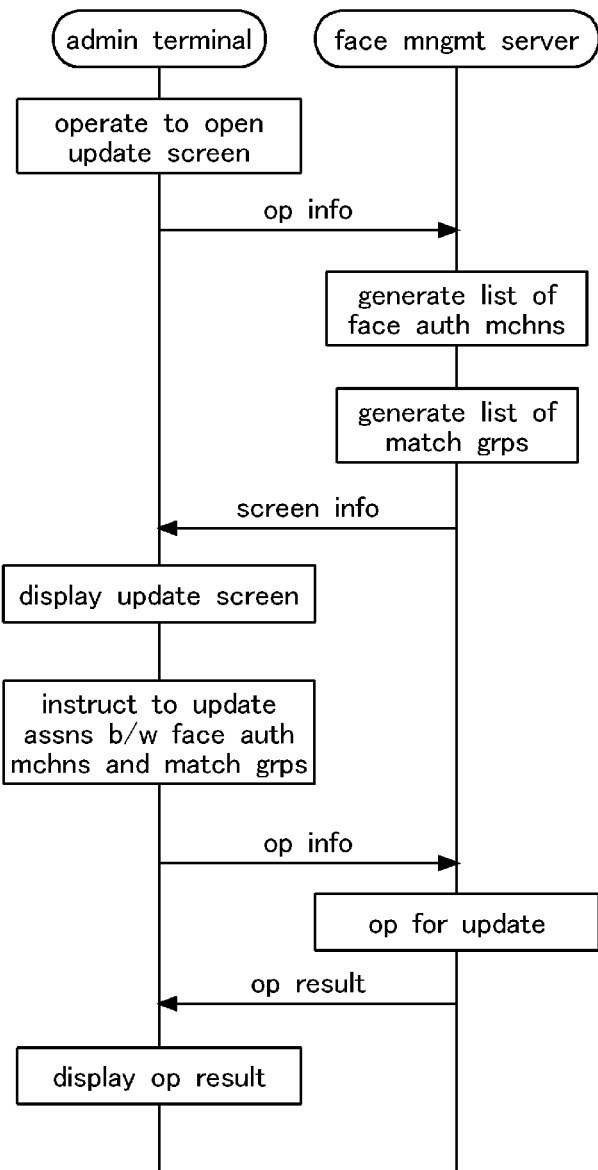
FIG. 27 is a sequence diagram showing an operation procedure of operations for updating associations between face authentication machines 1 and matching groups.

Next, the operations for updating associations (data of associations) between face authentication machines 1 and matching groups will be described. FIG. 27 is a sequence diagram showing an operation procedure of operations for updating associations between face authentication machines 1 and matching groups.

An administrator operates an administrator terminal 2 to open the update screen (not shown). In the present embodiment, an administrator selects "update" in the menu screen (not shown).

When an administrator operates an administrator terminal 2 to open the update screen, a face management server 5 creates face authentication machine list information including a list of face authentication machines 1, referring to the database containing data of registered machines. The face management server 5 also creates matching group list information including a list of matching groups, referring to the database containing data of matching groups. Then, based on the face authentication machine list information and the matching group list information, the face management server 5 generates screen information for the update screen to cause the administrator terminal 2 to display the update screen.

Next, the administrator operates the update screen displayed on the administrator terminal 2, instructing the system to update the registered data of associations between face authentication machines and matching groups. In the present embodiment, the administrator enters update data on the update screen (not shown) and then operates the update button. Entry of the update data changes the combination of a face authentication machine and a matching group.

When an administrator operates the administrator terminal 2, instructing the system to update data of an association between a face authentication machine and a matching group, the face management server 5 performs an update operation to update the association between the face authentication machine and the matching group designated by the administrator. When the update operation is completed, the face management server 5 causes the administrator terminal 2 to display an operation result on the screen to indicate whether or not the update operation has been normally completed.

Figure 28:
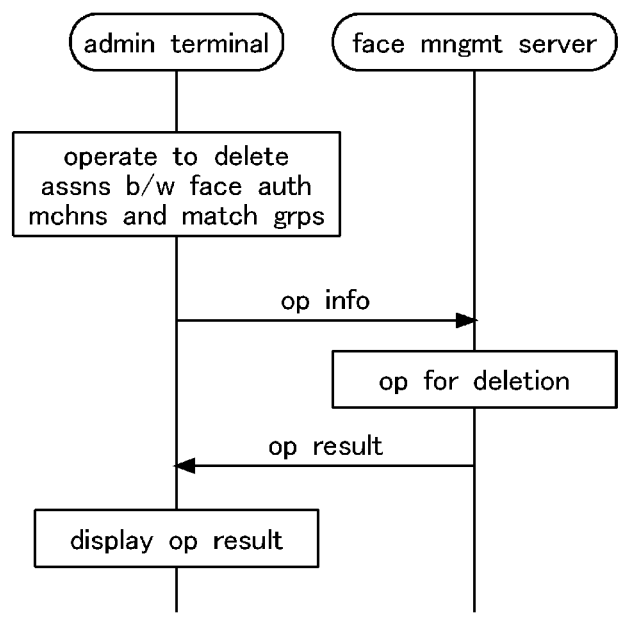
FIG. 28 is a sequence diagram showing an operation procedure of operations for deleting associations between face authentication machines 1 and matching groups.

Next, the operations for deleting data of associations between face authentication machines 1 and matching groups will be described. FIG. 28 is a sequence diagram showing an operation procedure of the operations for deleting associations between face authentication machines 1 and matching groups.

An administrator operates an administrator terminal 2, instructing the system to delete associations between face authentication machines and matching groups. In the present embodiment, an administrator operates the deletion screen (see FIG. 23) to select registered data (associations) to be deleted and then operate the deletion button.

When an administrator operates an administrator terminal 2, instructing the system to delete the registered data of associations between face authentication machines 1 and matching groups, the face management server 5 performs a deletion operation for deleting the associations between the face authentication machines 1 and the matching groups. The deletion operation involves deleting the data of the associations between the face authentication machines 1 and the matching groups designated by the administrator.

When the deletion operation is completed, the face management server 5 causes the administrator terminal 2 to display an operation result on the screen to indicate whether or not the deletion operation has been normally completed. In addition, the face management server 5 records an administrator access log.

Figure 29A:
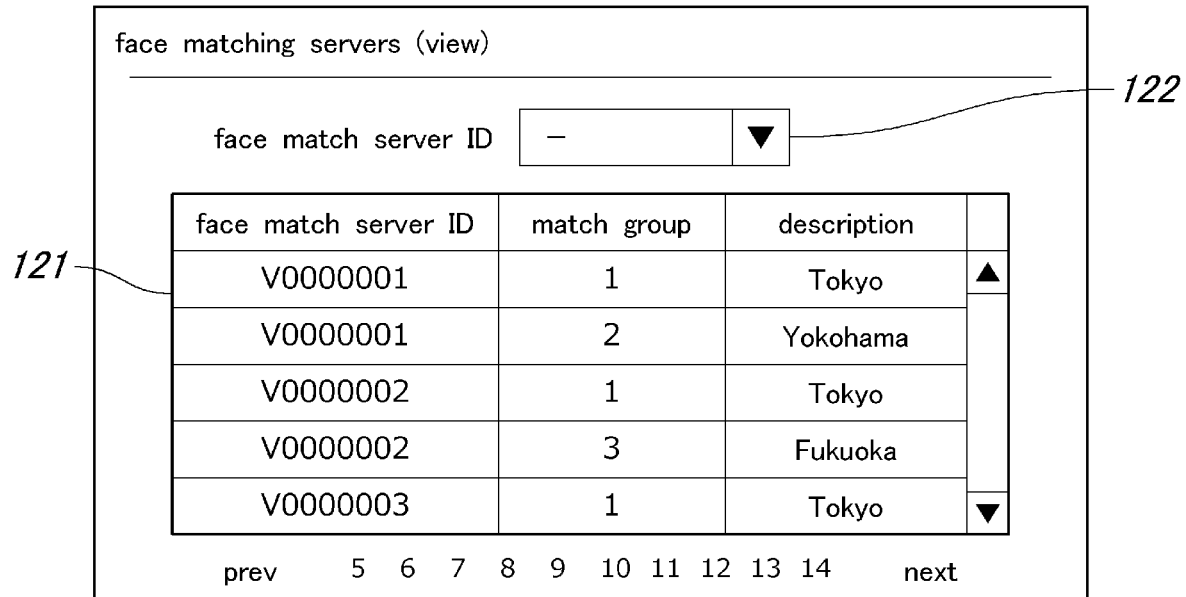
FIGS. 29A-B are explanatory diagrams showing screens displayed on the administrator terminal 2 when associations between face matching servers 6 and matching groups is to be registered and viewed.
Figure 29B:
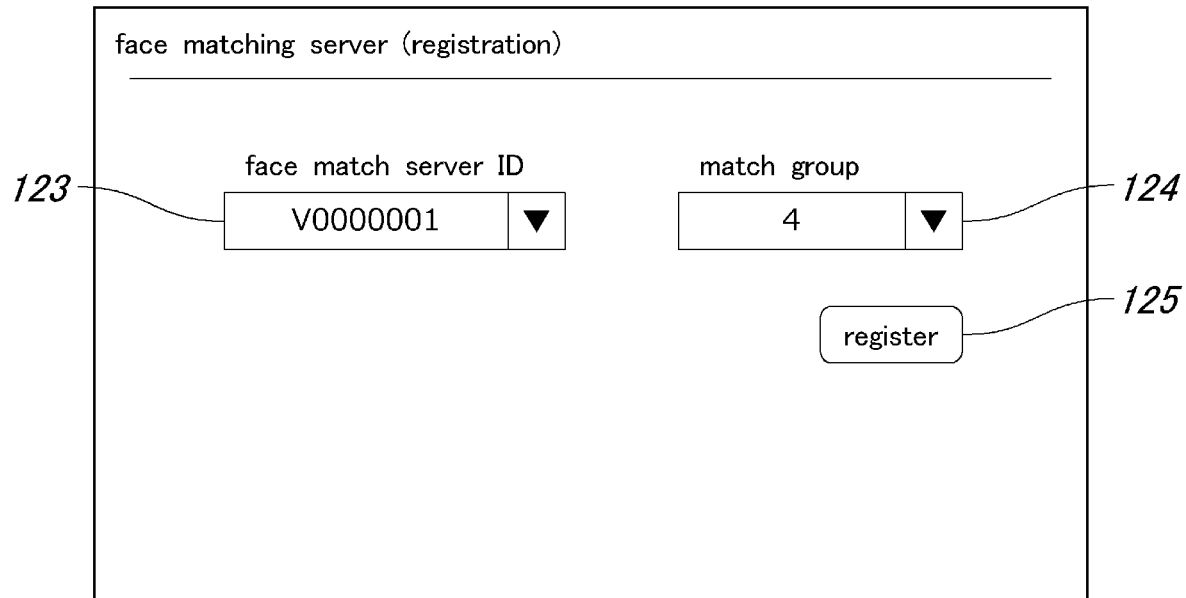

Next, operations for registering, viewing, and deleting associations between face matching servers 6 and matching groups in the present system will be described. FIGS. 29A-B and 30 are explanatory diagrams showing screens displayed on the administrator terminal 2 when associations between face matching servers 6 and matching groups are to be registered, viewed, and deleted.

When one or more associations between face matching servers 6 and matching groups are to be registered, viewed, updated, and deleted, an administrator terminal 2 displays a view screen shown in FIG. 29A, a registration screen shown in FIG. 29B, and a deletion screen shown in FIG. 30, respectively.

The view screen shown in FIG. 29A displays a list of registered associations between face matching servers 6 and matching groups. By viewing the view screen, an administrator can check the registered associations between face matching servers 6 and matching groups.

The view screen includes a list display section 121 and a face matching server designation section 122. The list display section 121 displays machine IDs of face matching servers, matching groups (numbers) associated with the respective face matching servers, and descriptions about the respective registered matching groups. The face matching server designation section 122 provides a pulldown menu to allow an administrator to select a target face matching server 6 (machine ID). This allows the listed data records in the list display section 121 to be narrowed down to include designated face matching servers; that is, only the matching groups associated with the designated face matching servers are indicated in the list display section 121. When an administrator does not select any face matching server 6 at the face matching server designation section 122, the list display section 121 indicates data records of all the face matching servers 6.

An administrator can designate an item (machine ID, matching server 6, description) on the view screen to thereby perform a sort operation. In some cases, the view screen may allow an administrator to designate the number of items displayed in the list display section 121 (the number of face matching servers 6) and the display range of the face matching servers 6 and matching groups. Furthermore, the view screen may allow an administrator to designate search conditions for respective items (machine ID, face matching server 6, description) to thereby perform a search operation.

The registration screen (second screen) shown in FIG. 29B allows an administrator to designate an association between a face matching server 6 and a matching group.

The registration screen includes a face matching server designation section 123, a matching group designation section 124, and a registration button 125. The face matching server designation section 123 provides a pulldown menu to allow an administrator to select a target face matching server 6 (machine ID). The matching group designation section 124 provides a pulldown menu to allow an administrator to select a matching group of the target face matching server 6. The pulldown menu indicates registered matching groups which have been registered through the matching group registration screen (see FIG. 15B).

When the administrator designates a combination of a face matching server and a matching group(s) and then operates the registration button 125, the face management server 5 performs a registration operation for registering the association in a database containing associations.

When a plurality of matching groups are assigned to one face matching server, an administrator can repeatedly operate on the registration screen to perform operations for registering associations between the face matching server and the respective matching groups. In some cases, the registration screen may include a plurality of matching group designation sections 124.

The deletion screen shown in FIG. 30 allows an administrator to delete data of one or more associations between face matching servers 6 and matching groups.

The deletion screen includes a list display section 126, a face matching server designation section 127, and a deletion button 128. The list display section 126 displays machine IDs of face matching servers 6, matching group IDs (numbers) associated with the face matching servers 6, and the descriptions about matching groups. The list display section 126 includes a check box for each association. This allows an administrator to select one or more associations. When an administrator marks one or more checkboxes to select registered associations to be deleted and then operates the deletion button 128, the face management server 5 performs a deletion operation for deleting data of the selected registered associations. The face matching server designation section 127 provides a pulldown menu to allow an administrator to select a face matching server 6. This allows the listed data records in the list display section 126 to be narrowed down to include a designated face matching server 6.

The view screen shown in FIG. 29A is displayed when an administrator selects "view" in the menu screen (not shown). The registration screen shown in FIG. 29B is displayed when an administrator selects "registration" in the menu screen (not shown). The deletion screen shown in FIG. 30 is displayed when an administrator selects "deletion" in the menu screen (not shown). In the view screen shown in FIG. 29A, when the administrator selects a face matching server(s) 6 in the list display section 121, the screen transitions to the registration screen, which allows the administrator to change the association between a face matching server 6 and a matching group.

Although, in the example of the deletion screen shown in FIG. 30, the registered associations are displayed in the form of a list, an individual data edit screen (not shown) may be formed to allow an administrator to delete an individual association in the screen.

Figure 31:
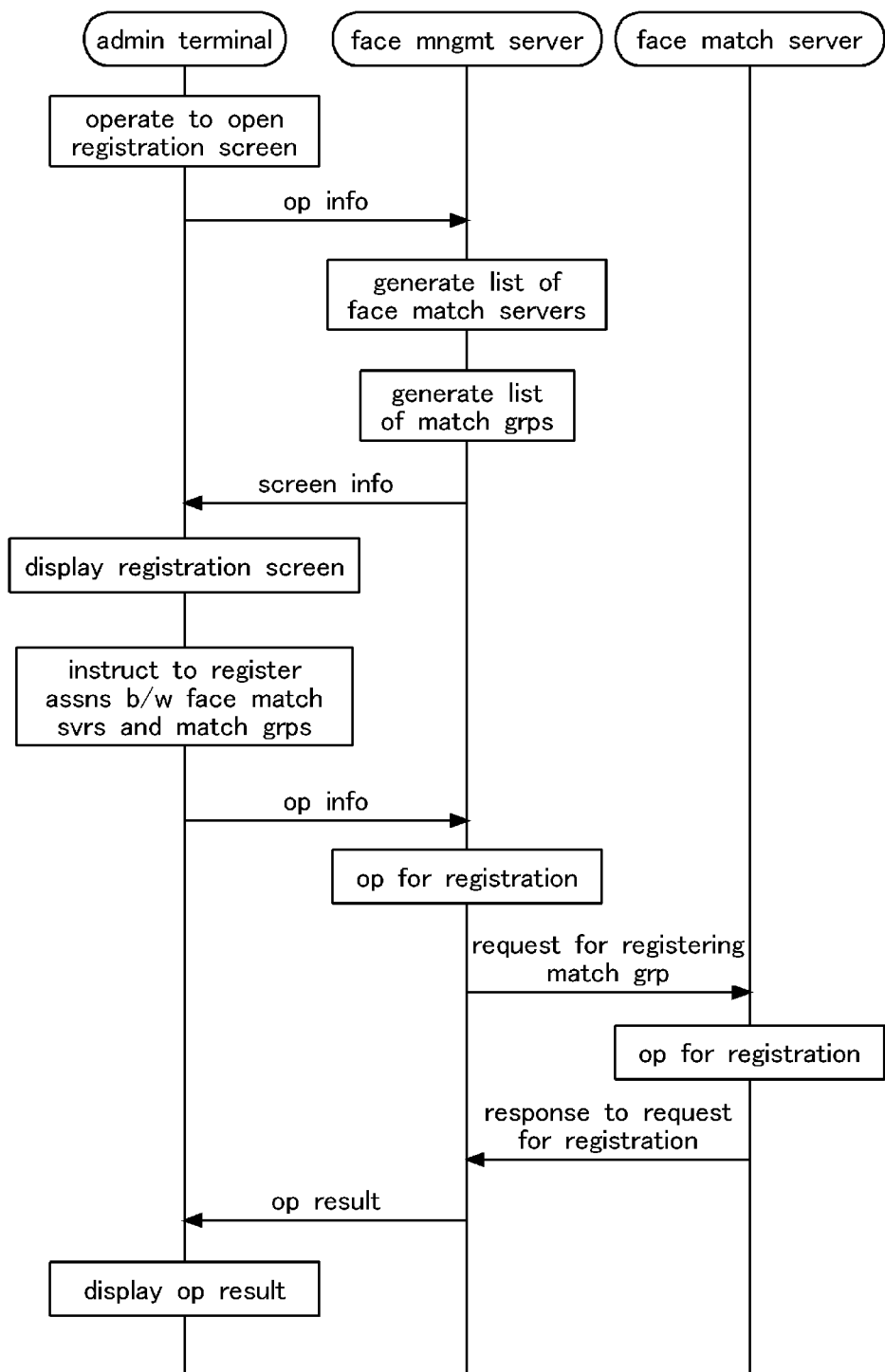
FIG. 31 is a sequence diagram showing an operation procedure of operations for registering an association between a face matching server 6 and a matching group.

Next, the operations for registering an association between a face matching server 6 and a matching group(s). FIG. 31 is a sequence diagram showing an operation procedure of the operations for registering an association between a face matching server 6 and a matching group.

An administrator operates an administrator terminal 2 to open the registration screen (see FIG. 29B). In the present embodiment, an administrator selects "registration" in the menu screen (not shown).

When an administrator operates an administrator terminal 2 to open the registration screen, a face management server 5 creates face matching server list information including a list of face matching servers 6, referring to the database containing data of registered machines. The face management server 5 also creates matching group list information including a list of matching groups, referring to the database containing data of matching groups. Then, based on the face matching server list information and the matching group list information, the face management server 5 generates screen information for the registration screen and causes the administrator terminal 2 to display the registration screen.

Next, the administrator operates the registration screen of the administrator terminal 2, instructing the system to register an association between a face matching server 6 and a matching group. In the present embodiment, the administrator enters a combination of a face matching server 6 and a matching group on the registration screen (FIG. 29B) and then operates the registration button 125.

When the administrator operates the administrator terminal 2, instructing the system to register the association between the face matching server 6 and the matching group, the face management server 5 performs a registration operation for registering the association between the face matching server 6 and the matching group. In the registration operation, the face management server 5 registers the association (i.e., the combination of the face matching server 6 and the matching group) designated by the administrator in the database.

Furthermore, the face management server 5 transmits a request for matching group registration to the face matching server 6.

Upon receiving the request for matching group registration from the face management server 5, the face matching server 6 performs a registration operation for registering the matching group. The registration operation registers the designated matching group as setting information for the face matching server 6. Then, when the registration operation is completed, the face matching server 6 transmits a response to the request for matching group registration to the face management server 5.

When the registration operations are completed, the face management server 5 causes the administrator terminal 2 to display an operation result indicating whether or not the operations for registration have been normally completed on the screen. In addition, the face management server 5 records an administrator access log.

Figure 32:
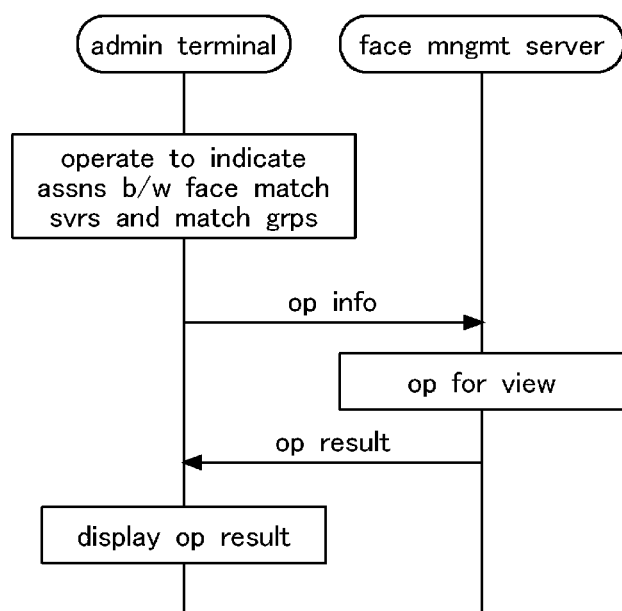
FIG. 32 is a sequence diagram showing an operation procedure of operations for viewing associations between face matching servers 6 and matching groups.

Next, operations for viewing associations between face matching servers 6 and matching groups will be described. FIG. 32 is a sequence diagram showing an operation procedure of operations for viewing associations between face matching servers 6 and matching groups.

An administrator operates an administrator terminal 2, instructing the system to perform the operations for viewing associations between face matching servers 6 and matching groups. In the present embodiment, an administrator operates the menu screen to open the view screen (see FIG. 22A).

When the administrator operates the administrator terminal 2, instructing the system to perform the operations for viewing associations between face matching servers 6 and matching groups for viewing, the face management server 5 performs a view operation for viewing associations between face matching servers 6 and matching groups. In the view operation, the face management server 5 creates a list of associations for all the face matching servers 6 and causes the administrator terminal 2 to display the view screen. When an administrator operates to narrow down the face matching servers 6 to be indicated on the view screen, the face management server 5 creates a list of associations for the selected face matching servers 6, causing the administrator terminal 2 to display the view screen indicating associations that are narrowed down. When an administrator operates on the view screen to select an item and instructs the system to perform a sorting operation, the face management server 5 creates sorted list information including a sorted list of associations, causing the administrator terminal to display the view screen based on the sorted list information.

In addition, the face management server 5 records an administrator access log.

Figure 33:
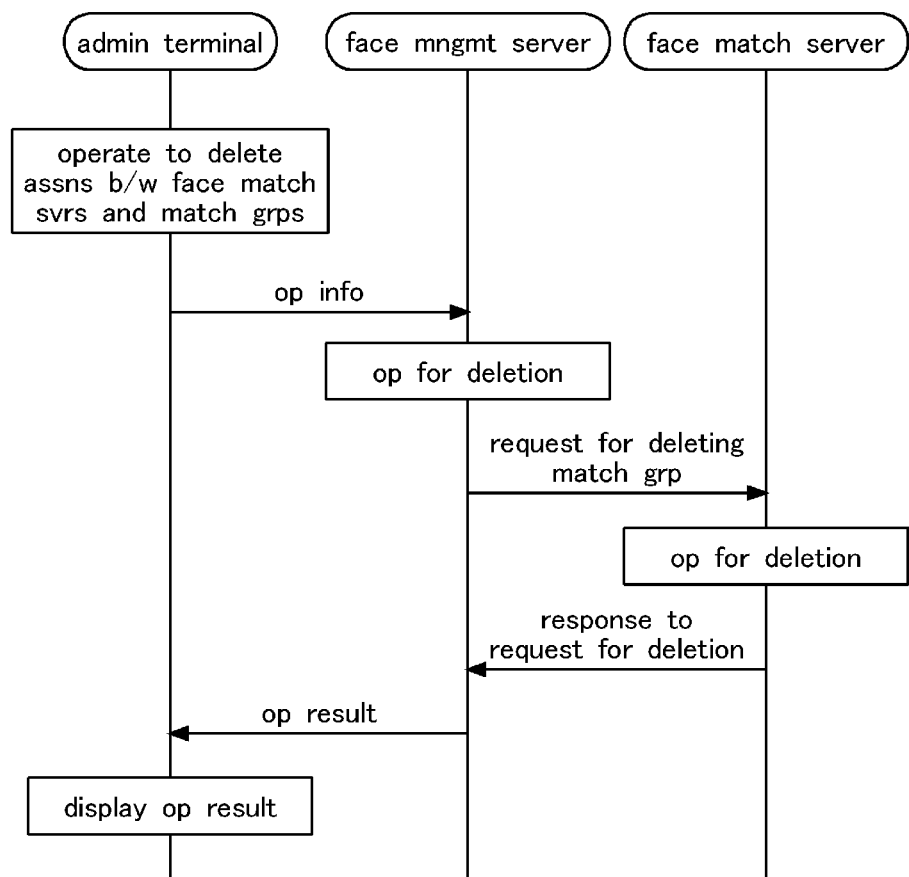
FIG. 33 is a sequence diagram showing an operation procedure of operations for deleting associations between face matching servers 6 and matching groups.
Figure 34:
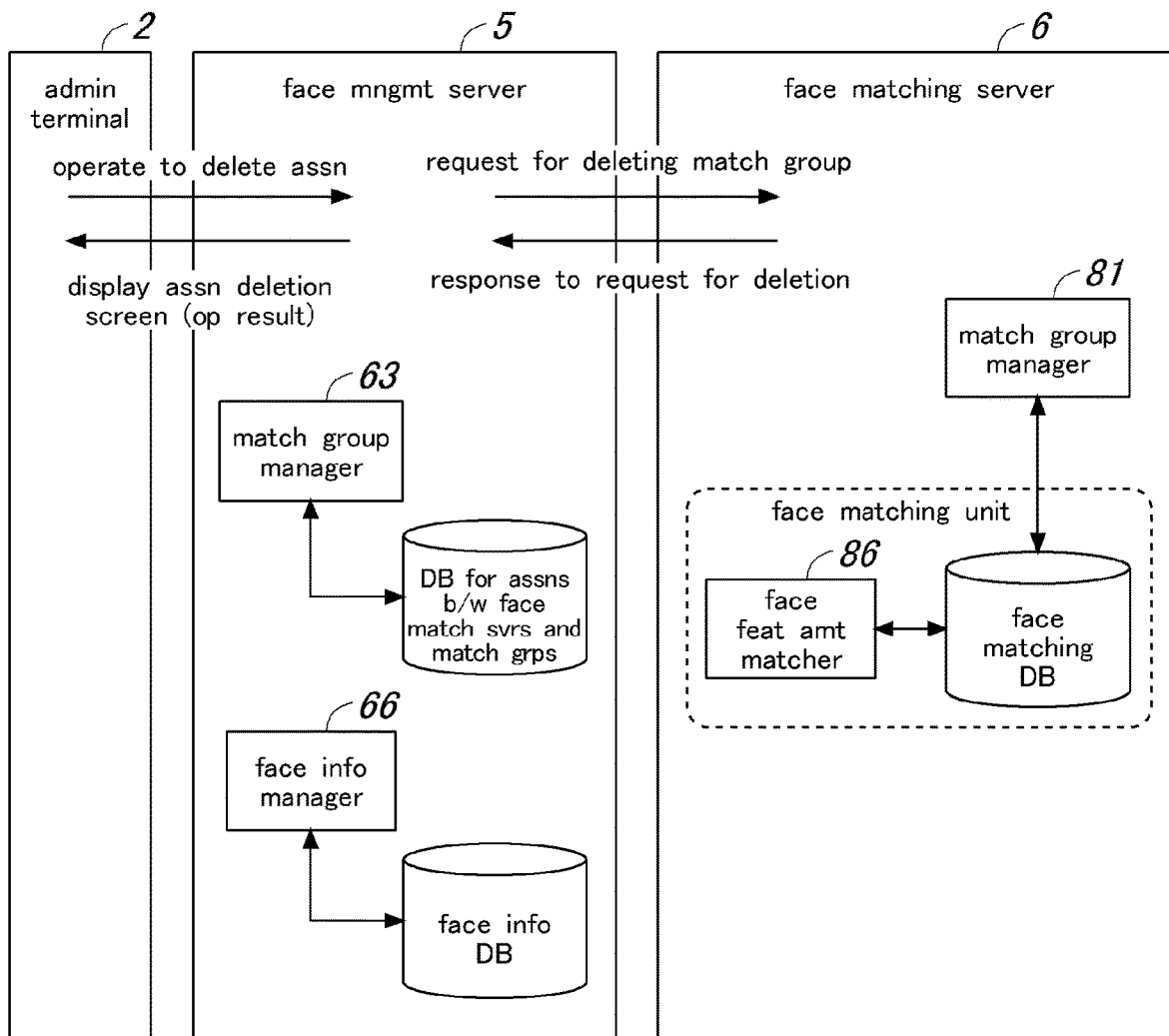
FIG. 34 is an explanatory diagram showing an outline of the operations for deleting associations between face matching servers 6 and matching groups.

Next, the operations for deleting data of associations between face matching servers 6 and matching groups will be described. FIG. 33 is a sequence diagram showing an operation procedure of operations for the operations for deleting associations between face matching servers 6 and matching groups. FIG. 34 is an explanatory diagram showing an outline of the operations for deleting associations between face matching servers 6 and matching groups.

An administrator operates an administrator terminal 2, instructing the system to delete associations between face matching servers 6 and matching groups. In the present embodiment, an administrator operates the deletion screen (see FIG. 30) to select registered data (associations) to be deleted and then operate the deletion button.

As shown FIG. 34, when an administrator operates an administrator terminal 2, instructing the system to delete the registered data of associations between face matching servers 6 and matching groups, the face management server 5 performs a deletion operation for deleting the associations between the face matching servers 6 and the matching groups. The deletion operation involves deleting the data of the associations between the face matching servers 6 and the matching groups designated by the administrator. The deletion operation further involves deleting face registration IDs related to the face matching server 6 from the face information database.

In addition, the face management server 5 transmits a request for matching group deletion to the face matching server 6.

Upon receiving the request for matching group deletion from the face management server 5, the face matching server 6 performs a deletion operation for deleting the matching group. The deletion operation deletes the designated matching group as setting information for the face matching server 6. Then, when the deletion operation is completed, the face matching server 6 transmits a response to the request for matching group deletion to the face management server 5.

When the deletion operations are completed, the face management server 5 causes the administrator terminal 2 to display an operation result indicating whether or not the operations for deletion have been normally completed on the screen. In addition, the face management server 5 records an administrator access log.

Figures 35A, 35B:
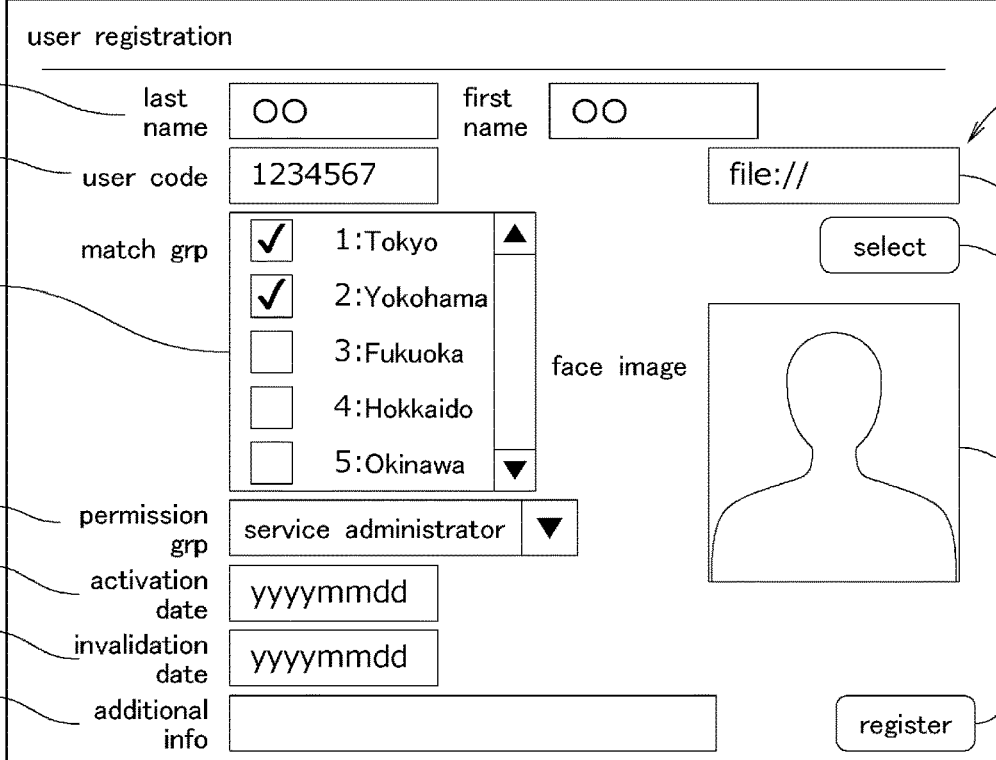
FIGS. 35A-B are explanatory diagrams showing screens displayed on the administrator terminal 2 when data of a user is to be registered, viewed, updated, and deleted.

Next, operations for registering, viewing, updating and deleting data of users will be described. FIGS. 35A-B and 36 are explanatory diagrams showing screens displayed on the administrator terminal 2 when data of a user(s) is to be registered, viewed, updated, and deleted.

For the operations for registering, viewing, updating and deleting data of matching groups, an administrator terminal 2 displays an individual data edit screen shown in FIG. 35A, a search screen shown in FIG. 35B, and a list indication screen shown in FIG. 36.

The individual data edit screen (second screen, third screen) shown in FIG. 35A is used for registering, viewing, updating, displaying, and deleting user data.

The individual data edit screen includes a first and last name input section 131, a user code input section 132, a matching group input section 133, a permission group input section 134, an activation date input section 135, an invalidation date input section 136, an additional information input section 137, a face image input section 138, and an execution button 139.

The first and last name input section 131 allows an administrator to enter a user's first and last name. The user code input section 132 allows an administrator to enter a user code or code number (such as employee number). The matching group input section 133 allows an administrator to designate a matching group(s). The matching group input section 133 displays the matching groups which have been registered through the registration screen (see FIG. 15B) for registering matching groups. Checkboxes in the matching group input section 133 allow an administrator to select one or more matching groups. The permission group input section 134 allows an administrator to designate a permission group. Specifically, the permission group input section 134 provides a pull-down menu to allow an administrator to select a permission group. The activation date input section 135 allows an administrator to enter an activation date; that is, the date on which face matching for the user was enabled. The invalidation date input section 136 allows an administrator to enter an invalidation date; that is, the date on which face matching for the user was disabled. The setting of activation dates/invalidation dates for multiple users enables the system to simultaneously start and end the services for those users. The additional information input section 137 allows an administrator to enter additional information.

The face image input section 138 includes a face image designation section 141, a selection button 142, and a face image display section 143. The face image designation section 141 allows an administrator to designate a file of a shot image of a user. When an administrator designates a file of the user's shot image which has been stored in the administrator terminal 2, and then operates the selection button 142, the administrator terminal 2 transmits the user's shot image to the face matching server 6 via the face management server 5, where the face matching server 6 performs operations for generating a face image from the user's shot image (operations of face detection and face cut-out), and causes the administrator terminal 2 to display the user's face image on the face image display section 143.

When the administrator enters data records of the respective items on the registration screen and operates the execution button 139, the face management server 5 performs the operations for registering user data based on the entered data records.

In this way, the registration screen allows an administrator to assign a matching group to a user, to thereby register an association between the user and the matching group in the database. The registration screen also allows an administrator to register the activation date and the invalidation date. The activation date and the invalidation date determine the period during which a user's face information (face feature amount data) is stored in a face matching server 6; that is, a user's face image data is registered in the database in the face matching server 6 on the activation date, and the data is deleted from the database on the invalidation date.

In addition, when an administrator operates the registration screen to designate a user's shot image, the face image data of the user is registered in the database in the face matching server 6.

The search screen shown in FIG. 35B allows an administrator to enter search conditions for registered user data. Using the search screen, user data can be narrowed down to meet search conditions so that a narrowed down list of the user data is shown on the screen. The search screen includes a first and last name input section 131, a user code input section 132, a matching group input section 133, a permission group input section 134, an activation date input section 135, an invalidation date input section 136, an update date input section 144, a number-of-result input section 145, and a search button 146.

The first and last name input section 131, the user code input section 132, the matching group input section 133, the permission group input section 134, the activation date input section 135, the invalidation date input section 136 are the same as those in the registration screen. The update date input section 144 allows an administrator to designate the update date (period), and the number-of-result input section 145 allows an administrator to designate the maximum number of search results to be retrieved.

When an administrator enters data records as necessary and operates the search button 146, the screen transitions to the list indication screen (FIG. 36) which reflects the search result.

The list indication screen shown in FIG. 36 is used to indicate a list of user data of registered users, and can be used to collectively update and/or collectively delete user data.

By viewing the view screen, an administrator can check the registered user data. The list indication screen includes a list display section 147 and an execution button 148. The list display section 147 displays user codes, first and last names, and matching group of users. The list display section 147 also includes a check box for each user, which allows an administrator to select one or more registered users. When an administrator marks one or more checkboxes to select users to be deleted and then operates the execution button 148 (deletion button), the face management server 5 performs operations for deleting data of the selected users.

An administrator can designate an item (user code, first/last name, matching group) on the list indication screen to thereby perform a sort operation (reordering). In some cases, the list indication screen may be formed to allow an administrator to designate the number to be indicated (the number of users to be indicated), the display range of the user codes and matching groups shown in the list display section 147. Furthermore, the list indication screen may allow an administrator to designate search conditions for respective items on the screen to thereby perform a search operation.

The individual data edit screen (see FIG. 35A) is used for registering, viewing, updating, displaying, and deleting data of a user. Specifically, when an administrator selects "registration" on the menu screen (not shown), the administrator terminal 2 displays an individual data edit screen blank form, which allows the administrator to enter user data and newly register it. When an administrator operates the list indication screen (see FIG. 36) to select a user, the screen transitions to the individual data edit screen, which allows the administrator to individually check data of a registered user (individual viewing), re-enter data of each item of a registered user as necessary (individual updating), and delete data of each item of a registered user as necessary (individual deleting).

Upon individual updating, when an administrator designates another shot image of a user at the face image designation section 141, a matching server generates a new face image of the user from the new shot image to thereby replace the face image registered at the time of user registration with the new face image.

The list indication screen (see FIG. 36) is used to indicate a list of user data of registered users, and allows an administrator to collectively update and collectively delete user data. Specifically, when an administrator selects "list" on the menu screen (not shown), the administrator terminal 2 displays the list indication screen (FIG. 36), which allows the administrator to check individual registered user data (individual viewing). The administrator can mark one or more checkboxes and then collectively delete user data as necessary (collective deleting). The screen may include additional checkboxes which allows an administrator to select user data on a page-by-page basis in the list.

The search screen can be used to collectively update user data of a plurality of users (collective updating). In this case, an administrator designates search conditions for target users or matching groups and operates the search button 146, and in response, the administrator terminal displays a list indication screen (FIG. 36). Then, the administrator operates the execution button 148 (collective update button) in the list indication screen. Upon collective updating, user data except user-specific data (such as users' first and last names and user codes) can be updated.

When an administrator selects "search" in the menu screen (not shown), the administrator terminal 2 displays the search screen (see FIG. 35B). Then, when the administrator enters search conditions in the search screen and operates the search button 146, the screen transitions to the list indication screen (see FIG. 36).

Figure 37:
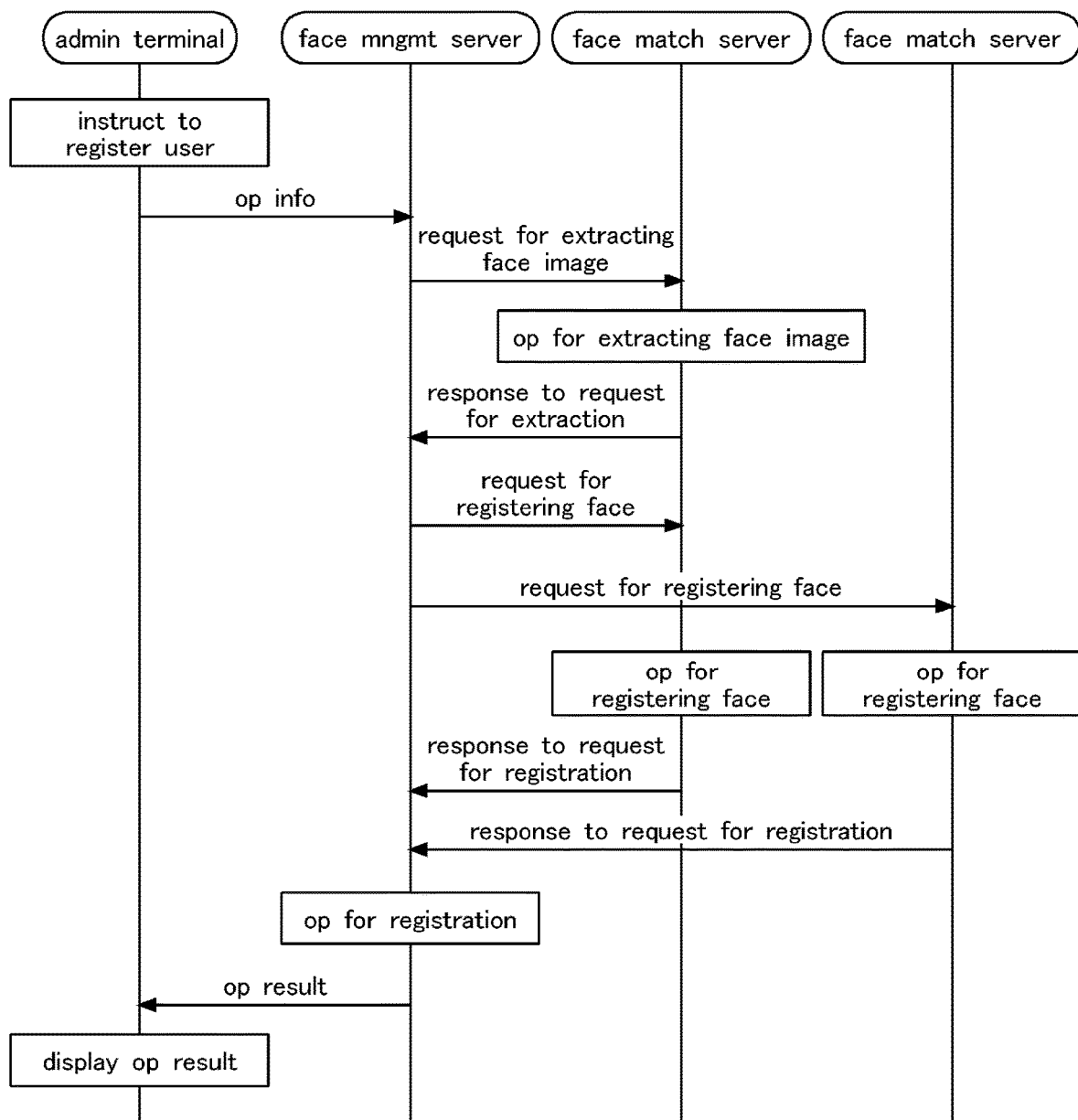
FIG. 37 is a sequence diagram showing an operation procedure of operations for registering data of a user.
Figure 38:
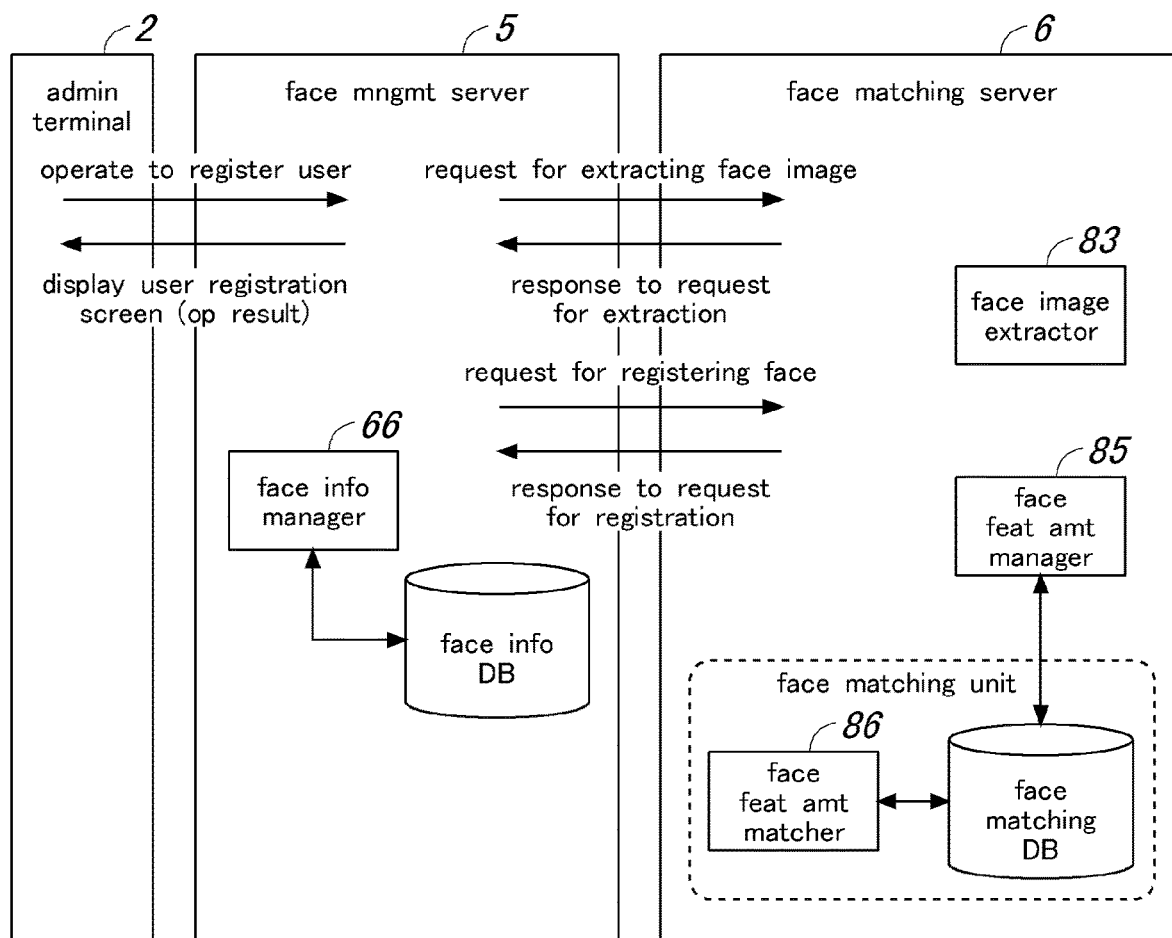
FIG. 38 is an explanatory diagram showing an outline of the operations for registering data of a user.

Next, the operations for registering user data will be described. FIG. 37 is a sequence diagram showing an operation procedure of the operations for registering data of a user. FIG. 38 is an explanatory diagram showing an outline of the operations for registering data of a user.

An administrator operates an administrator terminal 2, instructing the system to register user data. In the present embodiment, an administrator operates the individual data edit screen in the registration mode (FIG. 35A) to enter user data of a user and designate a file of a shot image of the user, and then operates the registration button.

As shown in FIG. 38, when an administrator operates an administrator terminal 2, instructing the system to register user data, the face management server 5 performs operations for registering user data of a user. In the operations for registration, the face management server 5 transmits a request for face image extraction to the face matching server which belongs to the same matching group as the target user. The request includes a shot image of the user acquired from the administrator terminal 2. When a plurality of face matching servers 6 belong to the same matching group as the target user, the face management server 5 selects one of the plurality of face matching servers 6 and transmits the request for face image extraction to the selected face matching server 6.

Upon receiving the request for face image extraction from the face management server 5, the face matching server 6 performs operations for face image extraction. The operations for face image extraction involve operations of face detection and face cut-out on the user's shot image acquired from the face management server 5 to thereby extract a face image of the user. Then, the face matching server 6 transmits a response to the request for face image extraction to the face management server 5. The response includes the face image of the user.

When receiving the response to the request for face image extraction from the face matching server 6, the face management server 5 transmits a request for face registration to each face matching server 6 which belongs to the same matching group as the target user. The request may include a user's face image acquired from one of the face matching servers 6. When a plurality of face matching servers 6 belong to the same matching group as the target user, the face management server 5 transmits requests for face registration, each request including the user's face image acquired from one of the face matching servers 6, to all the face matching servers 6 of the same matching group.

Upon receiving the request for face registration from the face management server 5, a face matching server 6 performs operations for face registration. The operations for face registration involve generating face feature amount data from the extracted face image of the user and registering the face feature amount data in the database. Upon face registration, the face matching server 6 assigns a face registration ID in association with the user's face feature amount to the user, and then transmits a response to the request for face registration to the face management server 5. The response includes an operation result indicating whether or not the operations for face registration have been normally completed, and the face registration ID. When the registration of the face feature amount data in the database is completed, the extracted face image of the user is deleted. The face feature amount data may be backed up and saved in a non-volatile memory such as an HDD or SSD provided in the face matching server 6, the non-volatile memory being separately handled from the face matching database in the face matching server 6.

When the face management server 5 receives the response to the request for face registration from the face matching server 6, the response indicating that the operations for face registration have been normally completed, the face management server 5 performs a registration operation to register user data acquired from the administrator terminal 2 in the face information database. The face management server 5 also registers the face image acquired form a face matching server 6 in the face information database. The face management server 5 also registers a face registration ID issued by the face matching server 6 in the face information database.

Next, the face management server 5 causes the administrator terminal 2 to display an operation result on the screen to indicate whether or not the operations for registering/updating user data have been normally completed. In addition, the face management server 5 records an administrator access log.

Figure 39:
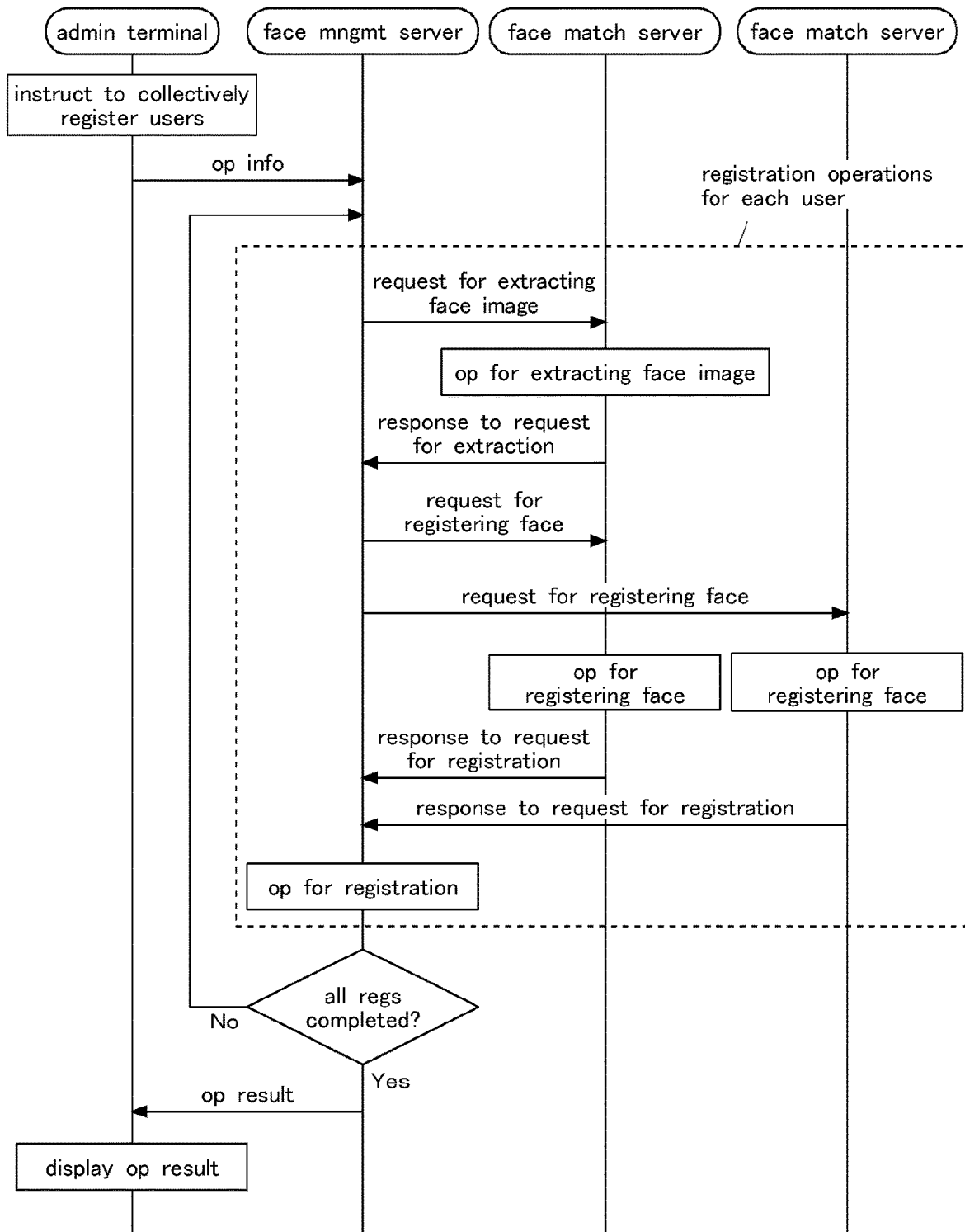
FIG. 39 is a sequence diagram showing an operation procedure of operations for collectively registering data of users.

Next, operations for collectively registering user data will be described. FIG. 39 is a sequence diagram showing an operation procedure of operations for collectively registering data of users.

In the present embodiment, the system can register users' data using a file containing list information including a list of a plurality of target users.

Specifically, an administrator operates an administrator terminal 2, instructing the administrator terminal 2 to perform the operations for collectively registering user data. In the present embodiment, an administrator operates on the registration screen (not shown) to select a file containing list information including a list of target users, and then operates a registration button.

Then, the administrator terminal 2 reads the selected file containing list information and displays the list information in the confirmation screen. The administrator confirms the registered data shown in the confirmation screen and then operates the screen, instructing to collectively registering the user data. If necessary, the administrator can modify the registered data shown in the confirmation screen.

When the administrator instructs the administrator terminal 2 to perform the operations for collectively registering user data, a face management server 5 starts the operations for collectively registering user data. The operations for collective registration involve repeatedly performing operations for registering data of each user. The registration operations for each user are the same as those for registering user data shown in FIG. 37 (individual registration operations).

The face management server 5 receives responses to requests for face registration for all the target users and the operations for collected registration are completed. Upon the completion of the operations, the face management server 5 causes the administrator terminal 2 to display an operation result indicating whether or not the collective registration operations have been normally completed, on the screen.

With regard to each user for which the server has failed to register user data, the face management server 5 reports the failure of registration to the administrator and prompts the administrator to re-register the user data. The face management server 5 outputs the registration result as a log file.

Figure 40:
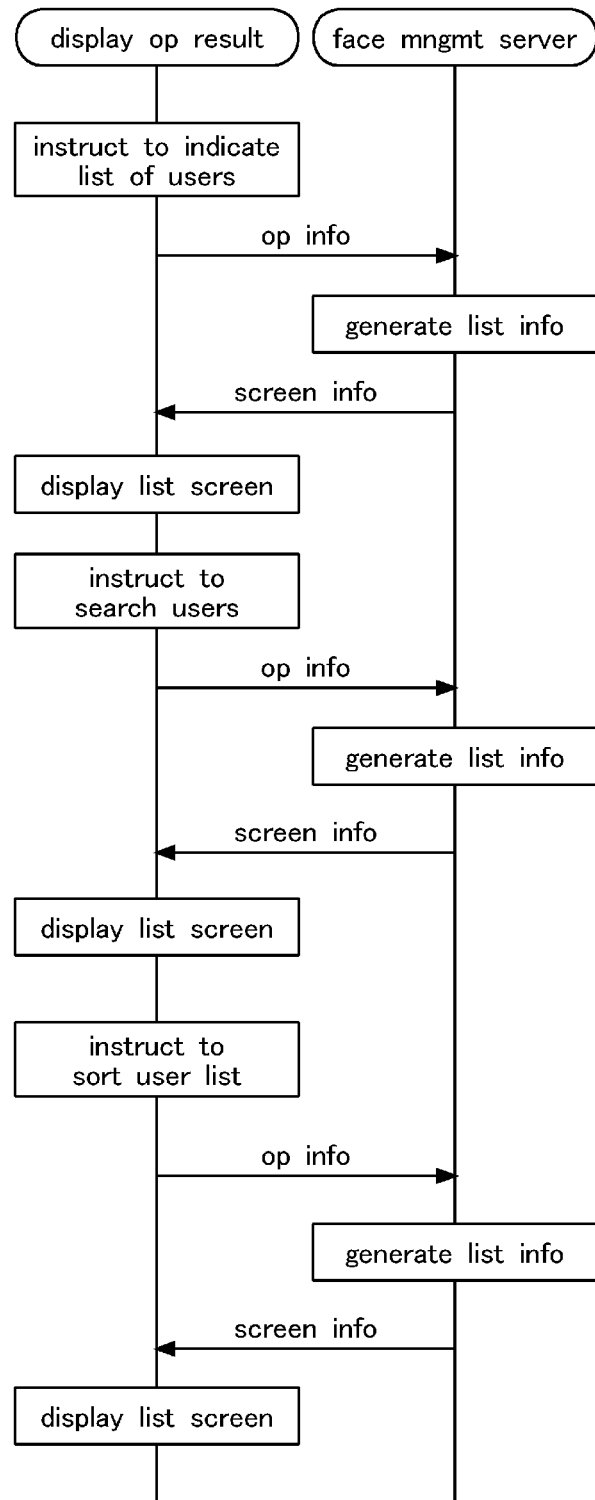
FIG. 40 is a sequence diagram showing an operation procedure of operations for viewing data of users.

Next, operations for viewing user data will be described. FIG. 40 is a sequence diagram showing an operation procedure of operations for viewing data of users.

An administrator operates an administrator terminal 2, instructing the system to indicate a list of user data. In the present embodiment, an administrator operates on the menu screen to open the list indication screen for viewing data of users (FIG. 36).

When an administrator instructs an administrator terminal 2 to indicate a list of user data, a face management server 5 creates list information including a list of all users referring to the database containing user data and, based on the list information, causes the administrator terminal to display the list indication screen (FIG. 36).

Moreover, the administrator can operate the administrator terminal 2, instructing the system to perform a search operation for searching user data. Specifically, the administrator causes the administrator terminal 2 to display the search screen (see FIG. 35B), operates the search screen to enter search conditions, and operates the search button.

When the administrator operates the administrator terminal 2, instructing the system to perform the search operation for searching user data, the face management server 5 creates list information including a list of user data which meets the search conditions referring to the database, and causes the administrator terminal to display the list indication screen (FIG. 36) indicating a search result based on the list information.

Furthermore, the administrator can operate the administrator terminal 2, instructing the system to perform a sort operation for sorting the list of user data. Specifically, the administrator operates the administrator terminal 2 to designate an item in the list indication screen and then instructs the system to perform the sort operation.

When the administrator operates the administrator terminal 2, instructing the system to perform the sort operation, the face management server 5 creates user list information including a sorted list of user data, and causes the administrator terminal 2 to display the list indication screen indicating the sorted list of user data based on the user list information.

When the administrator operates the list indication screen (FIG. 36) to select a user, and then instructs the system to perform an individual indication operation for indicating data of the selected user, the face management server 5 acquires user data of the selected user referring to the database, and causes the administrator terminal 2 to display the individual data edit screen (see FIG. 35A).

Figure 41:
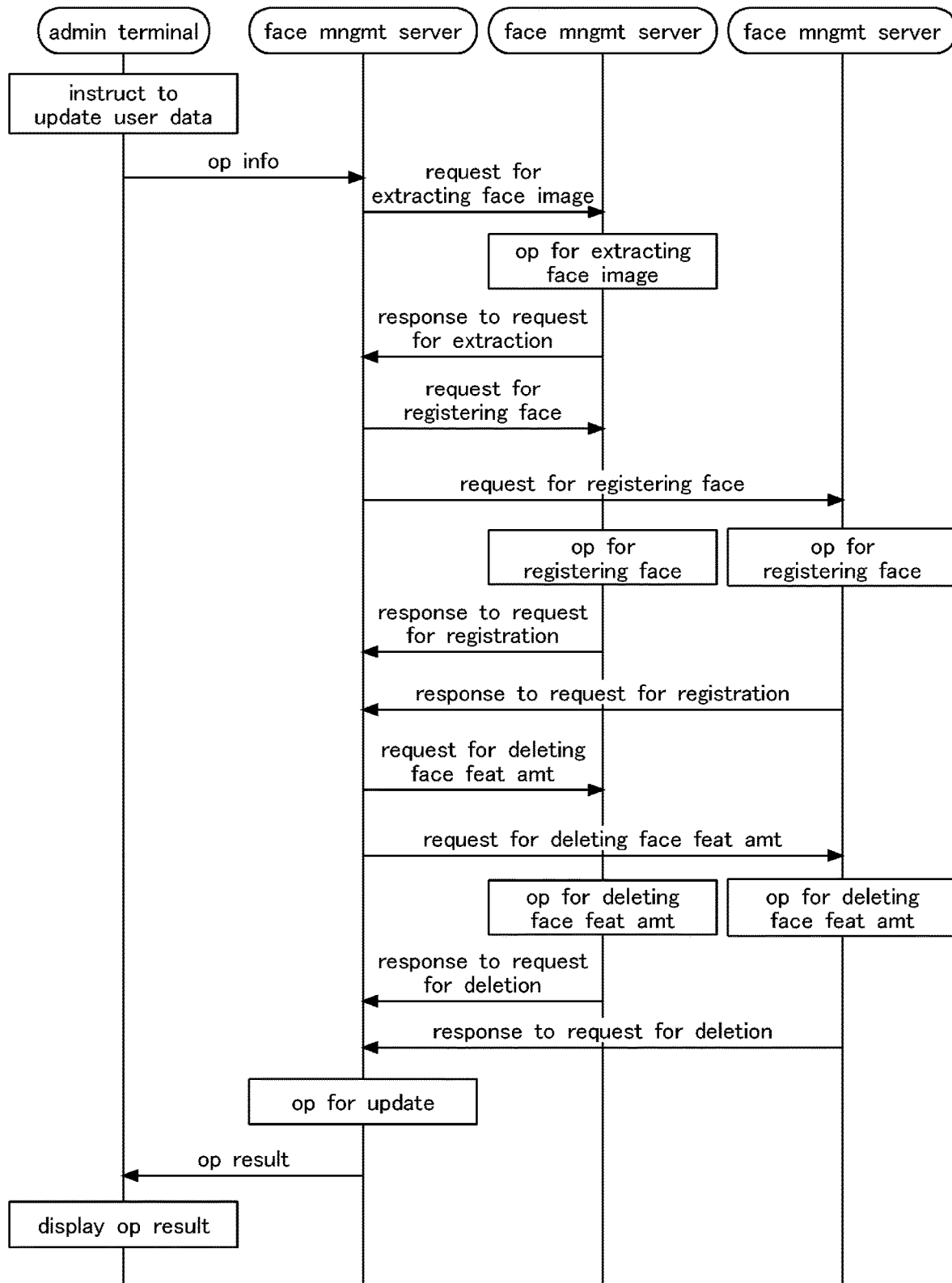
FIG. 41 is a sequence diagram showing an operation procedure of operations for updating data of a user.
Figure 42:
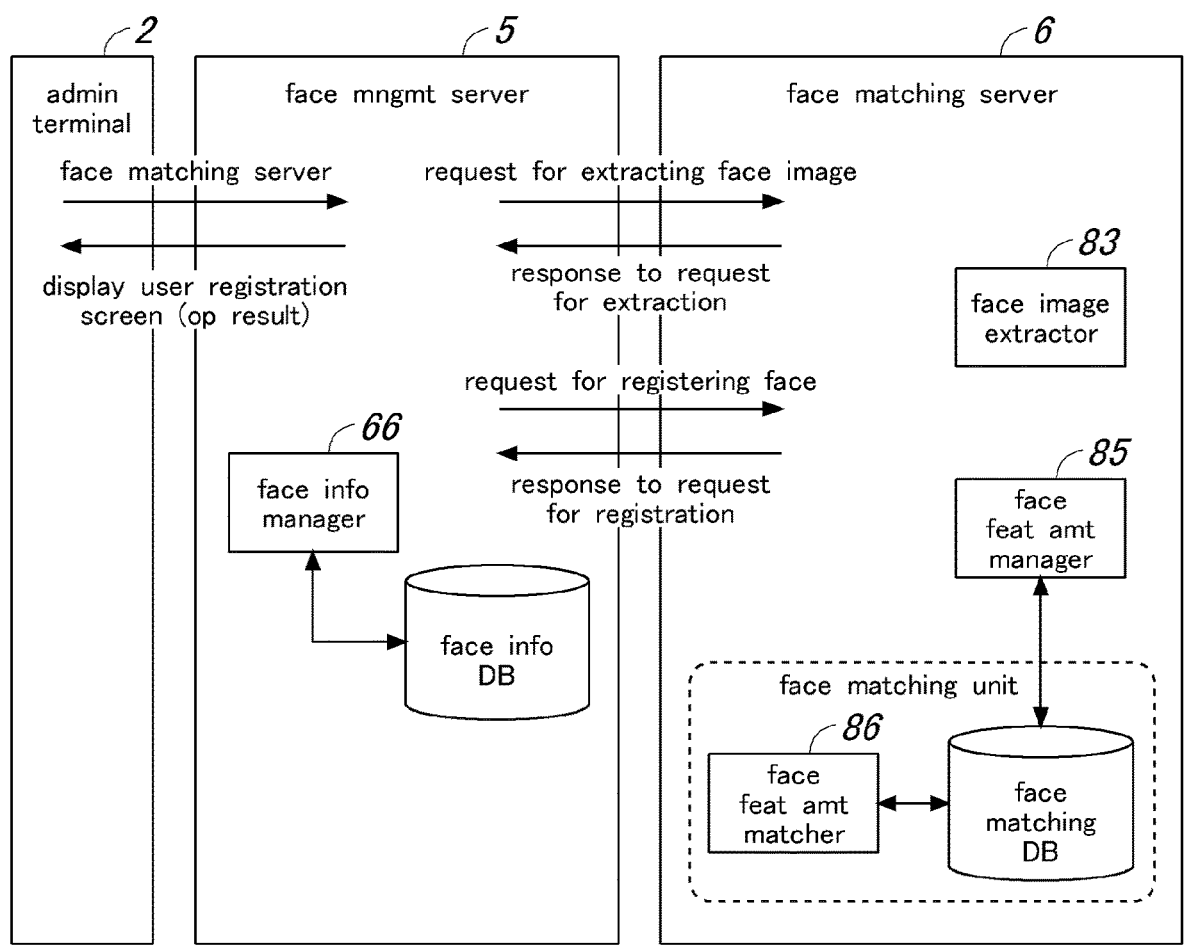
FIG. 42 is an explanatory diagram showing an outline of the operations for updating data of a user.

Next, the operations for updating user data will be described. FIG. 41 is a sequence diagram showing an operation procedure of the operations for updating data of a user. FIG. 42 is an explanatory diagram showing an outline of the operations for updating data of a user.

First, operations for changing a shot image of a user will be described. In this case, an administrator operates an administrator terminal 2, instructing the system to perform the operation for updating user data. In the present embodiment, an administrator operates the individual data edit screen (not shown) in the update mode to re-enter data of a user and replace a file of a shot image of the user, and then operates the update button.

As shown in FIG. 42, when an administrator operates an administrator terminal 2, instructing the system to perform the operation for updating user data, the face management server 5 performs operations for updating data of a user. In the update operations, the face management server 5 transmits a request for face image extraction to the face matching server which belongs to the same matching group as the target user. The request includes a shot image of the user acquired from the administrator terminal 2. When a plurality of face matching servers 6 belong to the same matching group as the target user, the face management server 5 selects one of the plurality of face matching servers 6 and transmits the request for face image extraction to the selected face matching server 6.

Upon receiving the request for face image extraction from the face management server 5, the face image extractor of the face matching server 6 performs operations for face image extraction. The operations for face image extraction involve operations of face detection and face cut-out on the user's shot image acquired from the face management server 5 to thereby extract a face image of the user. Then, the face matching server 6 transmits a response to the request for face image extraction to the face management server 5. The response includes the face image of the user.

When receiving the response to the request for face image extraction from the face matching server 6, the face management server 5 transmits a request for face registration to each face matching server 6 which belongs to the same matching group as the target user. The request may include a user's face image acquired from one of the face matching servers 6. When a plurality of face matching servers 6 belong to the same matching group as the target user, the face management server 5 transmits requests for face registration, each request including the user's face image acquired from one of the face matching servers 6, to all the face matching servers 6 of the same matching group.

Upon receiving the request for face registration from the face management server 5, a face matching server 6 performs operations for face registration. The operations for face registration involve generating face feature amount data from the extracted face image of the user and registering the face feature amount data in the database. Upon face registration, the face matching server 6 generates a face registration ID associated with the face feature amount data of the user, and then transmits a response to the request for face registration to the face management server 5. The response includes an operation result indicating whether or not the operations for face registration have been normally completed, and the face registration ID.

When the face management server 5 receive the response to the request for face registration from the face matching server 6, the response indicating that the operations for face registration have been successfully completed, the face management server 5 transmits a request for face feature amount deletion to the face matching server 6 which belongs to the same matching group as the target user. When the response indicates that the face matching server 6 has unsuccessfully complete the operations for face registration, the face management server 5 does not make a request for face feature amount deletion to the face matching server 6 so that face matching is performed using the old face feature amount.

Upon receiving the request for face feature amount deletion from the face management server 5, the face matching server 6 performs a face feature amount deletion operation. The face feature amount deletion operation involves deleting the old face feature amount data of the target user from the database. Then, the face matching server 6 transmits a response to the request for face feature amount deletion to the face management server 5. The response includes an operation result indicating whether or not the face feature amount deletion operation has been normally completed.

Upon receiving the response to the request for face feature amount deletion from the face matching server 6, the response indicating that the operations for face feature amount deletion has been normally completed, the face management server 5 performs an update operation to update use data. The update operation involves updating data in the face information database with new user data acquired form the administrator terminal 2. The face management server 5 also registers a face image acquired form a face matching server 6 in the face information database. Moreover, the face management server 5 registers a new face registration ID issued by the face matching server 6 in the face information database; that is, deletes the old face registration ID from the database and registers the new face registration ID in place of the old one.

Next, the face management server 5 causes the administrator terminal 2 to display an operation result on the screen to indicate whether or not the operations for updating user data have been normally completed. In addition, the face management server 5 records an administrator access log.

Next, operations for updating user data without changing a shot image of a user (i.e., operations for making a change in items other than the shot image) will be described. In this case, an administrator operates an administrator terminal 2, instructing the system to perform the operation for updating user data. In the present embodiment, an administrator operates the individual data edit screen (not shown) in the in update mode to re-enter data of a user, and then operates the update button.

When an administrator operates an administrator terminal 2, instructing the system to perform the operation for updating user data, the face management server 5 performs operations for updating data of a user. In the update operations, the face management server 5 updates user data in the face information database with the user data newly entered by the administrator. Then, the face management server 5 causes the administrator terminal 2 to display an operation result on the screen to indicate whether or not the operations of updating user data have been normally completed. In addition, the face management server 5 records an administrator access log.

Figure 43:
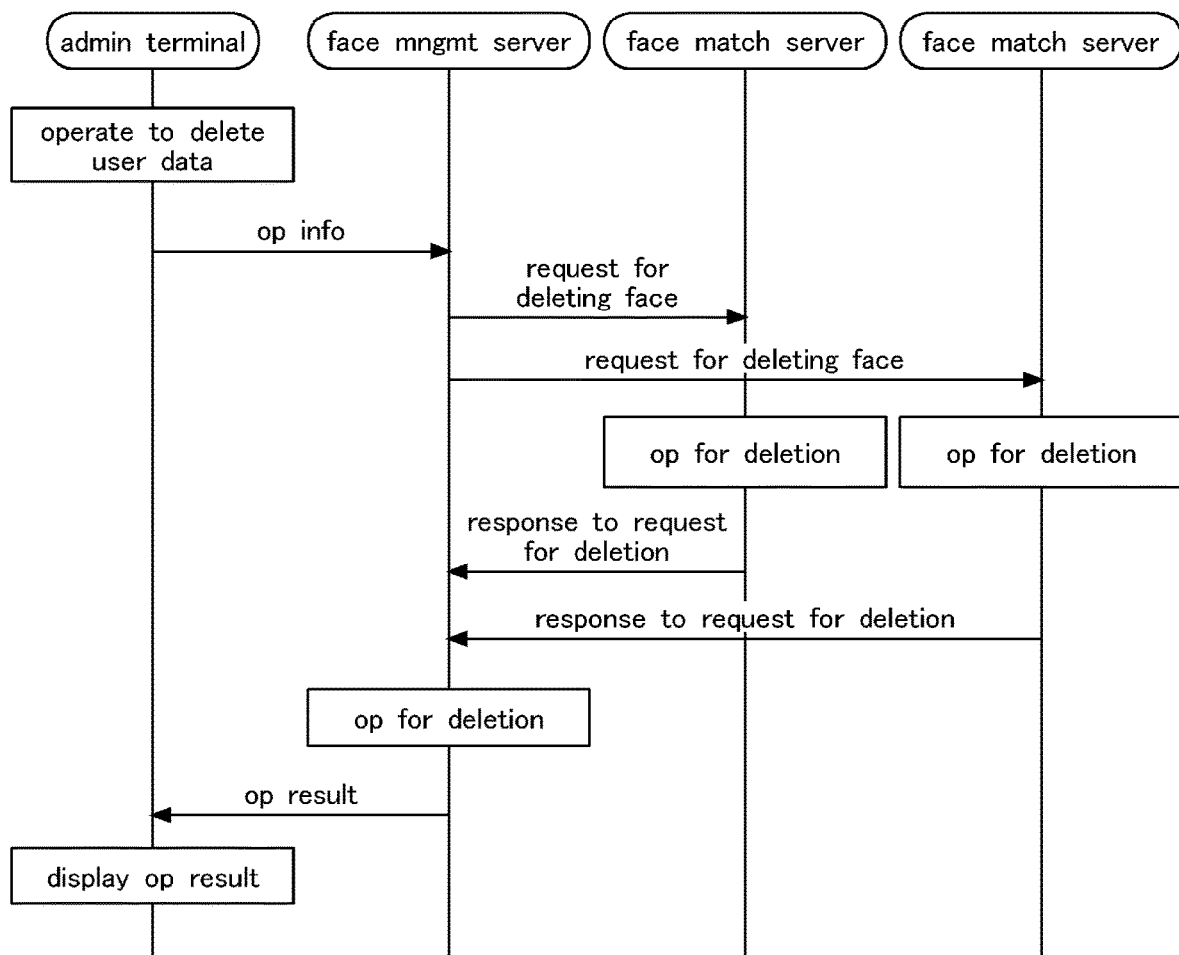
FIG. 43 is a sequence diagram showing an operation procedure of operations for deleting data of a user.
Figure 44:
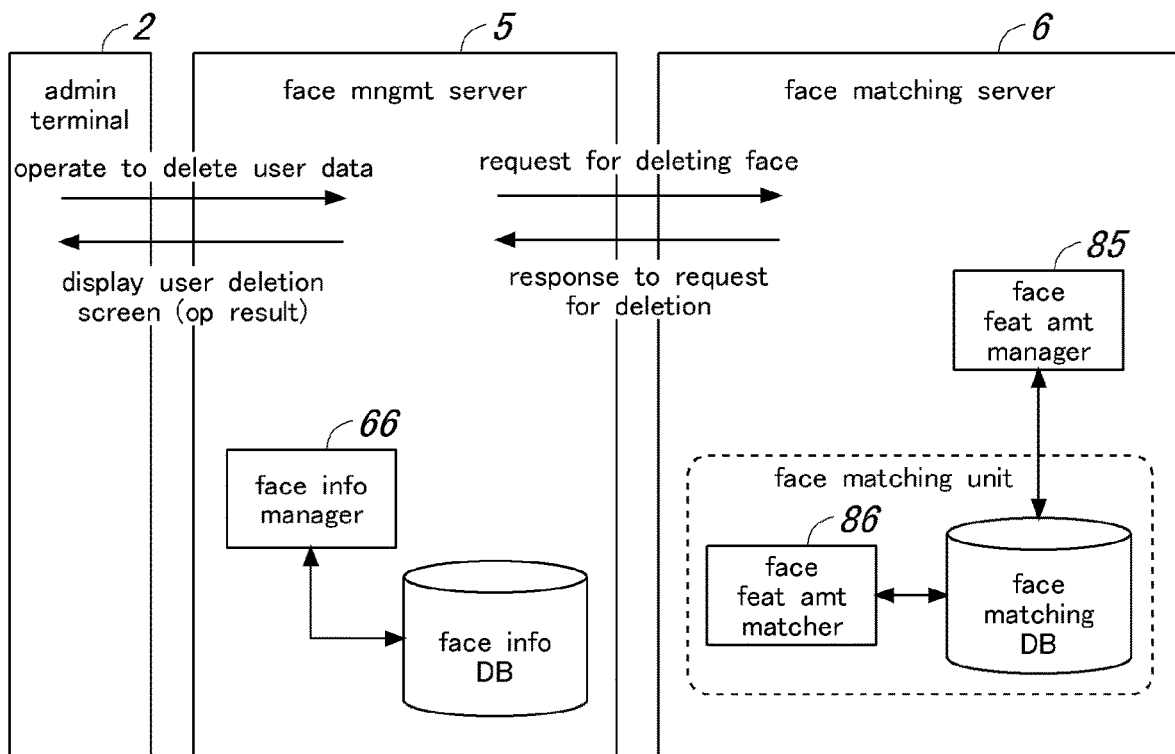
FIG. 44 is an explanatory diagram showing an outline of the operations of deleting data of a user.

Next, the operations for deleting user data will be described. FIG. 43 is a sequence diagram showing an operation procedure of the operations for deleting data of a user. FIG. 44 is an explanatory diagram showing an outline of the operations of deleting data of a user.

An administrator operates an administrator terminal 2, instructing the system to perform the operation for deleting user data. In the present embodiment, an administrator selects a target user, thereby causing the administrator terminal 2 to display the individual data edit screen in the deletion mode (not shown), and then operates the deletion button in the screen. In some cases, the administrator selects a plurality of target users in the list indication screen in the deletion mode (not shown), and then operates a collective deletion button.

As shown in FIG. 44, when an administrator operates an administrator terminal 2, instructing the system to perform the operations for deleting user data, the face management server 5 starts operations for deleting data of a user. In the deletion operations, the face management server 5 transmits a request for face deletion to the face matching server which belongs to the same matching group as the target user. When a plurality of face matching servers 6 belong to the same matching group as the target user, the face management server 5 transmits the request for face deletion to all the face matching servers 6 of the same matching group.

Upon receiving the request for face deletion from the face management server 5, a face matching server 6 performs operations for deleting the face data of the target user. The face deletion operations involve deleting the user data (face feature amount data) of the user from the database.

When the operations for deletion are completed, the face matching server 6 transmits a response to the request for user data deletion to the face management server 5. The response includes an operation result indicating whether or not the operations for deletion have been normally completed.

When the face management server 5 receives the response to the request for face deletion from the face matching server 6, the response indicating that the operations for face deletion have been normally completed, the face management server 5 performs a deletion operation for deleting user data to delete the data of the target user in the face information database. When the deletion operation is completed, the face management server 5 causes the administrator terminal 2 to display an operation result on the screen indicating whether or not the operations for deleting user data have been normally completed. In addition, the face management server 5 records an administrator access log.

Figure 45:
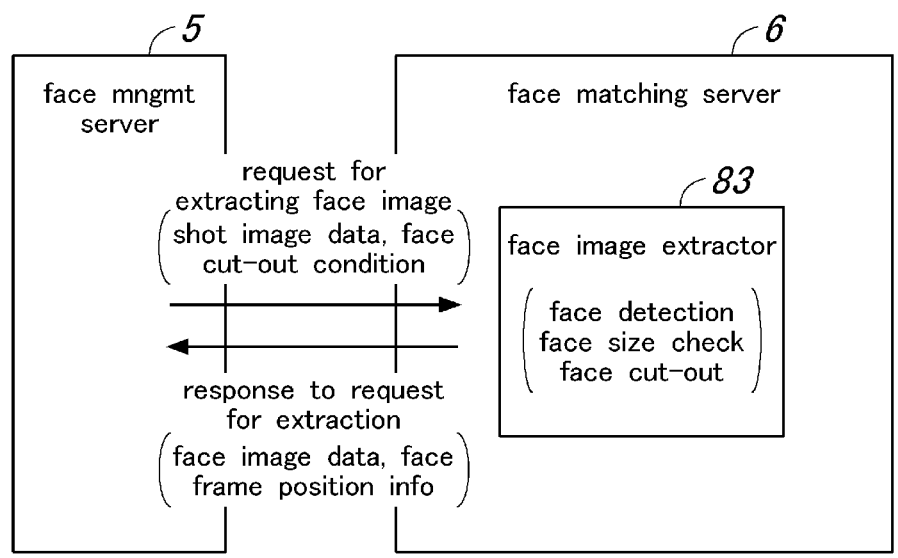
FIG. 45 is an explanatory diagram showing an outline of operations for extracting a face image.

Next, operations for face image extraction performed by a face matching server 6 will be described. FIG. 45 is an explanatory diagram showing an outline of operations for extracting a face image.

A face management server 5 transmits a request for face image extraction to the face matching server 6. The request for face image extraction includes data of a shot image of a user and face cut-out conditions (face image extraction conditions). The face cut-out conditions are parameters used in the operations for face image extraction (face detection, face size check, face cut-out). More specifically, the face cut-out conditions includes the number of faces to be adopted when two or more faces are detected, the face detection method (which is used as a basis for detecting a face, an area of a face frame or a height of a face frame), and respective higher and lower limits of the width and the height of a face frame as references for face detection (face size check threshold values).

Upon receiving the request for face image extraction from the face management server 5, the face image extractor 83 of the face matching server 6 performs operations for face image extraction; that is, operations for extracting a face image of a user. The operations for face image extraction involve operations for face detection, face size check, and face cut-out. Then, the face matching server 6 transmits a response to the request for face image extraction to the face management server 5. The response includes an image data(s) and face frame position information (coordinates of the upper left vertex, width and height of each face frame).

The face image extractor-83 of a face matching server 6 performs the same operations as the face image extractor 22 of a face authentication machine. First, the face image extractor 83 detects a face region from the shot image (face detection). When the shot image includes a plurality of face regions, the face image extractor 83 selects some of the face regions based on an area and a width of each face region. Next, the face image extractor 83 determines whether or not each detected face region (face frame) meets predetermined conditions, or falls within an appropriate size range (face size check). Then, the face image extractor 83 determines a cut-out region of an image captured by a camera 11 based on the face region(s) (face frame(s)) detected by the face detection operation, and cuts out the determined cut-out region as a face image (face cut-out), thereby providing face image data.

Figure 46:
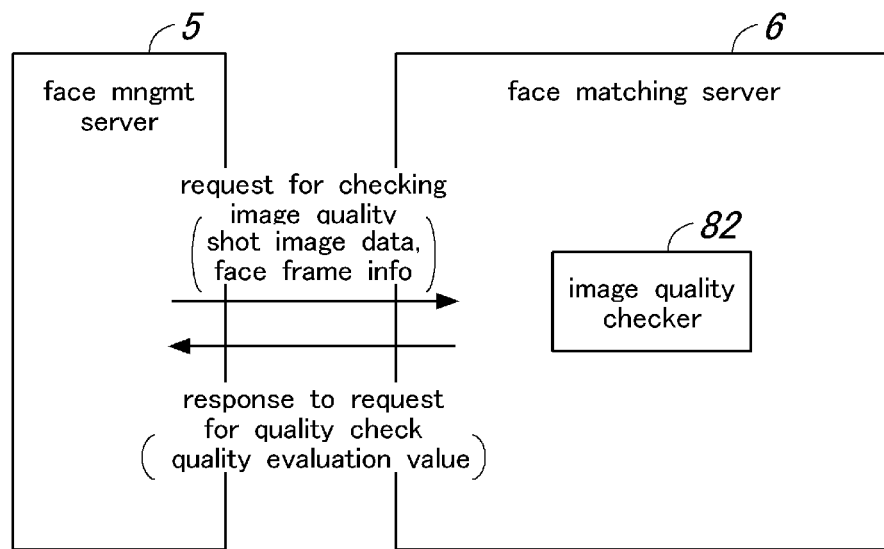
FIG. 46 is an explanatory diagram showing an outline of operations for checking image quality.

Next, operations for checking image quality performed by a face matching server 6 will be described. FIG. 46 is an explanatory diagram showing an outline of operations for checking image quality.

The image quality checker 82 of the face matching server 6 determines whether or not the image of a face region (face frame) detected in the captured image data meets a predetermined quality level. Specifically, the image quality checker 82 detects whether or not a person in the image wears a mask and whether or not the person wears sunglasses. The image quality checker 82 also calculates the degree of face authentication suitability from the image. The degree of face authentication suitability is an evaluation value based on face orientation and facial expression of a person in the shot image.

In the operations for checking image quality, a face management server 5 transmits a request for image quality check to the face matching server 6. The request for image quality check includes shot image data and face frame information.

Upon receiving the request for image quality check from the face management server 5, the image quality checker 82 of the face matching server 6 determines whether or not the image of a face region (face frame) in the captured image meets a predetermined quality level, and calculates a quality evaluation value. Then, the face matching server 6 transmits a response to the request for image quality check to the face management server 5. The response includes the calculated quality evaluation value.

Figure 47:
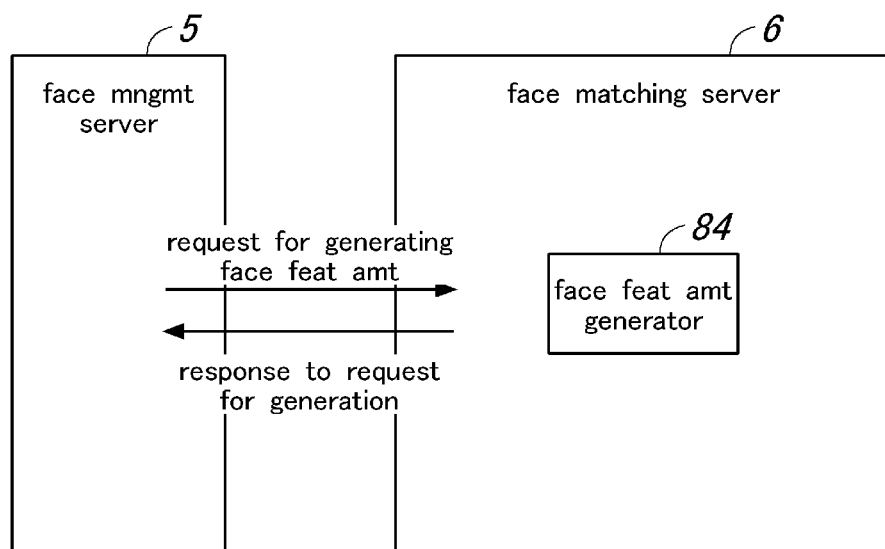
FIG. 47 is an explanatory diagram showing an outline of operations for calculating a face feature amount.

Next, operations for face feature amount generation performed during face registration will be described. FIG. 47 is an explanatory diagram showing an outline of operations for generating a face feature amount.

The face feature amount generator 84 of a face matching server 6 generates face feature amount data from the user's face image data extracted in the earlier operations, and stores the face feature amount data in the face matching DB.

In the operations for face feature amount generation, first, a face management server 5 or a face authentication machine 1 transmits a request for face feature amount generation to a face matching server 6.

Upon receiving the request for face feature amount generation from the face management server 5, the face feature amount generator 84 of the face matching server 6 generates face feature amount data from the image of the face region extracted in the earlier operations. Then, the face matching server 6 transmits a response to the request for face feature amount generation to the face management server 5.

Figure 48:
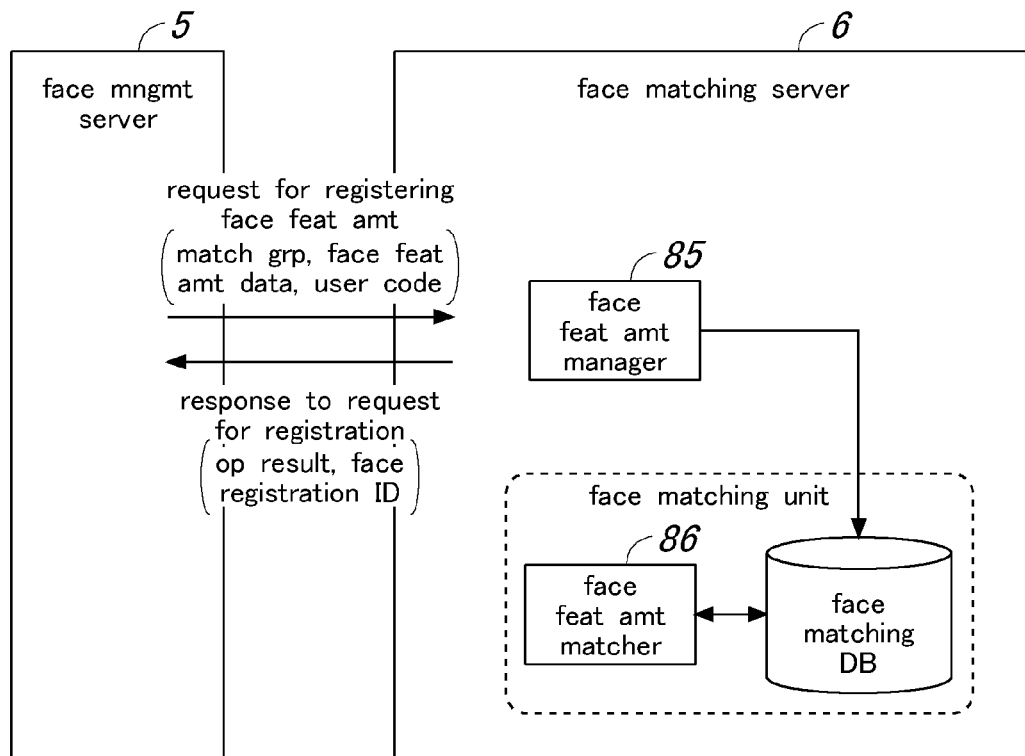
FIG. 48 is an explanatory diagram showing an outline of operations for registering a face feature amount (face feature amount based)
Figure 49:
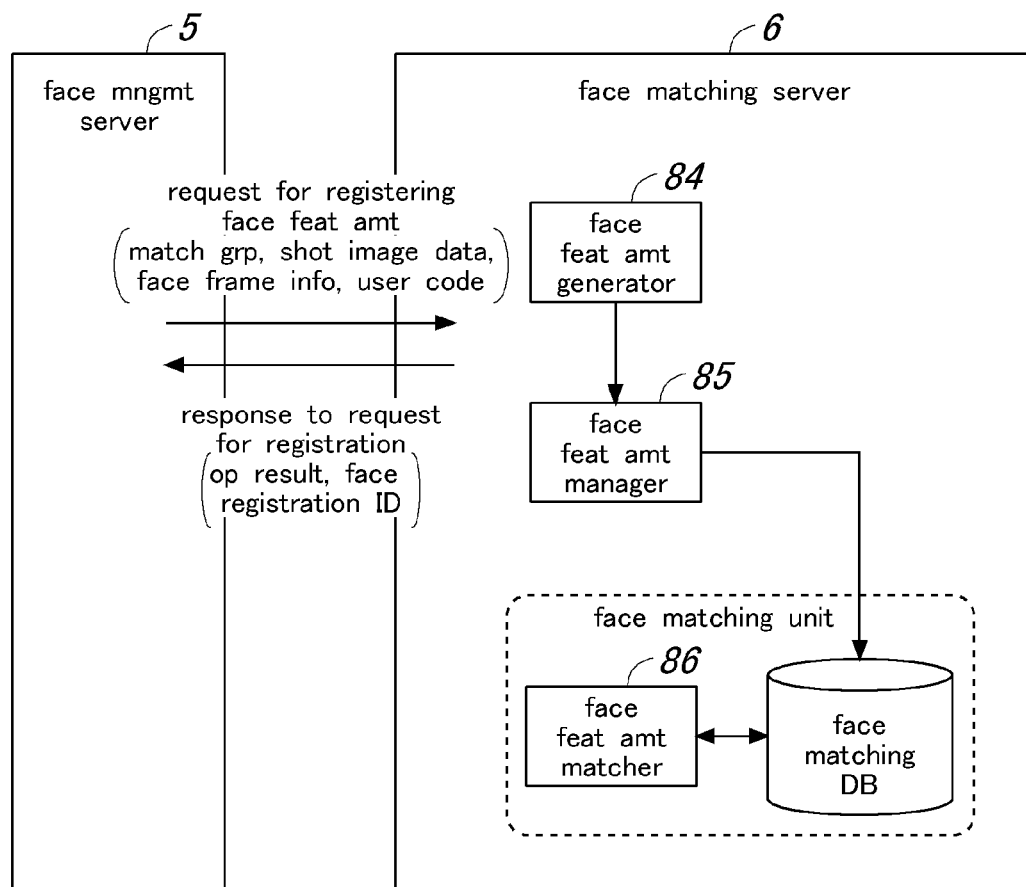
FIG. 49 is an explanatory diagram showing an outline of operations for registering a face feature amount (image based)

Next, face feature amount registration operations performed at the time of face registration will be described. FIG. 48 is an explanatory diagram showing an outline of operations for registering a face feature amount (face feature amount based registration). FIG. 49 is an explanatory diagram showing an outline of operations for registering a face feature amount (image based registration).

The face matching server 6 has the functions of face image extraction and face feature amount generation, and performs respective operations for face image extraction and face feature amount generation in response to a request from the face management server 5. When a plurality of face matching servers 6 belong to the same matching group of a user, face feature amount data of the user needs to be registered in the face matching databases of all those face matching servers 6.

In some embodiments, after one of the face matching servers 6 performs the operations of face image extraction and face feature amount generation, respectively, the face management server 5 can acquire the generated face feature amount and provide it to the remaining face matching servers 6, thereby registering face feature amount data of the user in the face matching databases of all the face matching servers 6. In this case, first, the face management server 5 receives a response to a request for face feature amount generation from one of the face matching servers 6 to thereby acquire face feature amount data included in the response, and then the face management server 5 adds the acquired face feature amount data to a request for face feature amount registration and transmits the request to each of the remaining face matching servers 6 (face feature amount based face feature amount registration).

In other embodiments, after one of the face matching servers 6 performs the operations of face image extraction, the face management server 5 can acquire the extracted image data and provide it to the remaining face matching servers 6, whereby each face matching server 6 can perform the operations of face feature amount generation, thereby registering face feature amount data of the user in the face matching databases of all the face matching servers 6. In this case, first, the face management server 5 receives a response to a request for face image extraction from one of the face matching servers to thereby acquire face image data included in the response, and then the face management server 5 adds the acquired face image data to a request for face feature amount registration and transmits the request to each of the remaining face matching servers 6 (image based face feature amount registration).

As shown in FIG. 48, in the case of face feature amount-based face feature amount registration, the face management server 5 first transmits a request for face feature amount registration to a face matching server 6. This request includes the matching group, face feature amount data, and user code of a user.

When receiving the face feature amount registration request from the face management server 5, the face feature amount manager 85 of the face matching server 6 registers the user's face feature amount data included in the request in the face matching database. Upon face registration, the face feature amount manager 85 registers the face feature amount data in the face matching database of a face matching unit which belongs to the same matching group as the user. The face matching server 6 assigns a registrant code to a user whose face registration has been completed. The face matching server 6 registers the registrant code in association with the face feature amount in the face matching database.

When the operation for face feature amount registration is completed, the face matching server 6 transmits a response to the request to the face management server 5. The response includes an operation result indicating whether or not the operation for face registration has been normally completed, and the face registration ID (registrant code).

As shown in FIG. 49, in the case of image-based face feature amount registration, the face management server 5 first transmits a request for face feature amount registration to a face matching server 6. This request includes the matching group, face frame information, and user code of a user.

When receiving the face feature amount registration request from the face management server 5, the face feature amount generator 84 of the face matching server 6 generates face feature amount data from the user's face image data (shot image data and face frame information) included in the request, and the face feature amount manager 85 registers the generated face feature amount data in the face matching database. Upon face registration, the face feature amount manager 85 registers the face feature amount data in the face matching database of a face matching unit which belongs to the same matching group as the user. The face matching server 6 assigns a registrant code to a user whose face registration has been completed. The face matching server 6 registers the registrant code in association with the face feature amount in the face matching database.

Then, the face matching server 6 transmits a response to the request for face feature amount registration to the face management server 5. The response includes an operation result indicating whether or not the operations for face registration have been normally completed, and the face registration ID.

Figure 50:
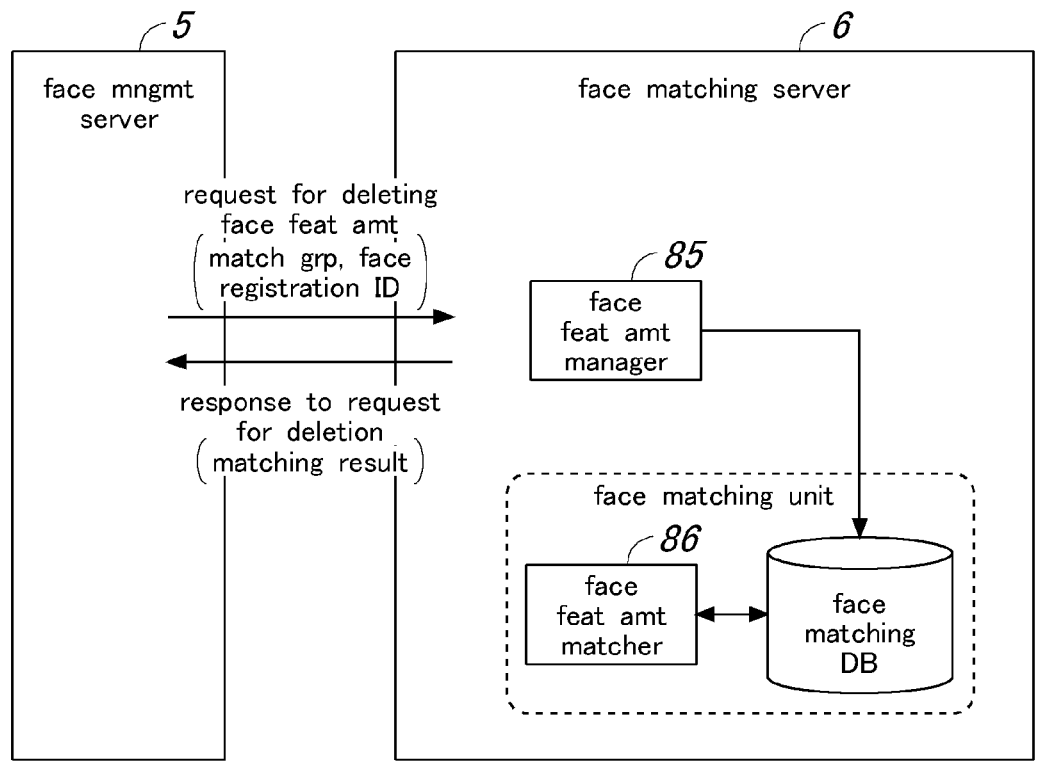
FIG. 50 is an explanatory diagram showing an outline of operations for deleting a face feature amount.

Next, operations for deleting a face feature amount performed in the operations for updating and deleting user data will be described. FIG. 50 is an explanatory diagram showing an outline of operations for deleting a face feature amount.

When user data is deleted, face feature amount data of a target user is deleted from the face matching database of a face matching server 6. When user data is updated, the old face feature amount data of a target user is deleted from the face matching database of a face matching server 6. When face feature amount data of a user is deleted, the other user data of the user and data on an association between face feature amount data and the user are also deleted.

Specifically, first, a face management server 5 transmits a request for face feature amount deletion to a face matching server 6. The request includes a matching group and a face registration ID of a user.

When receiving the face feature amount deletion request from the face management server 5, the face feature amount manager 85 of the face matching server 6 identifies the user based on the face registration ID included in the request, and deletes the face feature amount data of the user from the face matching database. When the user belongs to a plurality of matching groups, the face feature amount manager 85 performs a face feature amount deletion operation for each matching group. In other words, the face feature amount manager 85 deletes the target user's face feature amount data from face matching databases of the respective matching groups.

When the face feature amount deletion operation is completed, the face matching server 6 transmits a response to the request for face feature amount deletion to the face management server 5. The response includes an operation result indicating whether or not the deletion operation has been normally completed.

Figure 51:
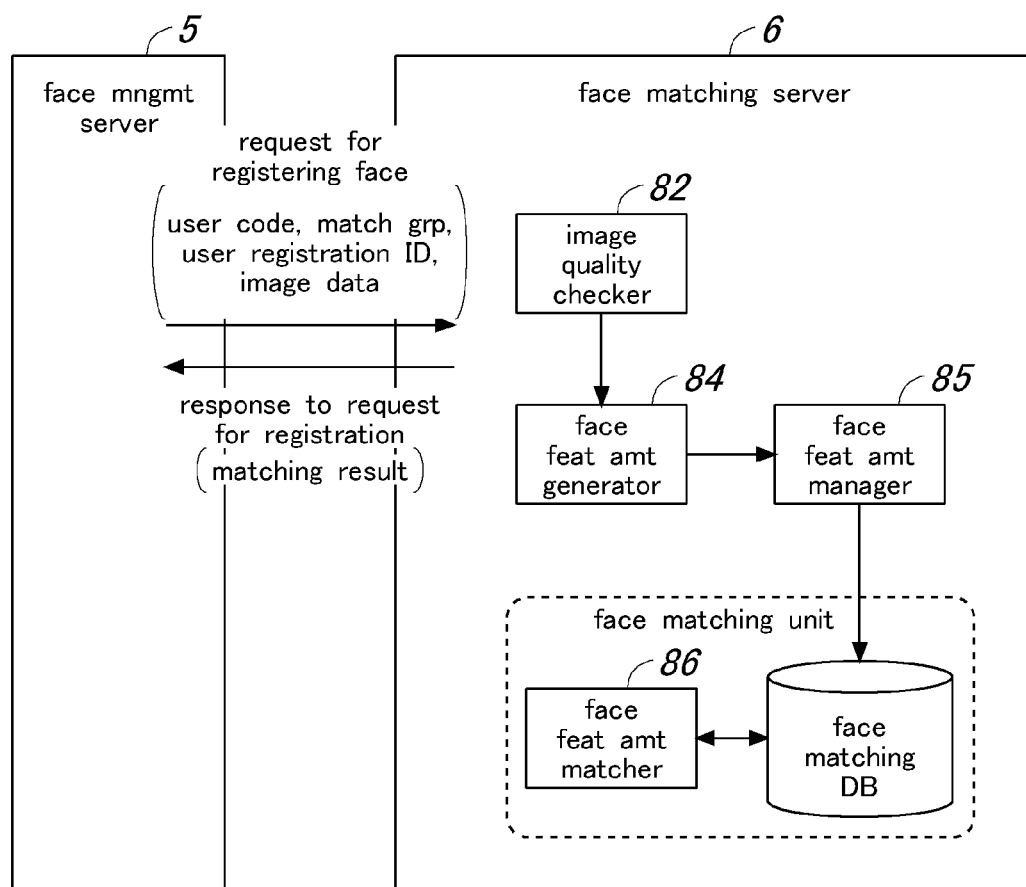
FIG. 51 is an explanatory diagram showing an outline of operations for registering a face (face data)

Next, operations for registering a face performed in the operations for registering user data will be described. FIG. 51 is an explanatory diagram showing an outline of operations for registering a face (face data).

Upon registration of user data, first, a face management server 5 transmits a request for face image extraction to a face matching server 6, acquires face image data from the face matching server 6, and registers it in the face information database. Then, the face management server 5 provides face image data to the face matching server 6 and causes the face matching server 6 to perform the operations for face registration. In the operations for face registration, the face matching server 6 generates face feature amount data from face image data acquired from the face management server 5 and registers the generated face feature amount data in the face matching database.

Specifically, first, the face management server 5 transmits a request for face registration to a face matching server 6. The request includes the user code, matching group, user registration ID of a user.

Upon receiving the face registration request from the face management server 5, the image quality checker 82 of the face matching server 6 performs operations for checking image quality on the user's face image included in the request. Next, the face feature amount generator 84 generates face feature amount data from the user's face image data, and then the face feature amount manager 85 registers the face feature amount data in a face matching database of the same matching group as the user. Simultaneously, the face feature amount manager 85 stores the user registration ID to be used in the face information database of the face management server 5 and the data of an association between the user registration ID at the time of face feature amount registration and the user's face feature amount data to be used in the face matching database of the face matching server 6. When the user registration ID of the user has already been registered, the face feature amount manager 85 deletes the old face feature amount data and registers the new face feature amount data in place of the ole one. The face feature amount manager 85 also registers the user code of the user as user data in the face matching database.

Upon completion of the operations for registering face feature amount data in the face matching databases for all the matching groups to which the user belongs, the face matching server 6 transmits a response to the request for face registration to the face management server 5. The response includes an operation result indicating whether or not the operations for registration have been normally completed.

Figure 52:
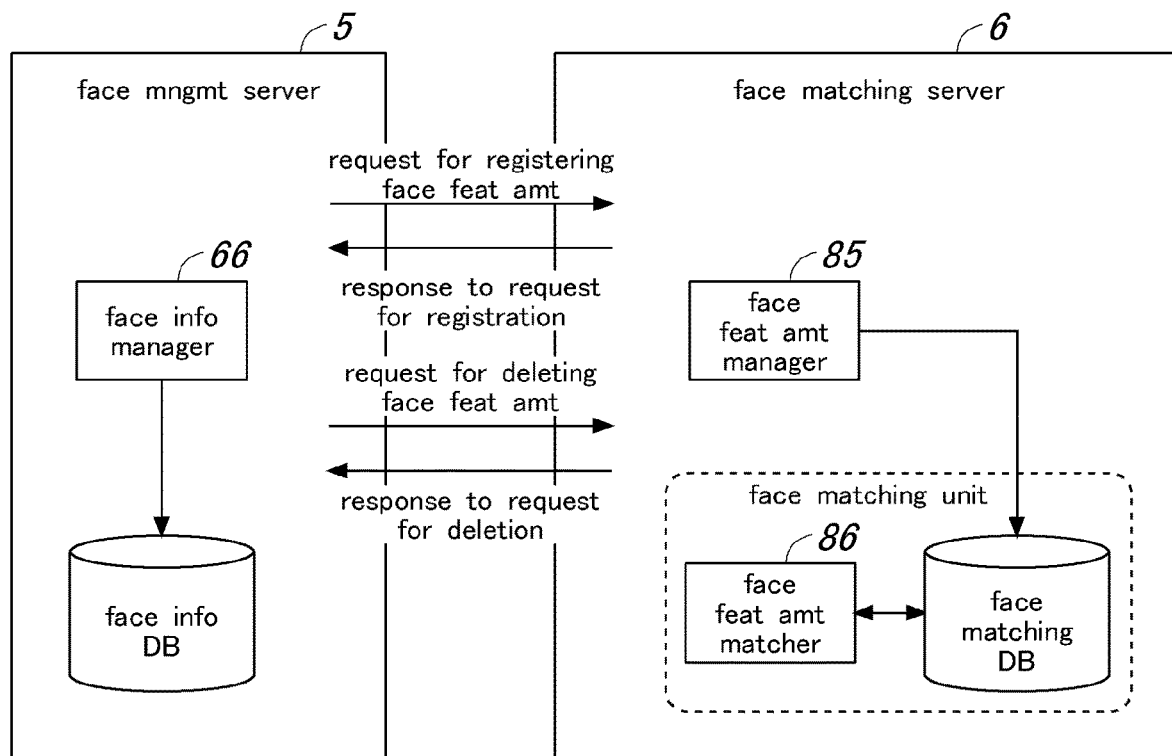
FIG. 52 is an explanatory diagram showing an outline of operations for synchronizing face information.

Next, operations of synchronizing face information performed by a face management server 5 will be described. FIG. 52 is an explanatory diagram showing an outline of operations for synchronizing face information.

The face information manager 66 of the face management server 5 performs the operations for synchronization with the face matching server 6. The operations for synchronization bring the registered data in the face information database of the face management server 5 in synchronization with the registered data in the face matching database of the face matching server 6. Specifically, the face information manager 66 brings the user data (face image data) registered in the face information database of the face management server 5 in synchronization with the users' face feature amount data registered in the face matching database of the face matching server 6. In addition, the face information manager 66 keeps the data of matching groups registered in the face management server 5 corresponding to that registered in the face matching server(s) 6.

With regard to the timing of performing the operations for synchronization, the face information manager 66 periodically performs the operations for synchronization at a predetermined period of time. In addition, the face information manager 66 performs the operations for synchronization when user data is registered, updated, and deleted. The face information manager 66 also performs the operations for synchronization when a matching group is deleted or when a face matching server 6 is started up.

With regard to the scope of user data on which the operations for synchronization are performed, the operations for synchronization may be performed on user data of all the users. In other cases, the operations for synchronization may be performed on user data of the designated users. The operations for synchronization may be performed on user data updated during a designated period of time.

In the present embodiment, the activation date and the validation date for each user are registered as part of user data. An activation date is the date on which face matching of a user is enabled. During an activated period after this activation date, face authentication is performed on the activated user and face authentication is available to the user. An invalidation date is the date on which face matching is disabled. During an invalidated period after the invalidation date, face authentication is not performed on the invalidated user and face authentication is no longer available to the user.

For all the users, the face information manager 66 of the face management server 5 performs the operations to determine whether or not each user is activated or invalidated, in order to determine time to perform the operations for synchronization. When face matching is activated for a user and an activated period starts, the face information manager 66 instructs a face matching server 6 to perform operations for registering face feature amount data of the user. When face matching is invalidated for a user and an invalidation period starts, the face information manager 66 instructs the face matching server 6 to perform the face deletion operations; that is, the operations for deleting the face feature amount data of the user. As a result, during any period before the activation date and any period after the invalidation date, no face information (face feature amount data) of a user is stored in a face matching server 6.

A face management server 5 determines whether or not a certain operation has been normally completed in a face matching server 6. When determining that the operation fails in a face matching server 6 and needs to be re-executed, the face management server 5 instructs the face matching server 6 to re-execute the operation. The operations on which a face management server 5 makes such determinations, include operations for face registration, face deletion, matching group registration, and matching group deletion.

In addition, the face management server 5 records a synchronization log (history information on operations for synchronization).

Figure 53A:
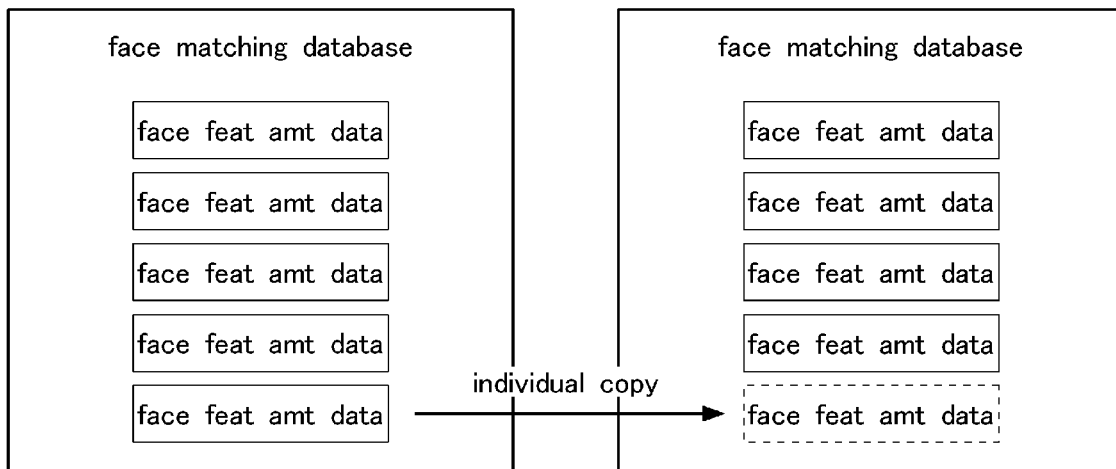
FIGS. 53A-B are explanatory diagrams showing outlines of operations for copying face feature amount data.
Figure 53B:
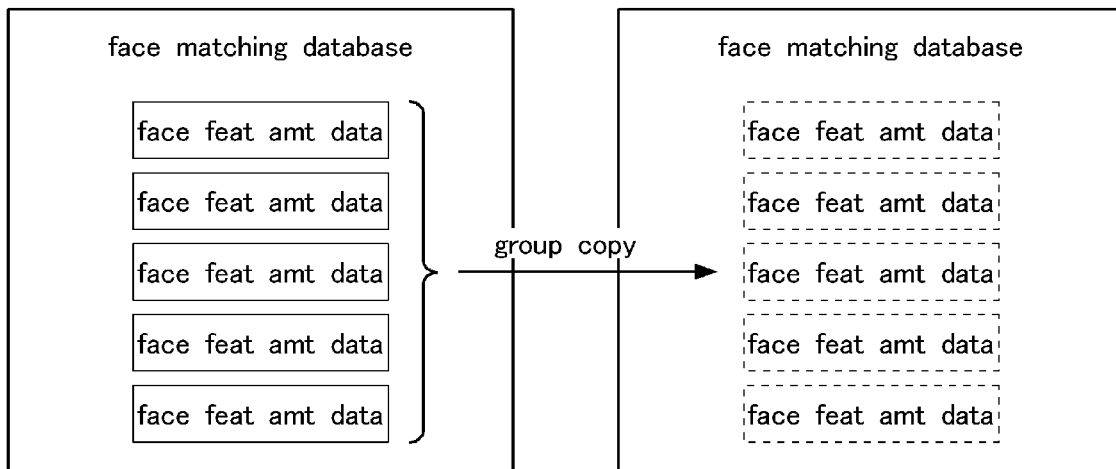

Next, operations for copying face feature amount data will be described. FIGS. 53A-B are explanatory diagrams showing outlines of operations for copying face feature amount data.

In the present embodiment, a face matching server 6 includes a face matching database for each matching group so that face feature amount data of users can be managed separately for each matching group. In addition, the whole system includes a plurality of face matching databases for one matching group in order to achieve the distribution of the computational load on face matching servers 6 and provide a fail-safe against server failure. Thus, the system needs to register face feature amount data of one user in a plurality of face matching databases. However, as performing the operations of generating face feature amount data from face image data of a user require a high computational load on a server, it is not efficient that a plurality of face matching servers 6 independently perform the same operations for face feature amount generation.

Thus, in the present embodiment, when face feature amount data of a user has already been generated and registered in a face matching database, the face feature amount data can be copied from one face matching database to another face matching database. In other words, face feature amount data registered in a face matching database can be used to register the face feature amount data in a different face matching database.

The face information manager 66 of the face management server 5 manages face feature amount data of each user in the face matching database based on data in the face information database, and when face image data of a user is changed, the face information manager 66 instructs a matching server(s) to copy the face feature amount data between the two face matching databases (transfer instruction).

When there is a change in data of an individual(s), the face information manager 66 copies the face feature amount data of each individual (individual copy) as shown in FIG. 53A. For example, when a user is newly registered or updated, the face information manager 66 copies the face feature amount data in each individual. To give another example, in order to improve the accuracy of face matching for a certain user, additional face feature amount data may be generated from data of a different face image so that a plurality of face feature amount data sets are register for the same user. In this case, the face information manager 66 copies the individual face feature amount data only for a specific user.

When there is a change in data for all users of a matching group(s), the face information manager 66 copies the face feature amount data of users on a matching group basis (group copy) as shown in FIG. 53B. For example, when a matching group is newly registered, the face information manager 66 collectively copies face feature amount data in a face matching database in which the face feature amount data is originally registered, to the second and subsequent face matching databases so that each of these databases includes the same face feature amount data. To give another example, when the system includes a plurality of face matching databases each containing the same data in order to achieve load distribution and redundancy of data, the face information manager 66 copies face feature amount data of users on a matching group basis.

Figure 54:
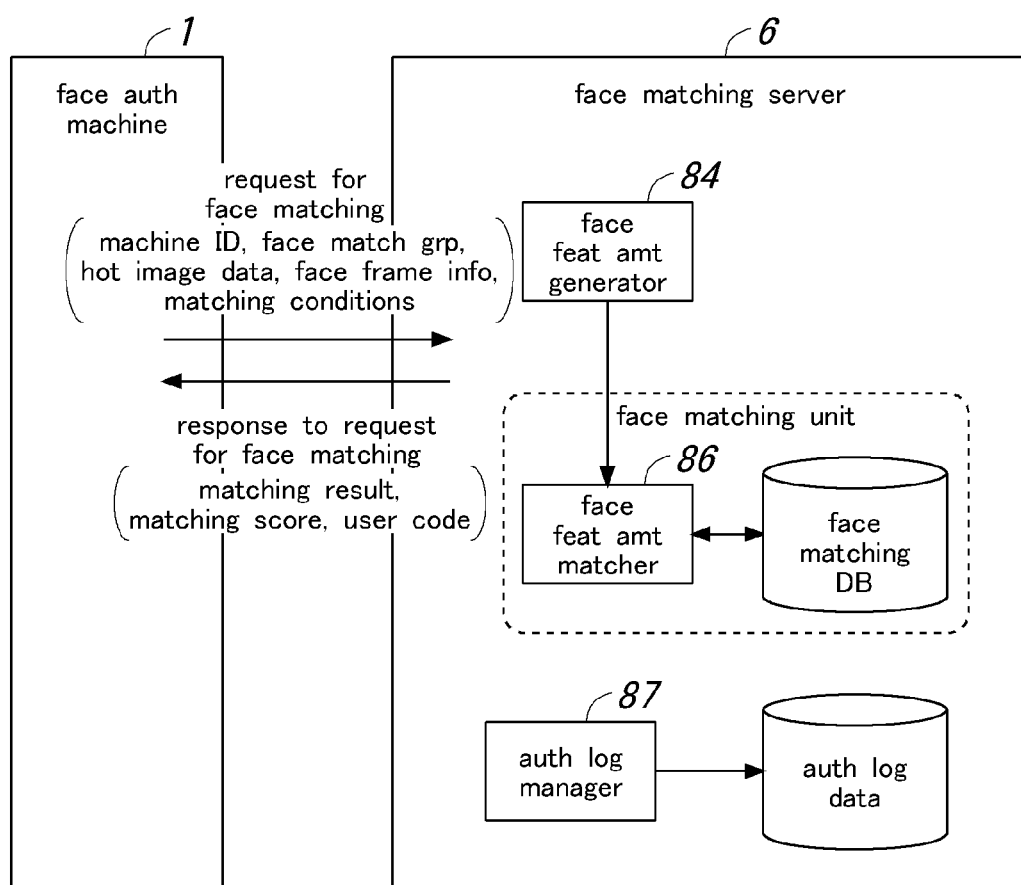
FIG. 54 is an explanatory diagram showing an outline of operations for face authentication.

Next, operations for face authentication performed by the system will be described. FIG. 54 is an explanatory diagram showing an outline of operations for face authentication.

A face authentication machine 1 detects a person's face from an image captured by the camera 11 to acquire a face image, and then transmits a request for face matching to a face matching server 6. The request includes the machine ID of the face authentication machine 1, the matching group to which the face authentication machine 1 belongs, data of a shot image of a target person (a person to be verified through face authentication), face frame information, and matching conditions.

In the face matching server 6, the face feature amount generator 84 generates face feature amount data of the target person from the person's face image acquired from the face authentication machine 1. Next, the face feature amount matcher 86 of a face matching unit for the matching group of the face authentication machine 1 compares the face feature amount data of the target person with face feature amount data of registered users in the face authentication database for matching. A face authentication process which belongs to the matching group of the face authentication machine 1 performs the operation for face matching. When the face matching is completed, the face matching server 6 transmits a response to the request for face matching to the authentication machine 1 which is the source of the request. The response to the request includes a matching result (success, failure), a matching score, and a user code.

The face feature amount matcher 86 calculates a matching score indicating the degree of similarity between the target person and a registered user. When the matching score is equal to or greater than a predetermined reference value, the face feature amount matcher 86 determines that the target person is the registered user, and generates a matching result indicating a success in face matching/recognition. When the matching scores against all registered users do not exceed the reference value, the face feature amount matcher 86 determines that the target person is not a registered user, and generates a matching result indicating a failure in face matching/recognition.

The face authentication machine 1 may add to a request for matching, a condition for face matching (face matching parameter) to be performed by a face matching server 6. This allows the face authentication machine to determine what operations for face matching are to be performed by the face matching server 6. For example, the face authentication machine 1 may designate a predetermined threshold value for the matching score as a condition for face matching, causing the face matching server 6 to generate a response including matching results for which matching scores are equal to or greater than the threshold value. To give another example, the face authentication machine 1 may designate the number of matching results as a condition for face matching, causing the face matching server 6 to generate a response including the designated number of matching results in order from the highest matching score.

When the operations for face matching are completed, the authentication log manager 87 of the face matching server 6 stores a face matching result(s) and other information in the database as an authentication log (history information record of face authentication). The authentication log manager 87 may store only a face authentication result (success, failure) as an authentication log, or may add matching scores to the authentication log. The authentication log manager 87 may add the face image of a target person acquired from the face authentication machine 1 to the authentication log. In this case, the authentication log manager 87 preferably encrypts the face image data of a person before storing it.

When the face feature amount matcher 86 generates a large number of matching results with matching scores that exceed the threshold value, the authentication log manager 87 may narrow down the matching results to a predetermined number of matching results in order from the highest matching score and then stores them as an authentication log. When the operations for face matching are not normally completed, or the face feature amount matcher 86 generates no matching result with the matching score which is greater than the threshold value, the authentication log manager 87 may store only information included in the request from the face authentication machine 1 as an authentication log.

Figure 55:
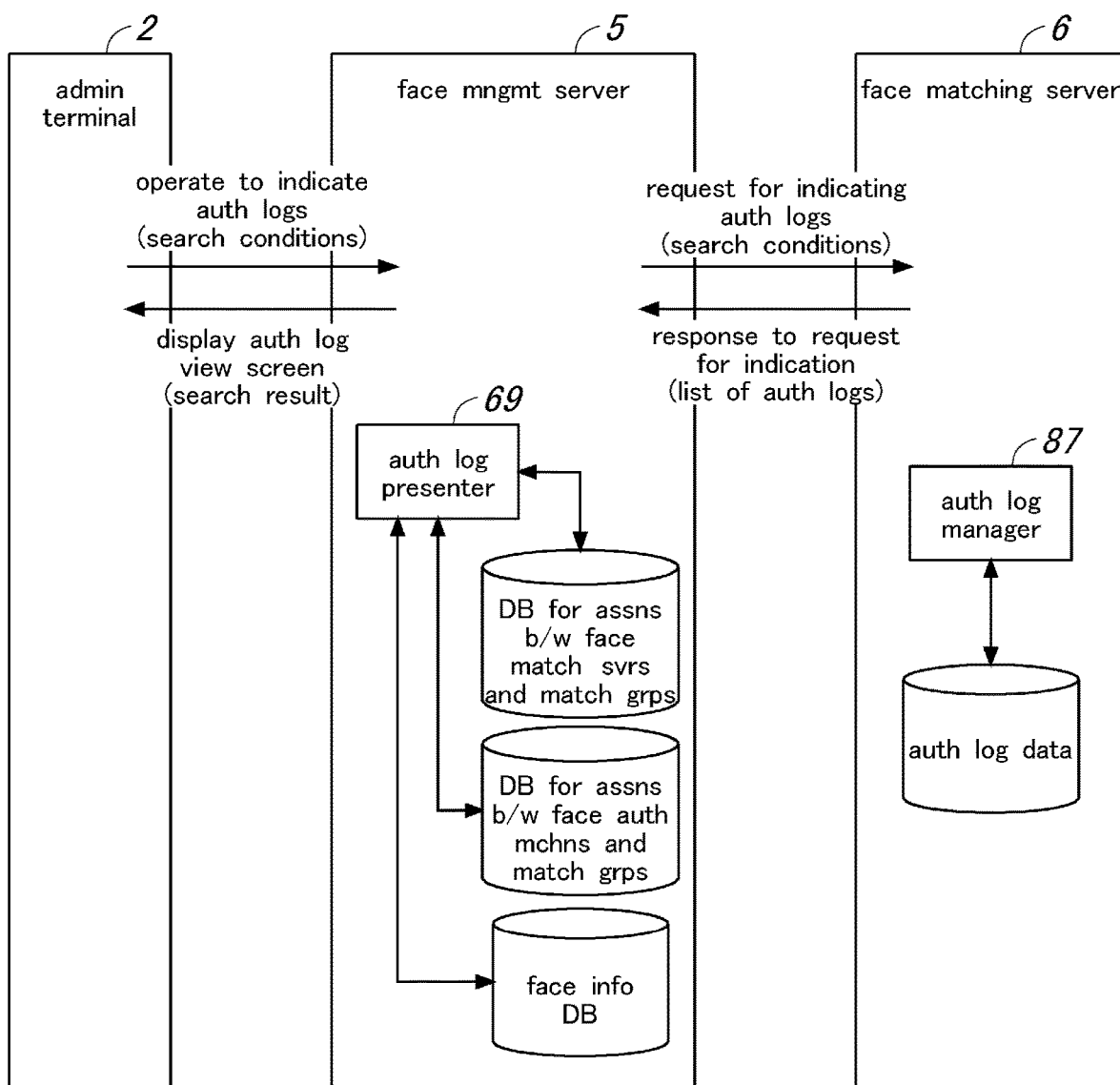
FIG. 55 is an explanatory diagram showing an outline of operations for viewing authentication logs.

FIG. 55 is an explanatory diagram showing an outline of operations for viewing authentication logs.

In response to a request from an administrator terminal 2 via a face management server 5, a face matching server 6 transmits the authentication logs (face recognition history information records) stored in the face matching server 6 to the administrator terminal 2, thereby enabling an administrator to view the authentication log information on the administrator terminal 2. In the operations for viewing the authentication log, the administrator can designate a condition in order to view only the authentication log records that meet to the designated condition.

Specifically, the administrator terminal 2 displays a screen for entry of search conditions for searching the authentication log so that the administrator can operate the screen to designate a search condition(s) such as a specific face authentication machine 1 as a source of requests for face authentication, a specific user, the number of search result to be retrieved, a time when face authentication was performed (search period), and a matching result (success or failure).

When the administrator operates the administrator terminal 2 to enter search conditions and provide instructions to search the authentication log, the authentication log presenter 69 of the face management server 5 transmits a request for viewing the authentication log to the face matching server 6. The request for viewing includes the search conditions designated by the administrator. Then, based on the data of associations between the face authentication machines 1 and the matching groups, the data of associations between the face matching servers 6 and the matching groups, and the user data, the authentication log presenter 69 identifies the target face authentication machine 1 or the face matching server(s) 6 of the same matching group as a user, and transmits a request(s) for viewing authentication log to the face matching server(s) 6. In addition, the face management server 5 records an administrator access log.

When receiving the request for viewing authentication log from the face management server 5, the face matching server 6 searches the authentication log based on the search conditions included in the request, generates a list of authentication logs which meet the search conditions as the search result, adds the generated list to a response to the request for viewing authentication log, and transmits the response to the face management server 5. The face matching server 6 may transmit a face image of a target person as an authentication log to the face management server 5. In this case, since a face image of a person is encrypted, the face matching server 6 decrypts the face image before adding it to the response.

Upon receiving the response to the request for viewing authentication log from the face matching server 6, based on the list of authentication logs included in the response, the face management server 5 causes the administrator terminal 2 to display the search result screen indicating the list of authentication logs which meet the search conditions designated by the administrator. In addition, the face management server 5 further retrieves only the authentication logs which meet such search conditions that cannot be used by the face matching server 6 for narrowing down the authentication logs, and generates a list of authentication logs which have been further narrowed down.

When a list of authentication logs is generated, an administrator can operate the administrator terminal 2 to designate items and provide instructions to sort a list of the authentication logs. When an administrator performs this operation, the face management server 5 sorts the list of authentication logs by the designated items to generate a sorted list of authentication logs. In addition, an administrator can operate the administrator terminal 2 to designate the number of authentication logs to be retrieved. When the administrator performs this operation, the face matching server 6 retrieves the designated number of authentication logs and generates a list of authentication logs. Moreover, an administrator can operate the administrator terminal 2 to designate a search period. When the administrator performs this operation, the face matching server 6 retrieves the authentication logs included in the designated period, and generates a list of authentication logs.

FIG. 56 is an explanatory diagram showing an authentication log view screen displayed on an administrator terminal 2.

The administrator terminal 2 displays the authentication log view screen. The authentication log view screen includes a search condition designation section 151 and a search result display section 152.

An administrator can operate the search condition designation section 151 to enter search conditions at respective item fields; that is, fields of machine ID of the face authentication machine 1, user code, the number of search results to be retrieved, matching date and time, matching result. The field of matching date and time allows an administrator to designate the period (start and end points of time). The filed of matching result provides a pull-down menu which allows an administrator to select any of success, failure, and success and failure. When an administrator designate search conditions for respective fields in the search condition designation section 151 and then operates the search button 153, a face matching server 6 executes a search operation for searching for authentication log records which meet the search conditions, and the search result display section 152 displays a search result.

The search result display section 152 displays, as a search result, a list of retrieved record sets of date and time, matching result (success, failure), and face image. For a success result, the item of face image indicates the face image of a person to be verified through face authentication acquired from the face authentication machine 1 and the face image of a registered user. For a failure result, the item of face image indicates only a face image of a person to be verified through face authentication. This allows an administrator to check authentication log records for the designated face authentication machine 1 and user, and to check authentication log records which have been narrowed down by the matching date and time and the matching result.

An administrator can designate an item (user code, first/last name, matching group) in the search result display section 152 to thereby perform a sort operation (reordering the results). An administrator can operate the save button 154 to store the authentication log records displayed in the search result display section 152 in a prescribed format. This allows the administrator to check authentication log records for the designated face authentication machine 1 and user in chronological order.

Next, dynamic data linking from a face authentication machine to external applications will be described. FIG. 57 is an explanatory diagram showing an outline of dynamic data linking from a face authentication machine to external applications.

A face authentication machine 1 supports dynamic data linking to external applications; that is, a face authentication machine can notify a management server 8 (management device) of an external system of a face authentication result acquired from a face matching server 6. The external system utilizes face authentication results acquired from the present system to provide various services to users. For example, the external system may be an entry/exit management system which performs controls to unlock the door when a face authentication result is success. The external system may be a payment system which performs a payment operation when a face authentication result is success.

A face authentication machine 1 includes an authentication result adjuster 25 (connection application), and notifies a face authentication result to the management server 8 of the external system via the authentication result adjuster 25. The face authentication machine 1 notifies the authentication result adjuster 25 of a face authentication result (success, failure) via a named pipe (inter-process communication). The authentication result adjuster 25 notifies the management server 8 of the external system of a face authentication result via the network using a predetermined protocol (WebSocket). The authentication result adjuster 25 may perform necessary operations such as modification or addition of information records according to how authentication results are used in the external system.

The face matching requester 23 of a face authentication machine 1 transmits a request for face matching to a face matching server 6. Upon receiving a response to the request for face matching from the face matching server 6, the face matching requester 23 writes a face authentication result (authentication success, authentication failure) included in the response in a named pipe and notifies the connection application of the face authentication result. When notifying a face authentication result, the face authentication machine 1 acquires the ID of a person to be verified and the ID of a camera 11 as the authentication result, and adds the IDs to a face authentication result notification. Specifically, for a success result, the face authentication machine 1 writes the user code of a user and the machine ID of the face authentication machine 1 (camera 11) in the named pipe. For a failure result, the face authentication machine 1 writes only the authentication result (authentication failure) to the named pipe.

The authentication result adjuster 25 of a face authentication machine 1 inhibits notification of authentication results so as to prevent the face authentication machine 1 from repeating notification of the same face authentication result to the external system. In the present embodiment, when a face authentication machine 1 notifies the connection application of a face authentication result, the authentication result adjuster 25 sets a notification inhibit time to thereby temporally and automatically stop the face authentication machine 1 notifying the same face authentication result within the notification inhibit time.

When a face authentication machine 1 notifies a face authentication success result for a certain person, the authentication result adjuster 25 inhibits notification of face authentication success results for the person within a predetermined time (authentication success notification inhibit time) from the first notification of authentication success. When a face authentication machine 1 notifies a face authentication failure result for a certain person, the authentication result adjuster 25 inhibits notification of authentication failure results for the person within a predetermined time (authentication failure notification inhibit time) from the first notification of authentication failure.

The individual notification inhibit times are set depending on the authentication results (authentication success, authentication failure) and the persons to be verified; that is, different notification inhibit times for the same person are set for the different authentication results, and different notification inhibit times for the same authentication result are set for the different persons to be verified. Therefore, within an authentication failure notification inhibit for a person, the face authentication machine 1 can notify an external system of a face authentication success result for the person, whereas, within an authentication success notification inhibit for a person, the face authentication machine 1 can notify an external system of a face authentication failure result for the person. Within an authentication failure notification inhibit for a person, the face authentication machine 1 can notify an external system of a face authentication failure result for a different person, whereas, within an authentication success notification inhibit for a person, the face authentication machine 1 can notify an external system of a face authentication success result for a different person.

Figure 58:
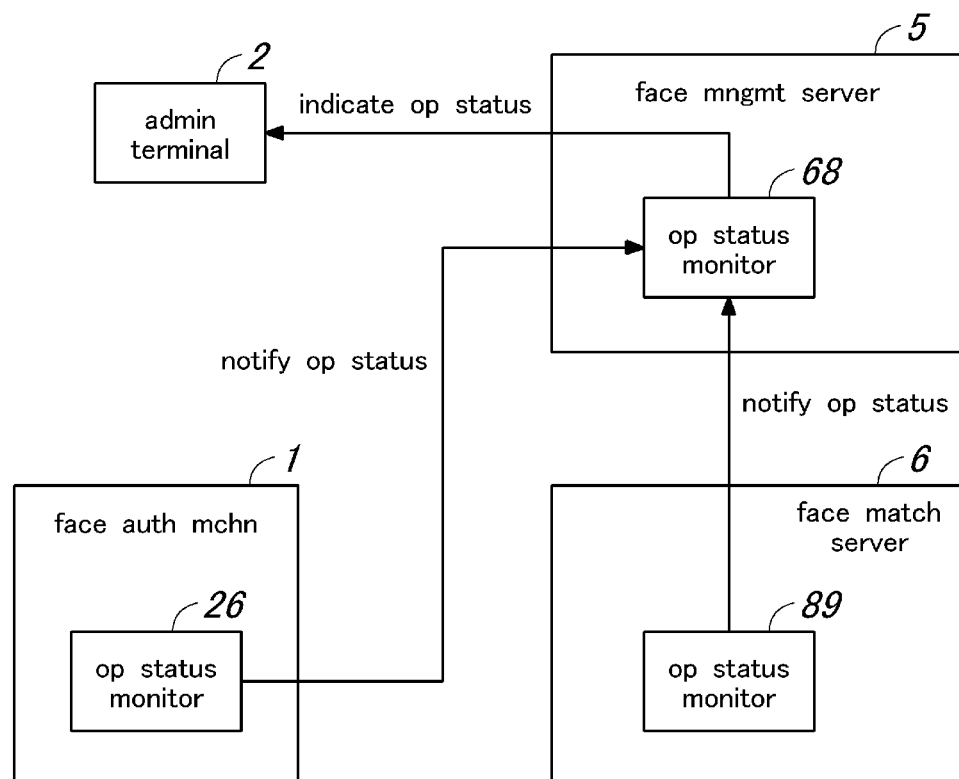
FIG. 58 is an explanatory diagram showing an outline of monitoring the operation statuses of the present system.

Next, monitoring the operation statuses of the present system will be described. FIG. 58 is an explanatory diagram showing an outline of monitoring the operation statuses of the present system.

A face authentication machine 1 includes an operation status monitor 26. The operation status monitor 26 monitors the operation status of the face authentication machine 1, and periodically notifies a face management server 5 (monitoring server) of the operation status (failure or non-failure status) at a predetermined period of time. A face matching server 6 includes an operation status monitor 89. The operation status monitor 89 monitors the operation status of the face matching server 6, and periodically notifies the face management server 5 (monitoring server) of the operation status (failure or non-failure status) at a predetermined period of time.

A face management server 5 includes an operation status monitor 68. The operation status monitor 68 monitors the operation status of the face management server 5, and periodically records the operation status (failure or non-failure status) therein at a predetermined period of time. The face management server 5 also records the operation status notified from a face authentication machine 1 and a face matching server 6 therein.

Information records of an operation status to be notified include the machine ID, time of acquiring record, failure or non-failure status, program version information, and other records.

An administrator terminal 2 can check the operation statuses by transmitting a request for operation status view to a face management server 5.

Next, operations for updating databases upon upgrade of a program in a face matching server 6 will be described.

In a face matching server 6, programs for face feature amount generation and face matching are upgraded (updated) as appropriate in order to improve the accuracy of face matching. Generally, face feature amount data depends on the algorithms of face feature amount generation and face matching. Thus, changes in the algorithms result in changes in face feature amount data, thereby necessitating regeneration of face feature amount data.

Thus, in the present embodiment, when a program related to face feature amount generation or face matching algorithm is upgraded, the face feature amount data registered in a face matching database is updated so as to be adapted to the upgraded program. Specifically, a face matching server 6 deletes the face feature amount data already stored therein, regenerates face feature amount data based on the face image data at the time of user registration, and stores the regenerated face feature amount data in the face matching server 6.

Specifically, when detecting an upgrade of a face matching program, the face management server 5 uses its operation status notification function to transmit a request for updating face feature amount data to a face matching server 6. The request includes face images of users. Upon receiving the request for updating face feature amount data, the face feature amount manager 85 of the face matching server 6 causes the face feature amount generator 84 to perform the operations for generating face feature amount data from the users' face images, and registers the new face feature amount data in the face matching database.

When a plurality of face matching servers 6 have the same face matching process and the same face matching database; that is, when the plurality of face matching servers 6 include the respective face matching databases containing the same registered face feature amount data, and the respective face matching processes used for matching operations for the same face authentication machine 1 of the same matching group, one of the face matching servers 6 regenerates face feature amount data and registers the regenerated face feature amount data in the face matching database, and then a face management server 5 copies the regenerated face feature amount data registered in the face matching database to different face matching servers 6 so that the different face matching databases of the respective face matching servers 6 contain the same registered face feature amount data.

In this case, the face management server 5 instructs a new face matching server 6 to store copied data, and transfers the face feature amount data stored in the source face matching server 6 to the new face matching server 6.

Next, the operations for backup and restoration of data will be described.

In the present embodiment, databases and files stored in a face management server 5 and a face matching server 6 can be backed up and restored.

Among the data stored in a face management server 5, backup target data (data to be backed up) includes a user information (face information) database, face image files, a matching group information database, a database of associations between face authentication machines and matching groups, a database of associations between matching servers and matching groups, and an administrator access log file.

Among the data stored in a face matching server 6, backup target data includes a database of authentication log records, and files of face images.

FIG. 59 is an explanatory diagram showing a backup screen and a restoration screen displayed on the administrator terminal 2. The screen can be switched between the backup screen and the restore screen by clicking tabs.

Figure 59A:
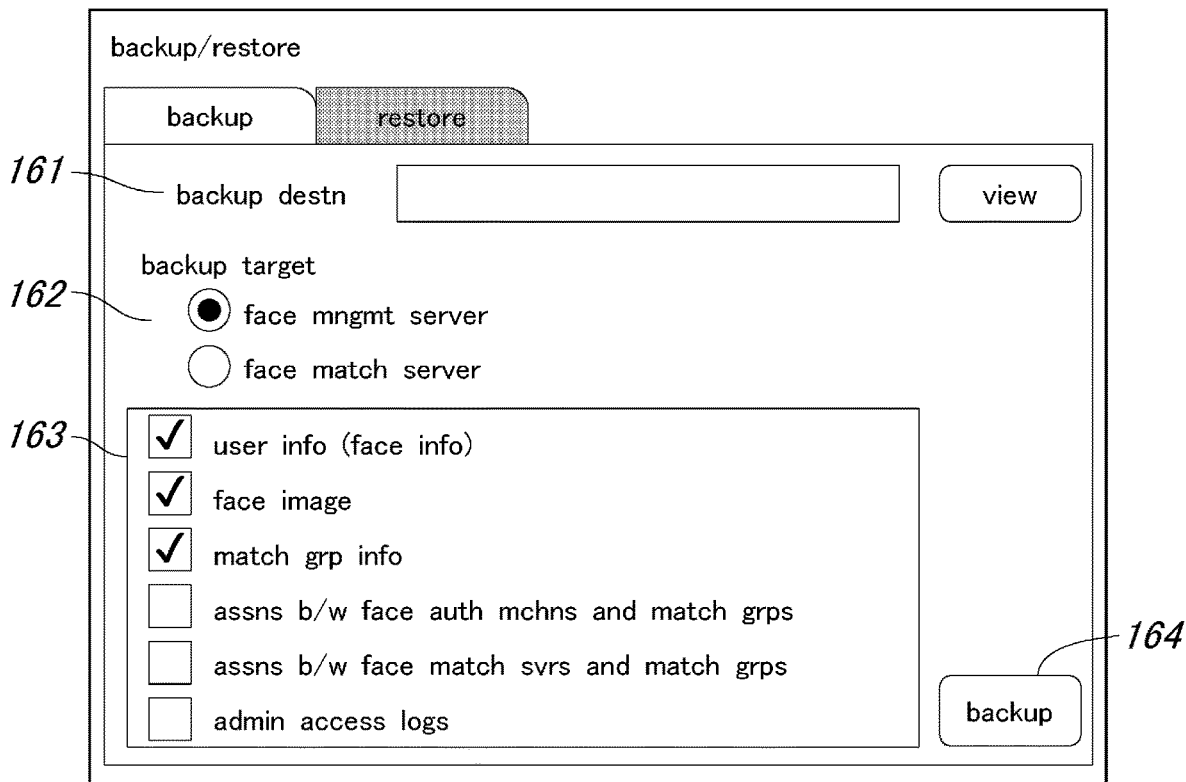
FIGS. 59A-B are explanatory diagrams showing a backup screen and a restoration screen displayed on the administrator terminal 2.

As shown in FIG. 59A, the backup screen includes a backup destination designation section 161, a backup target designation section 162, a progress indication section 163, and an execute button 164. The backup destination designation section 161 allows an administrator to designate a backup destination. The backup target designation section 162 allows an administrator to select a face management server 5 and a face matching server 6 as backup operation target devices. An administrator operates the execute button 164 to start the backup operation. The progress indication section 163 indicates a list of data items to be backed up. For each item to be backed up, a check mark is indicated upon completion of the data backup so that the administrator can recognize the progress of the backup operation.

The backup target data (data to be backed up) includes a user information (face information) database, face image files of registered users, a matching group information database, a database of associations between face authentication machines and matching groups, a database of associations between matching servers and matching groups, an administrator access log file, an authentication log database, and face image files of persons to be verified through face authentication.

Figure 59B:
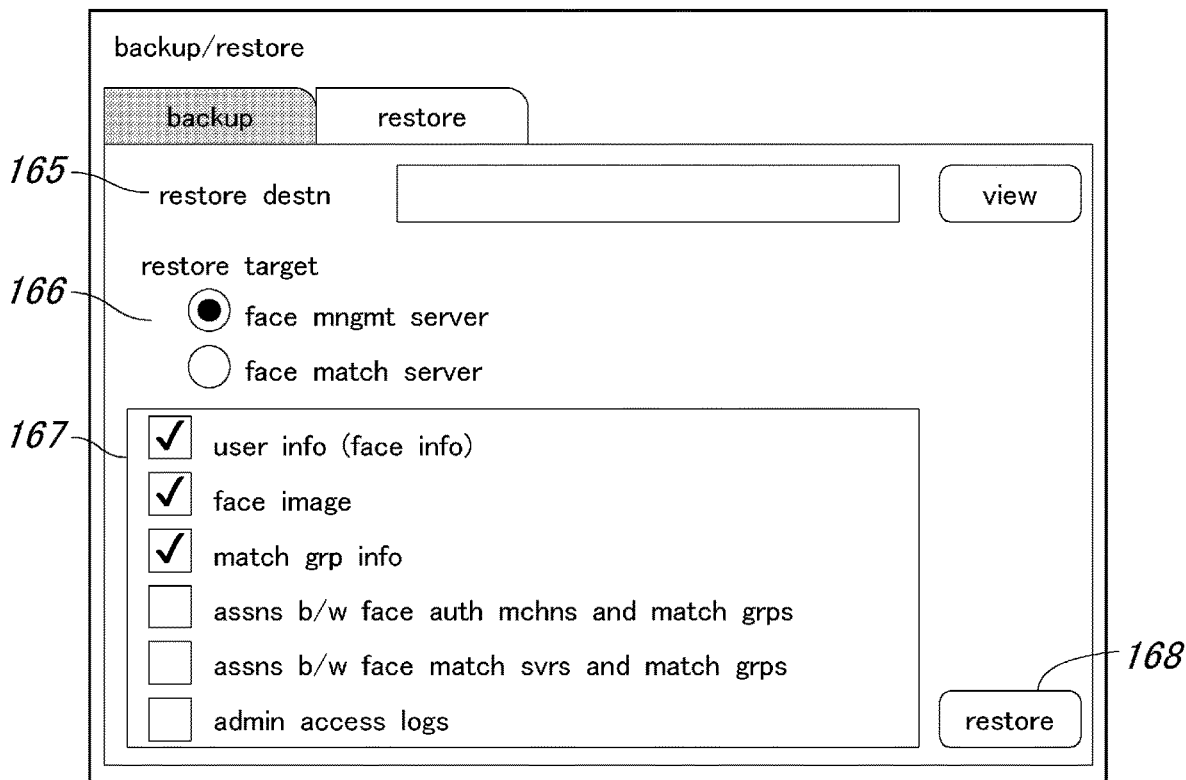

As shown in FIG. 59B, the restore screen includes a restore destination designation section 165, a restore target designation section 166, a progress indication section 167, and an execute button 168 in a similar manner to the backup screen. The restore destination designation section 165 allows an administrator to designate a restore destination. The restore target designation section 166 allows an administrator to select a face management server 5 and a face matching server 6 as restore target devices. An administrator operates the execute button 168 to start the restore operation. The progress indication section 167 indicates a list of data items to be restored. For each item to be restored, a check mark is indicated upon completion of the data restore so that the administrator can recognize the progress of the restore operation.

Figure 60:
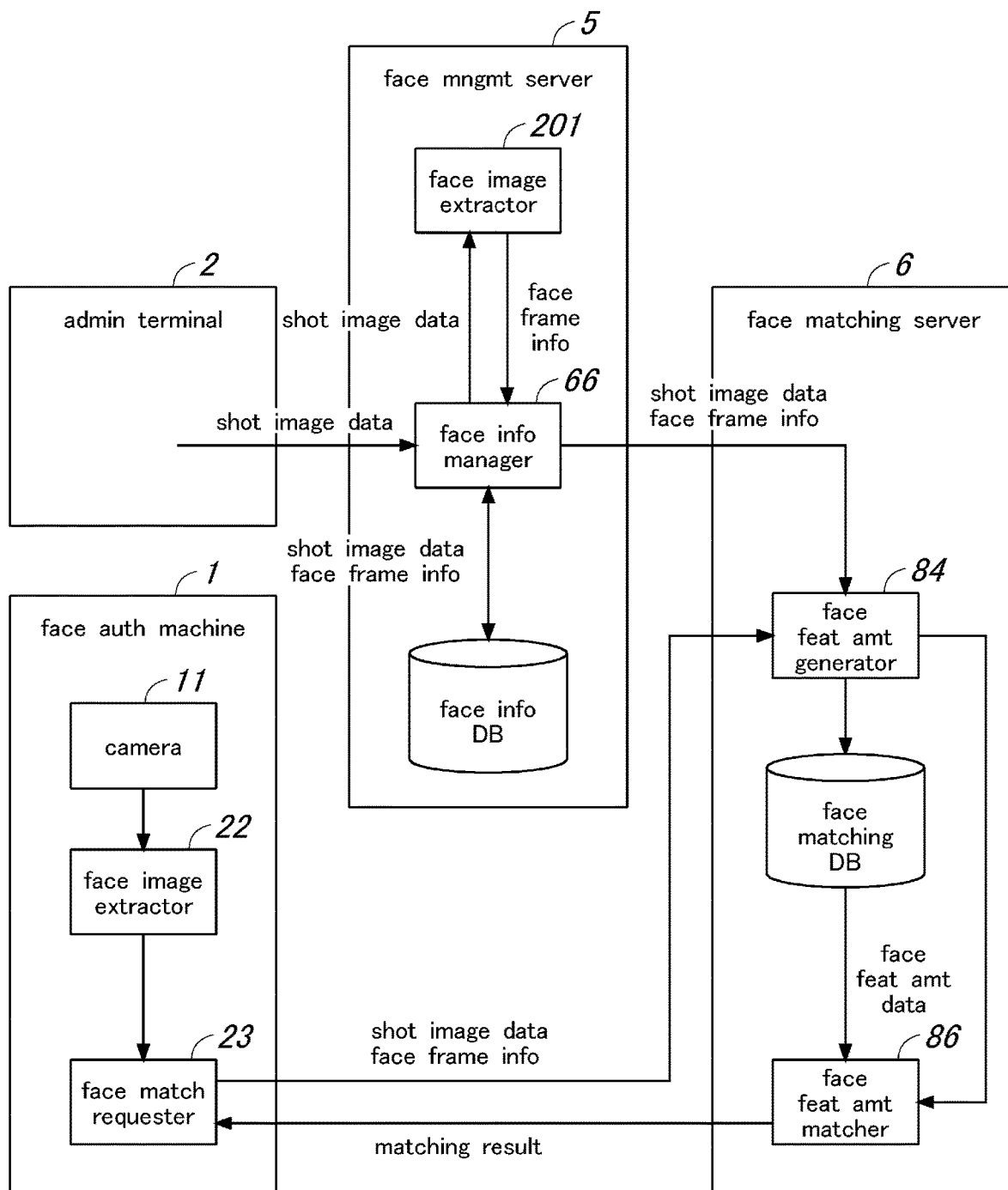
FIG. 60 is an explanatory diagram showing an outline of operations for face image extraction according to a variation of the present embodiment.

Next, a variation of the above-described embodiment will be described. FIG. 60 is an explanatory diagram showing an outline of operations for face image extraction according to a variation of the present embodiment.

In n the above-described embodiment (see FIG. 12), a face authentication machine 1 and a face matching server 6 perform the operations for face image extraction to generate a face image from a shot image data of a user. In the variation of the embodiment, a face authentication machine 1 and a face management server 5 perform the operations for face image extraction and a face matching server 6 does not perform the operations for face image extraction. Specifically, in the variation of the embodiment, the face matching server 6 does not include the face image extractor 83 in the above-described embodiment, and the face management server 5 includes a face image extractor 201.

At the time of user registration, an administrator terminal 2 transmits a shot image data of a user to a face management server 5, and then the face image extractor 201 of the face management server 5 performs the operations for face image extraction. At the time of face authentication, the face image extractor 22 in the face authentication machine 1 in the same manner as the above-described embodiment.

While specific embodiments of the present invention are described herein for illustrative purposes, the present invention is not limited to the specific embodiments. It will be understood that various changes, substitutions, additions, and omissions may be made for elements of the embodiments without departing from the scope of the invention. In addition, elements and features of the different embodiments may be combined with each other as appropriate to yield an embodiment which is within the scope of the present invention.

In recent years, in the technical filed of IoT (Internet of Things), CPS (Cyber Physical System), which is a new technical concept for creating new added value by a higher combination and coordination between information in the physical space and that in the cyberspace, has been drawing attention. The concept of CPS can be adopted in the present embodiment. Specifically, as a basic configuration of CPS, a system may be configured to include, for example, an edge device provided in physical space and a cloud server provided in cyberspace, which are connected to each other via a network and which can achieve the distributed processing by using the respective processors when performing a face authentication process. Specifically, a camera of a face authentication machine, i.e., an edge device, is used to acquire face image data of a user. Then, upon receiving the face image data from the edge device via a network, a cloud server generates face feature amount data from the received face image data, and compares the generated face feature amount data with registered face feature amount data of users for matching to perform a face authentication process of the user, to thereby generate a face authentication result. A face authentication application uses the generated face authentication result to display the result on a display screen in a certain format defined by the application. When an edge device and a cloud server generate data, Web application software on a standardized platform is preferably used. By using such a standardized platform, a system including various type of sensors and IoT applications can be built in an efficient manner.

INDUSTRIAL APPLICABILITY

A system and a method for face authentication according to the present invention achieve an effect of enabling the system for face authentication to operate separately for individual providers of face authentication service in a stable and sufficient manner, and are useful as a system for face authentication and a method for face authentication used for performing a face authentication process based on image data of a person to be verified.

Glossary 1 face authentication machine
2 administrator terminal (terminal device, face authentication administrator's device)
3 face authentication server (server device)
5 face management server (face image manager)
6 face matching server (face image matcher)

What is claimed is:

1. A system for face authentication used for performing a face authentication process based on a face image of a person to be verified, the face image being acquired by imaging the person to be verified, the system comprising:
a plurality of face authentication machines;
a server device connected to the plurality of face authentication machines via a network; and
a face authentication administrating device connected to the server device via the network, and operated by an administrator,
wherein each of the plurality of face authentication machines comprises a camera for imaging the person to be verified,
wherein the server device comprises:
a face management server for storing and accumulating face image data of users in association with respective matching groups corresponding to organizations to which the users belong; and
a plurality of face matching servers, each face matching server being configured to store face feature amount data, the face feature amount data being generated from the face image data of the users when the face image data of the users is registered or updated, the face feature amount data of the users being stored separately for the respective matching groups for the corresponding organizations, each face matching server being further configured to perform a matching operation between the face feature amount data stored separately for the respective matching groups and face feature amount data generated from face image data of the person to be verified and acquired from one of the plurality of face authentication machines,
wherein the face authentication administrating device displays operation screens that set association information required for the face management server and the plurality of face matching servers, and
wherein the operation screens comprise:
a first screen that receives first operations to register the respective matching groups;
a second screen that receives second operations to set the association information regarding first associations between the respective matching groups registered by the first screen and the plurality of face matching servers; and
a third screen that receives third operations to set the association information regarding second associations between the users and the respective matching groups registered by the first screen, the third screen setting the association information regarding the second associations when face image data of a user is registered.

2. A face authentication administrating device to be operated by an administrator for administrating a system for face authentication, the face authentication administrating device comprising a display device that displays various types of screens,
wherein the face authentication administrating device is connected to a server device via a network, wherein the server device includes a face management server and a plurality of face matching servers, the face authentication administrating device displaying operation screens that set association information required for operations performed by the face management server and the plurality of face matching servers, the operations including:
a first operation to store and accumulate face image data of users, in the face management server of the server device, in association with respective matching groups corresponding to organizations to which the users belong;
a second operation to generate face feature amount data from the face image data of the users and store the face feature amount data separately for the respective matching groups corresponding to the organizations to which the users belong, the second operation being performed by each of the plurality of face matching servers of the server device; and
a matching operation between the face feature amount data of the users stored separately for the respective matching groups and face feature amount data generated from face image data of a person to be verified, the face image data of the person to be verified being acquired by a camera of a face authentication machine, the matching operation being performed by at least one of the plurality of face matching servers of the server device, the at least one of the plurality of face matching servers performing the matching operation when acquiring the face image data of the person to be verified from the face authentication machine, and
wherein the operation screens comprise:
a first screen that receives first operations to register the respective matching groups;
a second screen that receives second operations to set the association information regarding first associations between the respective matching groups registered by the first screen and the plurality of face matching servers; and
a third screen that receives third operations to set the association information regarding second associations between the users and the respective matching groups registered by the first screen, the third screen setting the association information regarding the second associations when face image data of a user is registered.

3. A face authentication administrating method for administrating a system for face authentication, the face authentication administrating method being performed by a processor of a face authentication administrating device, the face authentication administrating device to be operated by an administrator, the face authentication administrating method displaying operation screens that set association information required for operations performed by a face management server and a plurality of face matching servers, the operations comprising:

a first operation to store and accumulate face image data of users, in the face management server of a server device, in association with respective matching groups corresponding to organizations to which the users belong, the server device including the face management server and the plurality of face matching servers, the server device being connected to the face authentication administrating device via a network;

a second operation to generate face feature amount data from the face image data of the users and store the face feature amount data separately for the respective matching groups corresponding to the organizations to which the users belong, the second operation being performed by each of the plurality of face matching servers of the server device when the face image data of the users is registered or updated; and a matching operation between the face feature amount data of the users stored separately for the respective matching groups and face feature amount data generated from face image data of a person to be verified, the face image data of the person to be verified being acquired by a camera of a face authentication machine, the matching operation being performed by at least one of the plurality of face matching servers of the server device, the at least one of the plurality of face matching servers performing the matching operation when acquiring the face image data of the person to be verified from the face authentication machine, and wherein the operation screens comprise:
- a first screen that receives first operations to register the respective matching groups;
- a second screen that receives second operations to set the association information regarding first associations between the respective matching groups registered by the first screen and the plurality of face matching servers; and
- a third screen that receives third operations to set the association information regarding second associations between the users and the respective matching groups registered by the first screen, the third screen setting the association information regarding the second associations when face image data of a user is registered.

4. A non-transitory computer-readable storage medium, comprising a face authentication administrating program, the face authentication administrating program comprising instructions which, when executed by a processor of a face authentication administrating device, cause the processor to carry out a face authentication administrating method, the face authentication administrating device being operated by an administrator, the face authentication administrating method comprising:

displaying operation screens that set association information required for operations performed by a face management server and a plurality of face matching servers, the operations comprising:

a first operation to store and accumulate face image data of users, in the face management server of a server device, in association with respective matching groups corresponding to organizations to which the users belong, the server device including the face management server and the plurality of face matching servers, the server device being connected to the face authentication administrating device via a network;

a second operation to generate face feature amount data from the face image data of the users and store the face feature amount data separately for the respective matching groups corresponding to the organizations to which the users belong, the second operation being performed by each of the plurality of face matching servers of the server device when the face image data of the users is registered or updated; and a matching operation between the face feature amount data of the users stored separately for the respective matching groups and face feature amount data generated from face image data of a person to be verified, the face image data of the person to be verified being acquired by a camera of a face authentication machine, the matching operation being performed by at least one of the plurality of face matching servers of the server device, the at least one of the plurality of face matching servers performing the matching operation when acquiring the face image data of the person to be verified from the face authentication machine, and wherein the operation screens comprise:
- a first screen that receives first operations to register the respective matching groups;
- a second screen that receives second operations to set the association information regarding first associations between the respective matching groups registered by the first screen and the plurality of face matching servers; and
- a third screen that receives third operations to set the association information regarding second associations between the users and the respective matching groups registered by the first screen, the third screen setting the association information regarding the second associations when face image data of a user is registered.

* * * * *